US009381240B2

(12) United States Patent
Mahony

(10) Patent No.: US 9,381,240 B2
(45) Date of Patent: Jul. 5, 2016

(54) RECOMBINANT LOW VIRULENCE BOVINE HERPESVIRUS-1 (BOHV-1) VACCINE VECTORS

(75) Inventor: Timothy John Mahony, Bellbowrie (AU)

(73) Assignees: THE STATE OF QUEENSLAND ACTING THROUGH THE DEPARTMENT OF AGRICULTURE AND FISHERIES, Brisbane, Queensland (AU); MEAT & LIVESTOCK AUSTRALIA LIMITED, North Sydney, New South Wales (AU)

( * ) Notice: Subject to any disclaimer, the term of this patent is extended or adjusted under 35 U.S.C. 154(b) by 0 days.

(21) Appl. No.: 14/130,904

(22) PCT Filed: Jul. 4, 2012

(86) PCT No.: PCT/AU2012/000804
§ 371 (c)(1),
(2), (4) Date: Feb. 3, 2014

(87) PCT Pub. No.: WO2013/003904
PCT Pub. Date: Jan. 10, 2013

(65) Prior Publication Data
US 2014/0147466 A1 May 29, 2014

(30) Foreign Application Priority Data
Jul. 5, 2011 (AU) ................. 2011902660

(51) Int. Cl.
A61K 39/245 (2006.01)
A61K 39/12 (2006.01)
C12N 15/86 (2006.01)
A61K 39/00 (2006.01)

(52) U.S. Cl.
CPC ............... *A61K 39/245* (2013.01); *A61K 39/12* (2013.01); *C12N 15/86* (2013.01); *A61K 2039/5254* (2013.01); *A61K 2039/5256* (2013.01); *A61K 2039/543* (2013.01); *A61K 2039/552* (2013.01); *A61K 2039/58* (2013.01); *A61K 2039/70* (2013.01); *C12N 2710/16734* (2013.01); *C12N 2710/16743* (2013.01); *C12N 2770/24334* (2013.01); *C12N 2800/204* (2013.01)

(58) Field of Classification Search
None
See application file for complete search history.

(56) References Cited

U.S. PATENT DOCUMENTS

| 5,874,280 A * | 2/1999 | Keil ........................... 435/235.1 |
| 6,410,033 B1 * | 6/2002 | Cochran ..................... 424/229.1 |
| 2014/0147466 A1 * | 5/2014 | Mahony ..................... 424/199.1 |

OTHER PUBLICATIONS

Robinson et al. (Journal of General Virology. 2008; 89: 2851-2863).*
Kweon et al. (Journal of Veterinary Medicine. 1999; 61 (4): 395-401).*
Morimoto et al. (Microbiology and Immunology. 2009; 53: 155-161).*
Mahony, T.J. et al. 2002 "Construction and manipulation of an infectious clone of the Bovine Herpesvirus 1 Genome maintained as a bacterial artificial chromosome" *Journal of Virology* 76:13, 6660-6668.
Risk Assessment and Risk Management Plan 2005 "Vaccination of cattle with recombinant bovine herpesvirus vaccines" *Department of Health and Ageing*.
Schmitt, J. et al. 1999 "Expression of bovine viral diarrhea virus glycoprotein E2 by bovine herpesvirus-1 from a synthetic ORF and incorporation of E2 into recombinant virions" *Journal of General Virology* 80, 2839-2848.
Schrijver, R.S. et al 1997 "Immunization of cattle with a BHV1 vector vaccine or a DNA vaccine both coding for the G protein of BRSV" *Vaccine* 15:17/18, 1908-1916.
Wang, L. et al. 2003 "A Hepadnavirus regulatory element enhances expression of a type 2 bovine viral diarrhea virus E2 protein from a bovine herpesvirus 1 vector" *Journal of Virology* 77: 8775-8782.

* cited by examiner

*Primary Examiner* — Shanon A Foley
(74) *Attorney, Agent, or Firm* — Knobbe, Martens, Olson & Bear, LLP

(57) ABSTRACT

The present disclosure teaches generally in the field of vaccination and disease control in cattle and bovine animals. A recombinant bovine herpesvirus 1 (BoHV-1) vaccine vector is provided for efficient control of one or more bovine pathogens such as those associated with bovine respiratory disease complex, such as bovine viral diarrhea virus (BVDV), and which ameliorates disease conditions caused thereby. Protocols for the management of confined or herded bovine animals are also enabled herein.

18 Claims, 2 Drawing Sheets

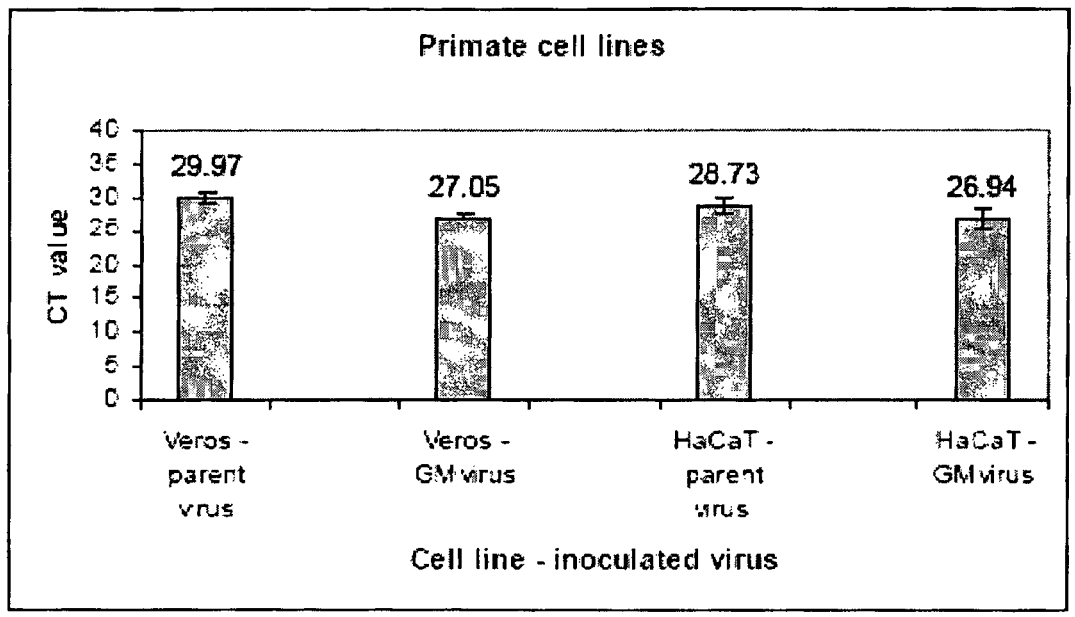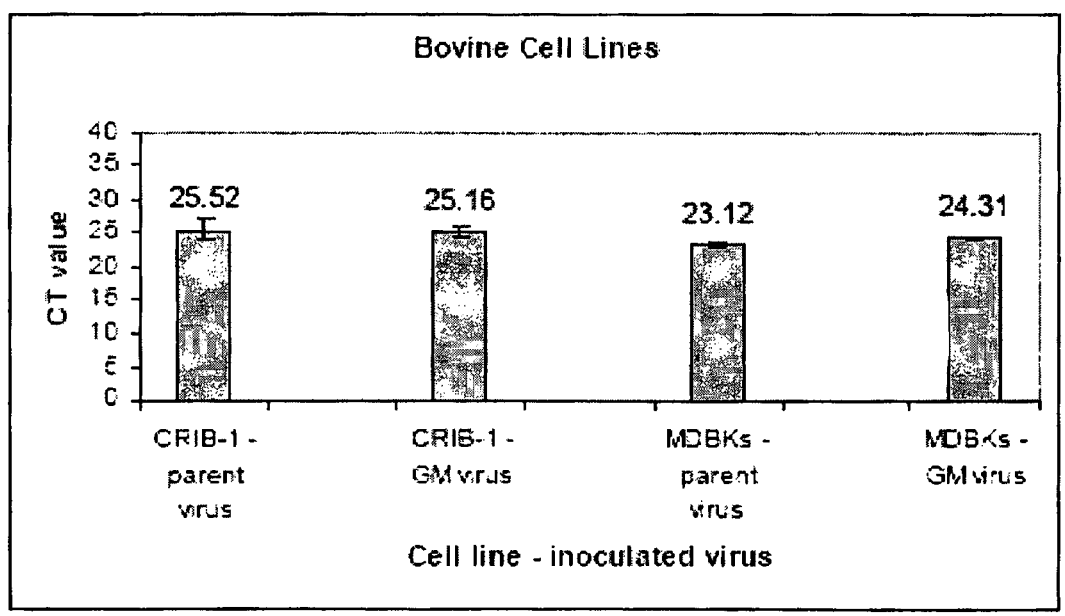
Figures 1A/B

SEQUENCE LISTING

```
<160> NUMBER OF SEQ ID NOS: 12

<210> SEQ ID NO 1
<211> LENGTH: 38
<212> TYPE: DNA
<213> ORGANISM: Artificial Sequence
<220> FEATURE:
<223> OTHER INFORMATION: oligonucleotide primer (TKleft5')

<400> SEQUENCE: 1
gtggtaccat gcatctgata ccccttcgcc cgctactg                              38

<210> SEQ ID NO 2
<211> LENGTH: 30
<212> TYPE: DNA
<213> ORGANISM: Artificial Sequence
<220> FEATURE:
<223> OTHER INFORMATION: oligonucleotide primer (TKleft3')

<400> SEQUENCE: 2
tttgcgtcga cccactccag cgcgtcccag                                      30

<210> SEQ ID NO 3
<211> LENGTH: 27
<212> TYPE: DNA
<213> ORGANISM: Artificial Sequence
<220> FEATURE:
<223> OTHER INFORMATION: oligonucleotide primer (TKright5')

<400> SEQUENCE: 3
atgaattcgc cgcgctcgca gacccca                                         27

<210> SEQ ID NO 4
<211> LENGTH: 33
<212> TYPE: DNA
<213> ORGANISM: Artificial Sequence
<220> FEATURE:
<223> OTHER INFORMATION: oligonucleotide primer (TKright3')

<400> SEQUENCE: 4
ggactagtca tgcatctcta gcgcgaactg acg                                  33

<210> SEQ ID NO 5
<211> LENGTH: 22
<212> TYPE: DNA
<213> ORGANISM: Artificial Sequence
<220> FEATURE:
<223> OTHER INFORMATION: oligonucleotide primer (ChloramF)

<400> SEQUENCE: 5
tcactggata taccaccgtt ga                                              22

<210> SEQ ID NO 6
<211> LENGTH: 22
<212> TYPE: DNA
<213> ORGANISM: Artificial Sequence
<220> FEATURE:
```

<223> OTHER INFORMATION: oligonucleotide primer (ChloramR)

<400> SEQUENCE: 6
tcaccgtaac acgccacatc tt                                              22

<210> SEQ ID NO 7
<211> LENGTH: 85
<212> TYPE: DNA
<213> ORGANISM: Artificial Sequence
<220> FEATURE:
<223> OTHER INFORMATION: oligonucleotide primer (Ge-KanF)

<400> SEQUENCE: 7
ggggaacggc gcacgcgaga gggttcgaaa agggcatttg gcaatgcaac atttaaatcc     60
acgttgtgtc tcaaaatctc tgatg                                          85

<210> SEQ ID NO 8
<211> LENGTH: 85
<212> TYPE: DNA
<213> ORGANISM: Artificial Sequence
<220> FEATURE:
<223> OTHER INFORMATION: oligonucleotide primer (gE-KanR)

<400> SEQUENCE: 8
tcgcgctgct accacggtgt aatctggtgc ggccggggtc cgcgctggcg atttaaatcg     60
gttgatgaga gctttgttgt aggtg                                          85

<210> SEQ ID NO 9
<211> LENGTH: 19
<212> TYPE: DNA
<213> ORGANISM: Artificial Sequence
<220> FEATURE:
<223> OTHER INFORMATION: oligonucleotide primer (BHV1.3)

<400> SEQUENCE: 9
gggcatttgg caatgcaac                                                  19

<210> SEQ ID NO 10
<211> LENGTH: 19
<212> TYPE: DNA
<213> ORGANISM: Artificial Sequence
<220> FEATURE:
<223> OTHER INFORMATION: oligonucleotide primer (BHV1.6)

<400> SEQUENCE: 10
cgtctcgtat atgcggatg                                                  19

<210> SEQ ID NO 11
<211> LENGTH: 24
<212> TYPE: DNA
<213> ORGANISM: Artificial Sequence
<220> FEATURE:
<223> OTHER INFORMATION: oligonucleotide primer (KanRfwd)

<400> SEQUENCE: 11
ggtattagaa gaatatcctg attc                                            24

<210> SEQ ID NO 12
<211> LENGTH: 23
<212> TYPE: DNA
<213> ORGANISM: Artificial Sequence
<220> FEATURE:
<223> OTHER INFORMATION: oligonucleotide primer (KanRrev)

```
<400> SEQUENCE: 12
ctcatcgagc atcaaatgaa act                                                    23
```

RECOMBINANT LOW VIRULENCE BOVINE HERPESVIRUS-1 (BOHV-1) VACCINE VECTORS

This application is associated with and claims priority from Australian Provisional Patent Application No. 2011902660, filed on 5 Jul. 2011, entitled "A vaccine", the entire contents of which, are incorporated herein by reference.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 16961200_1.TXT, the date of creation of the ASCII text file is Jan. 3, 2014, and the size of the ASCII text file is 2.89 KB.

FIELD

The present disclosure teaches generally in the field of vaccination and disease control in bovine animals. A vaccine vector is provided for efficient control of one or more bovine pathogens such as those associated with bovine respiratory disease complex and which ameliorates disease conditions caused thereby. Protocols for the management of confined or herded bovine animals are also enabled herein.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Bovine Respiratory disease complex (BRDC) is the most significant infectious disease of feedlot cattle in Australia. BRDC causes economic loss due to morbidity, mortality, loss of feed resources, medication purchases, increased time on feed and associated labor costs. BRDC has a complicated etiology with at least four viral and three bacterial species along with environmental conditions predisposing an animal to the illness.

The four viruses associated with BRDC are bovine herpesvirus 1 (BoHV-1), bovine viral diarrhea virus (BVDV or bovine pestivirus), bovine parainfluenza 3 virus and bovine respiratory syncytial virus. Serological surveys have shown that all of these viruses infect feedlot cattle in Australia. Three bacterial species, *Pasteurella mutocida, Manhiemia haemolytica* and *Haemophilus somnus*, have also been implicated in BRDC.

In North America and in Europe, both live and killed vaccines have been used to control diseases caused by BoHV-1. These vaccines are based on different genotypes of BoHV-1 to that found in Australia. North American and European BoHV-1 strains are generally classified into the subgroup 1.1 while Australian strains form the subgroup 1.2. The BoHV-1.1 viruses cause a more severe clinical disease compared to the BoHV-1.2 viruses. The exact molecular mechanism for this difference in phenotype is unknown.

BoHV-1 is a virus of the family Herpesviridae that causes several diseases worldwide in cattle, including rhinotracheitis, vaginitis, balanoposthitis, abortion, conjunctivitis and enteritis. BoHV-1 is also a contributing factor in shipping fever. It is spread through sexual contact, artificial insemination and aerosol transmission. Like other herpesviruses, BoHV-1 causes a lifelong latent infection and shedding of the virus. The sciatic nerve and trigeminal nerve are the sites of latency.

The respiratory disease caused by BoHV-1 is commonly known as infectious bovine rhibotracheitis. Symptoms include fever, discharge from the nose, cough, difficulty in breathing and loss of appetite. Ulcers commonly occur in the mouth and nose. Mortality rates may reach 10 percent. The genital disease causes infectious pustular vulvovaginitis in cows and infectious balanoposthitis in bulls. Symptoms include fever, depression, loss of appetite, painful urination, a swollen vulva with pustules and discharge in cows and pain on sexual contact in bulls. In both cases, lesions usually resolve within two weeks. Abortion and stillbirths can occur one to three months post infection. BoHV-1 also causes a generalized disease in newborn calves, characterized by enteritis and death.

Similarly, BVDV is a disease of cattle which reduces productivity and increases mortality. It is caused by a pestivirus from the family Flaviviridae. Pestiviruses have the ability to establish persistent infection during pregnancy. Persistent infection with pestiviruses often goes unnoticed. BVDV also frequently undergoes non-homologous RNA recombination leading to the appearance of genetically distinct viruses that are lethal to the host.

Clinical signs of mucosal erosions and diarrhea which occur in the acute form of bovine viral diarrhea have a significant effect on those animals infected, but much more costly are animals which are persistently infected. Typically, such animals fail to reach their genetic potential, exhibiting decreased weight gain, increased disease susceptibility and reduced fertility. They shed the virus causing reproductive loss in the unimmunized animals in the herd.

Cows that are exposed to the cytopathic variant of BVDV (45-125 days gestation) will typically abort the fetus. Earlier exposure to either variant leads to early embryonic death. Exposure between days 125-175 days of gestation leads to birth defects (such as ocular defects and hydrocephalus) and exposure at greater than 175 days will typically lead to the calf being fully immune at birth.

Therefore, as a consequence of the severity of BRDC and the significant effect on the livestock industry improvements in vaccination are required. Attenuated viruses give better protection than inactivated viruses because they present more viral antigens to the immune system of the host. Another important advantage of the attenuated virus is the potential to administer it intranasally, i.e. at the site where the first multiplication of the wild-type virus occurs after infection.

It has long been recognized that the antigenic variability of BVDV makes it a difficult virus against which to vaccinate. There are two approaches which can be taken for BVDV specific vaccination. One is the induction of neutralizing antibodies which prevent the target virus from infecting cells. The second is the induction of cell-mediated immunity (CMI) which targets virus infected cells for destruction, thus reducing the effects of a viral infection. The major neutralizing epitopes of BVDV are the structural glycoproteins and as a result of immune selection, these proteins are also the most variable. Thus, designing a vaccine based on the glycoproteins requires the inclusion of the most common antigenic types. The non-structural proteins of BVDV are generally more conserved as they have a specific enzyme function which limits the variation in the protein sequences that can occur.

For a proper BRDC control program, it is necessary to have an efficacious and safe vaccine that can be distinguished from the wild-type virus. Previously developed vaccines using BoHV-1 were constructed with deletions to glycoproteins and/or comprised a thymidine kinase deletion mutant. There have been problems with these vaccines as the thymidine kinase gene is involved in viral replication and less replication can lead to less protection due to lower levels of glycoproteins which are involved in the generation of humoral immunity.

There is a need to develop improved and more efficacious vaccines which enable control of BRDC and particular pathogens associated therewith.

SUMMARY

Nucleotide and amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A summary of the sequence identifiers is provided in Table 1. A sequence listing is provided after the claims.

Bovine respiratory disease complex (BRDC) represents a significant disease risk for bovine animals, especially those maintained in confined environments such as feed lots and dairy facilities. Infection by pathogenic agents which are associated with BRDC can spread quickly and can result in significant, morbidity, mortality and loss of production. Taught herein is an improved vaccine carrier comprising the genome from a low virulence strain of BoHV-1 modified to carry genetic material encoding one or more antigens from bovine pathogens.

Accordingly, enabled herein is a vaccine against at least one antigen from a bovine pathogen, the vaccine comprising a bovine herpes virus-1 (BoHV-1) genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes.

The vaccine has the capacity to be multivalent in respect of stimulating an immune response to BoHV-1 as well as the antigen associated with another bovine pathogen such as BVDV, *Mycoplasma, Pasteurella, Manhiemia* and *Haemophilus*. Examples of BVDV antigens include glycoproteins E0 and E2.

In an, embodiment, the heterologous genetic material is introduced using an inducible recombination system such as GET recombination.

Another aspect taught herein is a method for vaccinating a bovine animal against at least one antigen from a bovine pathogen, the method comprising administering to the bovine animal a humoral immunity-inducing or cell-mediated immunity-inducing effective amount of a BoHV-1 genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes.

Enabled herein is a method of producing a vaccine against at least one antigen from a bovine pathogen, the method comprising:

(i) incorporating a BoHV-1 genome from a low virulence BoHV-1 into a bacterial artificial chromosome (BAC) vector to form a BoHV-1 pre-vector BAC construct;

(ii) inserting genetic material encoding the at least one antigen into the BoHV-1 pre-vector BAC construct via an inducible recombination system to generate a recombinant BoHV-1-BAC (rBoHV-1-BAC) vector;

(iii) transforming and amplifying the rBoHV-1-BAC vector in a bacterial host; and (iv) purifying and isolating the rBoHV-1-BAC vector from the bacterial host and formulating the vector into a vaccine composition.

A method is also provided for vaccinating against bovine respiratory disease complex (BRDC) in cattle, the method comprising administering to the cattle a humoral immunity-inducing or cell-mediated immunity-inducing effective amount of a bovine herpes virus-1 (BoHV-1) genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes.

The present disclosure enables a use of a BoHV-1 genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes in the manufacture of a medicament in the vaccination of cattle against a bovine pathogen.

Enabled herein is a method of producing a vaccine against at least one antigen from a bovine pathogen, the method comprising:

(i) incorporating a BoHV-1 genome from a low virulence BoHV-1 into a bacterial artificial chromosome (BAC) vector to form a BoHV-1 pre-vector BAC construct;

(ii) inserting genetic material encoding the at least one antigen into the BoHV-1 pre-vector BAC construct via an inducible recombination system to generate a recombinant BoHV-1-BAC (rBoHV-1-BAC) vector;

(iii) transforming and amplifying the rBoHV-1-BAC vector in a bacterial host; and (iv) purifying and isolating the rBoHV-1-BAC vector from the bacterial host and formulating the vector into a vaccine composition.

A BoHV-1 genome from a low virulence BoHV-1 which when expressed produces an antigen to which an immune response is capable of being generated, the BoHV-1 genome further comprising genetic material encoding at least one other antigen heterologous to BoHV-1 inserted between two converging BoHV-1 genes wherein the insertion does not substantially down-regulate expression of the BoHV-1 genes and wherein the heterologous antigen induces an immune response.

Hence, taught herein is a vaccine vector comprising a BoHV-1 genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes.

A polyvalent vaccine vector is enabled herein comprising:

(1) a first valency comprising a BoHV-1 genome from a low virulence BoHV-1; and (2) a second valency comprising genetic material encoding at least one antigen which is heterologous to the BoHV-1 inserted between two converging BoHV-1 genes wherein the insertion does not substantially down-regulate expression of the BoHV-1 genes;

wherein the first and second valencies produce two or more antigens to which an immune response is generated in a bovine host.

Further enabled herein is a BoHV-1 vaccine vector comprising a BoHV-1 genome derived from BoHV-1 strain V155 having heterologous genetic material encoding at least one antigen from a bovine pathogen inserted into a site on the BoHV-1 genome selected from nucleotides 16600 to 16700; 22400 to 22500; 40,700 to 40,800; 58,000 to 59,000; 67,000 to 68,000; 74,000 to 76,000; 84,000 to 85,000; 90,000 to 91,000; and 96,000 to 97,000 of BoHV-1 reference sequence GenBank Accession No. AJ004801 or at a functionally equivalent site in another BoHV-1. For examples, refer to Table 2.

Pharmaceutical compositions, treatment and vaccination protocols are also taught the present disclosure as are business methods for management of confined or herded bovine animals.

A summary of insertion sites into the BoHV-1 genome between converging genes is provided in Table 2. Sequence co-ordinates refer to the BoHV-1 reference sequence deposited with GenBank Accession No. AJ004801.

TABLE 1

Summary of sequence identifiers

| SEQUENCE ID NO: | DESCRIPTION |
|---|---|
| 1 | Nucleotide sequence of Tkleft 5' primer |
| 2 | Nucleotide sequence of Tkleft 3' primer |
| 3 | Nucleotide sequence of Tkright 5' primer |
| 4 | Nucleotide sequence of Tkright 3' primer |
| 5 | Nucleotide sequence of ChloramF primer |
| 6 | Nucleotide sequence of ChloramR primer |
| 7 | Nucleotide sequence of gE-KanF primer |
| 8 | Nucleotide sequence of gE-KanR primer |
| 9 | Nucleotide sequence of BHV1.3 primer |
| 10 | Nucleotide sequence of BHV1.6 primer |
| 11 | Nucleotide sequence of KanR fwd primer |
| 12 | Nucleotide sequence of KanR rev primer |

TABLE 2

List of insertion sites[1] into the bovine herpesvirus 1 (BoHV-1) genome between converging genes

| Insertion Site | Start | End | Comments |
|---|---|---|---|
| Insertion Site 1 | 16600 | 16612 | Convergent genes UL46 & UL44 |
| Insertion Site 2 | 22449 | 22493 | Convergent genes UL41 & UL40 |
| Insertion Site 3 | 40734 | 40768 | Convergent genes UL36 & UL35 |
| Insertion Site 4 | 58229 | 58563 | Convergent genes UL27 & UL26 |
| Insertion Site 5 | 67037 | 67091 | Convergent genes UL22 & UL21 |
| Insertion Site 6 | 74994 | 75041 | Convergent genes UL19 & UL15 |
| Insertion Site 7 | 84496 | 84528 | Convergent genes UL11 & UL10 |
| Insertion Site 8 | 90732 | 90760 | Convergent genes UL8 & UL7 |
| Insertion Site 9 | 96870 | 96882 | Convergent genes UL4 & UL3.6 |

[1]Sequence co-ordinates refer to the BoHV-1 reference sequence with GenBank Accession AJ004801 or its equivalent

BRIEF DESCRIPTION OF THE FIGURES

FIGS. 1A through C are graphical representations showing a comparison of the virus yield of various mammalian-derived cell-lines infected with either parent Bovine herpesvirus-1 or recombinant Bovine herpesvirus carry glycoprotein E2 from bovine viral diarrhea virus at 24 hrs post-infection. (A) Cells of primate origin; (B) Cells of bovine origin; (C) Cells of rabbit and small ruminant origin. Yield of virus was determined by real-time PCR amplification performed in triplicate.

DETAILED DESCRIPTION

Figure 1C:
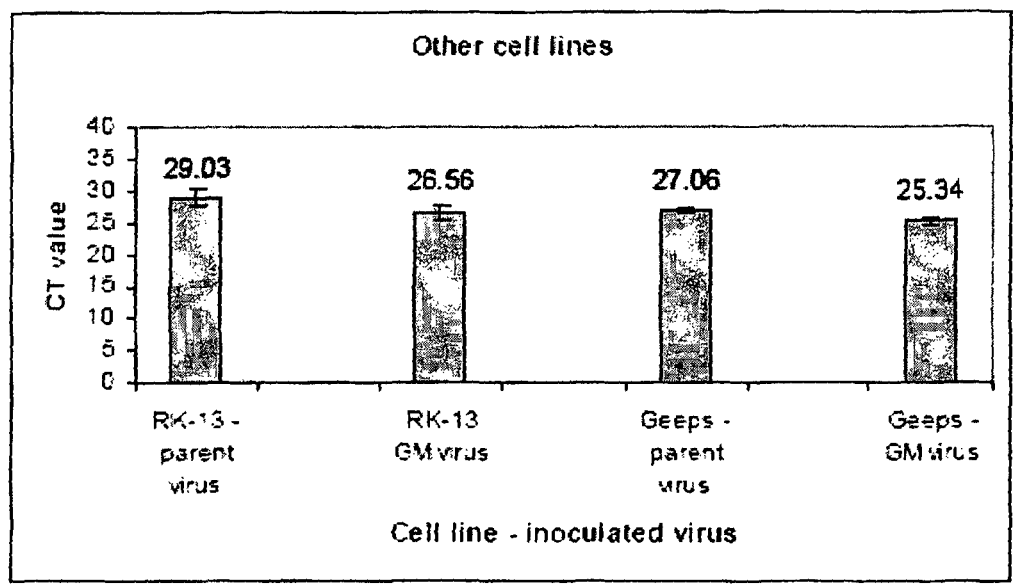

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a virus" includes a single virus, as well as two or more viruses; reference to "an antigen" includes a single antigen, as well as two or more antigens; reference to "the disclosure" includes a single or multiple aspects taught therein.

The present disclosure teaches a recombinant vaccine vector in the form of BoHV-1 from a low virulence strain of the virus. In an embodiment, the low virulence strain is referred to as BoHV-1 V155 (Snowden (1964) *Australian Veterinary Journal* 40:277-288). The recombinant vaccine vector is used as a vehicle to express proteins heterologous to BoHV-1 from bovine pathogens to which an immune response is sought. The genome portion of the BoHV-1 vector itself may also express proteins which induce an anti-BoHV-1 immune response. The immune response in bovine animals is regarded, in an embodiment, as a protective immune response in that the immune response targets the protein on or produced by a pathogen and this facilitates a reduction in infection, colonization and/or symptoms of disease and/or transmission of pathogens and/or outcomes of infection such as morbidity or mortality. The immune response may be humoral and/or cell-mediated.

In an embodiment, the BoHV-1 vector is genetically manipulated to insert genes from a bovine pathogen in between convergent genes on the BoHV-1 genome. The insertion does not, in an embodiment, substantially decrease expression of the two flanking BoHV-1 genes nor any other gene in the BoHV-1 genome. Upon infection of cells of a bovine animal with the recombinant vaccine vector, the pathogen gene(s) is/are expressed to form a protein antigen(s) and an immune response elicited against the one or more pathogen antigens. As indicated above, the BoHV-1 vector itself provides a target for immunological stimulation against BoHV-1. Hence, the present disclosure teaches the facilitation of a dual vaccine approach based on the stimulation of an immune response against BoHV-1 and an immune response against a heterologous protein genetically engineered to be expressed by the BoHV-1 vaccine vector.

Accordingly, enabled herein is a vaccine against at least one antigen from a bovine pathogen, the vaccine comprising a BoHV-1 genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes.

The vaccine enables expression of the heterologous antigen to facilitate the stimulation of an immune response against the antigen. In addition, the BoHV-1 vector itself may facilitate an immune response to a BoHV-1 protein. The use of a low virulence BoHV-1 rather than an inactivated or attenuated strain improves its ability to infect, replicate and produce a non-pathogenic infection and an effective immune response against BoHV-1 and any heterologous antigens.

Taught herein is a multivalent vaccine against two or more antigens from a bovine pathogen, the vaccine comprising a BoHV-1 genome from a low virulence BoHV-1 which when expressed produces an antigen to which an immune response is generated, the BoHV-1 genome further comprising genetic material encoding at least one other antigen heterologous to BoHV-1 inserted between two converging BoHV-1 genes wherein the insertion does not substantially down-regulate expression of the BoHV-1 genes and wherein the heterologous antigen induces an immune response.

The terms "multivalent" and "polyvalent" may be used interchangeably to describe this aspect enabled herein.

The vaccine taught herein is also considered a vaccine vector.

Accordingly, another aspect enabled herein is a vaccine vector comprising a BoHV-1 genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes.

Another aspect enabled herein is a polyvalent vaccine vector comprising:

(1) a first valency comprising a BoHV-1 genome from a low virulence BoHV-1; and (2) a second valency comprising genetic material encoding at least one antigen which is heterologous to the BoHV-1 inserted between two converging BoHV-1 genes wherein the insertion does not substantially down-regulate expression of the BoHV-1 genes;

wherein the first and second valencies produce two or more antigens to which an immune response is generated in a bovine host.

The term "substantially" in relation to the down-regulation means that there is either no down-regulation of expression or there is only a minor reduction in expression. By "minor" means that from a functional perspective, any change in expression does not adversely affect the functioning of the virus.

As indicated above, the "immune response" may be a humoral immune response and/or a cell-mediated immune response.

The vaccine enabled herein permits treatment or prophylaxis of bovine respiratory disease complex (BRDC) which is a particularly prevalent in disease in lot or herded cattle. By "lot cattle" includes cattle confined for feeding, rearing or dairying purposes. BRDC is a multi-factorial disease. Typically, a bovine animal is infected with one or more of BoHV-1, BVDV, Bovine parainfluenza 3 and/or Bovine respiratory syncytial virus. This often leads to secondary viral or microbial infection and results in conditions such as pneumonia.

Microbial pathogens contemplated herein include *Mycoplasma* sp, *Salmonella* sp, *Pasteurella* sp, *Manhiemia* sp and *Haemophilus* sp such as *Mycoplasma bovis, Pasteurella multocida, Manhiemia haemolytica* and *Haemophilus somnus*. Genetic material encoding antigens from any or all of these or other bacteria may be used in the BoHV-1 vaccine vector. BVDV antigens include glycoproteins E0 and E2.

Accordingly, the instant disclosure enables a method of vaccinating a bovine animal against at least one antigen from a bovine pathogen, the method comprising administering to the bovine animal, a humoral immunity-inducing or cell-mediated immunity-inducing effective amount of a BoHV-1 genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes.

The present disclosure teaches a method for vaccinating against BRDC in cattle, the method comprising administering to the cattle, a humoral immunity-inducing or cell-mediated immunity-inducing effective amount of a BoHV-1 genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes.

Genetic manipulation of the BoHV-1 vaccine vector to insert heterologous nucleic acid material is generally by an inducible recombination system. In an embodiment, the inducible recombination system is GET recombination which utilizes transient expression of recE and recT to enable homologous recombination in *Escherichia coli* (see Orford et al. *Nucleic Acids Research* 28 (18):e84; Mahoney et al. (2002) *Journal of Virology* 76 (13):6660-6668; Narayanan et al. (1999) *Gene therapy* 6:442-447; Schumacher et al. (2000) *Journal of Virology* 74:11088-11098).

In an embodiment, the heterologous genetic material is inserted between the polyadenylation signals of two converging genes at a site selected from 16600 to 16700 and 22400 to 22500 of BoHV-1 reference sequence GenBank Accession No. AJ004801 or at a functionally equivalent site in another BoHV-1. In an embodiment, the heterologous genetic material is inserted at a site selected from between nucleotides 16600 to 16700 and 22400 to 22493 based on sequence coordinates of BoHV-1 reference sequence GenBank Accession No. AJ004801 or its equivalent. Reference to "16600 to 16700" includes 16600, 16601, 16602, 16603, 16604, 16605, 16606, 16607, 16608, 16609, 16610, 16611, 16612, 16613, 16614, 16615, 16616, 16617, 16618, 16619, 16620, 16621, 16622, 16623, 16624, 16625, 16626, 16627, 16628, 16629, 16630, 16631, 16632, 16633, 16634, 16635, 16636, 16637, 16638, 16639, 16640, 16641, 16642, 16643, 16644, 16645, 16646, 16647, 16648, 16649, 16650, 16651, 16652, 16653, 16654, 16655, 16656, 16657, 16658, 16659, 16660, 16661, 16662, 16663, 16664, 16665, 16667, 16668, 16669, 16670, 16671, 16672, 16673, 16674, 16675, 16676, 16677, 16678, 16679, 16680, 16681, 16682, 16683, 16684, 16685, 16686, 16687, 16688, 16689, 16690, 16691, 16692, 16693, 16694, 16695, 16696, 16697, 16698, 16699 and 16700. Reference to "22400 to 22500" includes 22400, 22401, 22402, 22403, 22404, 22405, 22406, 22407, 22408, 22409, 22410, 22411, 22412, 22413, 22414, 22415, 22416, 22417, 22418, 22419, 22420, 22421, 22422, 22423, 22424, 22425, 22426, 22427, 22428, 22429, 22430, 22431, 22432, 22433, 22434, 22435, 22436, 22437, 22438, 22439, 22440, 22441, 22442, 22443, 22444, 22445, 22446, 22447, 22448, 22449, 22450, 22451, 22452, 22453, 22454, 22455, 22456, 22457, 22458, 22459, 22460, 22461, 22462, 22463, 22464, 22465, 22466, 22467, 22468, 22469, 22470, 22471, 22472, 22473, 22474, 22475, 22476, 22477, 22478, 22479, 22480, 22481, 22482, 22483, 22484, 22485, 22486, 22487, 22488, 22489, 22490, 22491, 22492, 22493, 22494, 22495, 22496, 22497, 22498, 22499 and 22500.

Other sites include within the range 40,700 to 40,800; which encompasses sites 40,700, 40,701, 40,702, 40,703, 40,704, 40,705, 40,706, 40,707, 40,708, 40,709, 40,710, 40,711, 40,712, 40,713, 40,714, 40,715, 40,716, 40,717, 40,718, 40,719, 40,720, 40,721, 40,722, 40,723, 40,724, 40,725, 40,726, 40,727, 40,728, 40,729, 40,730, 40,731, 40,732, 40,733, 40,734, 40,735, 40,736, 40,737, 40,738, 40,739, 40,740, 40,741, 40,742, 40,743, 40,744, 40,745, 40,746, 40,747, 40,748, 40,749, 40,750, 40,751, 40,752, 40,753, 40,754, 40,755, 40,756, 40,757, 40,758, 40,759, 40,760, 40,761, 40,762, 40,763, 40,764, 40,765, 40,766, 40,767, 40,768, 40,769, 40,770, 40,771, 40,772, 40,773, 40,774, 40,775, 40,776, 40,777, 40,778, 40,779, 40,780, 40,781, 40,782, 40,783, 40,784, 40,785, 40,786, 40,787, 40,788, 40,789, 40,790, 40,791, 40,792, 40,793, 40,794, 40,795, 40,796, 40,797, 40,798, 40,799, 40,800, 58,000 to 59,000 include 58,001, 58,002, 58,003, 58,004, 58,005, 58,006, 58,007, 58,008, 58,009, 58,010, 58,011, 58,012, 58,013, 58,014, 58,015, 58,016, 58,017, 58,018, 58,019, 58,020, 58,021, 58,022, 58,023, 58,024, 58,025, 58,026, 58,027, 58,028, 58,029, 58,030, 58,031, 58,032, 58,033, 58,034, 58,035, 58,036, 58,037, 58,038, 58,039, 58,040, 58,041, 58,042, 58,043, 58,044, 58,045, 58,046, 58,047, 58,048, 58,049, 58,050, 58,051, 58,052, 58,053, 58,054, 58,055, 58,056, 58,057, 58,058, 58,059, 58,060, 58,061, 58,062, 58,063, 58,064, 58,065, 58,066, 58,067, 58,068, 58,069, 58,070, 58,071, 58,072, 58,073, 58,074, 58,075, 58,076, 58,077, 58,078, 58,079, 58,080, 58,081, 58,082, 58,083, 58,084, 58,085, 58,086, 58,087, 58,088, 58,089, 58,090, 58,091, 58,092, 58,093, 58,094, 58,095, 58,096, 58,097, 58,098, 58,099, 58,100, 58,101, 58,102, 58,103, 58,104, 58,105, 58,106, 58,107, 58,110, 58,111, 58,112, 58,113, 58,114, 58,115, 58,116, 58,117, 58,118, 58,119, 58,120, 58,121, 58,122, 58,123, 58,124, 58,125, 58,126, 58,127, 58,128, 58,129, 58,130, 58,131, 58,132, 58,133, 58,134, 58,135, 58,136, 58,137, 58,138, 58,139, 58,140, 58,141, 58,142, 58,143, 58,144, 58,145, 58,146, 58,147, 58,148, 58,149, 58,150, 58,151, 58,152, 58,153, 58,154, 58,155, 58,156, 58,157, 58,158, 58,159, 58,160, 58,161, 58,162, 58,163, 58,164, 58,165, 58,166, 58,167, 58,168, 58,169, 58,170, 58,171, 58,172, 58,173, 58,174, 58,175, 58,176, 58,177, 58,178, 58,179, 58,180, 58,181, 58,182, 58,183, 58,184, 58,185, 58,186, 58,187, 58,188, 58,189, 58,190, 58,191, 58,192, 58,193, 58,194, 58,195, 58,196, 58,197, 58,198, 58,199, 58,200, 58,201, 58,202, 58,203, 58,204, 58,205, 58,206, 58,207, 58,208, 58,209, 58,210, 58,211, 58,212, 58,213, 58,214, 58,215, 58,216, 58,217, 58,218, 58,219, 58,220, 58,221, 58,222, 58,223, 58,224, 58,225, 58,226, 58,227, 58,228, 58,229, 58,230, 58,231, 58,232, 58,233, 58,234, 58,235, 58,236, 58,237, 58,238, 58,239, 58,240, 58,241, 58,242, 58,243, 58,244, 58,245, 58,246, 58,247, 58,248, 58,249, 58,250, 58,251, 58,252, 58,253, 58,254, 58,255, 58,256, 58,257, 58,258, 58,259, 58,260, 58,261, 58,262, 58,263, 58,264, 58,265, 58,266, 58,267, 58,268, 58,269, 58,270, 58,271, 58,272, 58,273, 58,274, 58,275, 58,276, 58,277, 58,278, 58,279, 58,280, 58,281, 58,282, 58,283, 58,284, 58,285, 58,286, 58,287, 58,288, 58,289, 58,290, 58,291, 58,292, 58,293, 58,294, 58,295, 58,296, 58,297, 58,298, 58,299, 58,300, 58,301, 58,302, 58,303, 58,304, 58,305, 58,306, 58,307, 58,308, 58,309, 58,310, 58,311, 58,312, 58,313, 58,314, 58,315, 58,316, 58,317, 58,318, 58,319, 58,320, 58,321, 58,322, 58,323, 58,324, 58,325, 58,326, 58,327, 58,328, 58,329, 58,330, 58,331, 58,332, 58,333, 58,334, 58,335, 58,336, 58,337, 58,338, 58,339, 58,340, 58,341, 58,342, 58,343, 58,344, 58,345, 58,346, 58,347, 58,348, 58,349, 58,350, 58,351, 58,352, 58,353, 58,354, 58,355, 58,356, 58,357, 58,358, 58,359, 58,360, 58,361, 58,362, 58,363, 58,364, 58,365, 58,366, 58,367, 58,368, 58,369, 58,370, 58,371, 58,372, 58,373, 58,374, 58,375, 58,376, 58,377, 58,378, 58,379, 58,380, 58,381, 58,382, 58,383, 58,384, 58,385, 58,386, 58,387, 58,388, 58,389, 58,390, 58,391, 58,392, 58,393, 58,394, 58,395, 58,396, 58,397, 58,398, 58,399, 58,400, 58,401, 58,402, 58,403, 58,404, 58,405, 58,406, 58,407, 58,408, 58,409, 58,410, 58, 58,411, 58,412, 58,413, 58,414, 58,415, 58,416, 58,417, 58,418, 58,419, 58,420, 58,421, 58,422, 58,423, 58,424, 58,425, 58,426, 58,427, 58,428, 58,429, 58,430, 58,431, 58,432, 58,433, 58,434, 58,435, 58,436, 58,437, 58,438, 58,439, 58,440, 58,441, 58,442, 58,443, 58,444, 58,445, 58,446, 58,447, 58,448, 58,449, 58,450, 58,451, 58,452, 58,453, 58,454, 58,455, 58,456, 58,457, 58,458, 58,459, 58,460, 58,461, 58,462, 58,463, 58,464, 58,465, 58,466, 58,467, 58,468, 58,469, 58,470, 58,471, 58,472, 58,473, 58,474, 58,475, 58,476, 58,477, 58,478, 58,479, 58,480, 58,481, 58,482, 58,483, 58,484, 58,485, 58,486, 58,487, 58,488, 58,489, 58,490, 58,491, 58,492, 58,493, 58,494, 58,495, 58,496, 58,497, 58,498, 58,499, 58,500, 58,501, 58,502, 58,503, 58,504, 58,505, 58,506, 58,507, 58,508, 58,509, 58,510, 58,511, 58,512, 58,513, 58,514, 58,515, 58,516, 58,517, 58,518, 58,519, 58,520, 58,521, 58,522, 58,523, 58,524, 58,525, 58,526, 58,527, 58,528, 58,529, 58,530, 58,531, 58,532, 58,533, 58,534, 58,535, 58,536, 58,537, 58,538, 58,539, 58,540, 58,541, 58,542, 58,543, 58,544, 58,545, 58,546, 58,547, 58,548, 58,549, 58,550, 58,551, 58,552, 58,553, 58,554, 58,555, 58,556, 58,557, 58,558, 58,559, 58,560, 58,561, 58,562, 58,563, 58,564, 58,565, 58,566, 58,567, 58,568, 58,569, 58,570, 58,571, 58,572, 58,573, 58,574, 58,575, 58,576, 58,577, 58,578, 58,579, 58,580, 58,581, 58,582, 58,583, 58,584, 58,585, 58,586, 58,587, 58,588, 58,589, 58,590, 58,591, 58,592, 58,593, 58,594, 58,595, 58,596, 58,597, 58,598, 58,599, 58,600, 58,601, 58,602, 58,603, 58,604, 58,605, 58,606, 58,607, 58,608, 58,609, 58,610, 58,611, 58,612, 58,613, 58,614, 58,615, 58,616, 58,617, 58,618, 58,619, 58,620, 58,621, 58,622, 58,623, 58,624, 58,625, 58,626, 58,627, 58,628, 58,629, 58,630, 58,631, 58,632, 58,633, 58,634, 58,635, 58,636, 58,637, 58,638, 58,639, 58,640, 58,641, 58,642, 58,643, 58,644, 58,645, 58,646, 58,647, 58,648, 58,649, 58,650, 58,651, 58,652, 58,653, 58,654, 58,655, 58,656, 58,657, 58,658, 58,659, 58,660, 58,661, 58,662, 58,663, 58,664, 58,665, 58,666, 58,667, 58,668, 58,669, 58,670, 58,671, 58,672, 58,673, 58,674, 58,675, 58,676, 58,677, 58,678, 58,679, 58,680, 58,681, 58,682, 58,683, 58,684, 58,685, 58,686, 58,687, 58,688, 58,689, 58,690, 58,691, 58,692, 58,693, 58,694, 58,695, 58,696, 58,697, 58,698, 58,699, 58,700, 58,701, 58,702, 58,703, 58,704, 58,705, 58,706, 58,707, 58,708, 58,709, 58,710, 58,711, 58,712, 58,713, 58,714, 58,715, 58,716, 58,717, 58,718, 58,719, 58,720, 58,721, 58,722, 58,723, 58,724, 58,725, 58,726, 58,727, 58,728, 58,729, 58,730, 58,731, 58,732, 58,733, 58,734, 58,735, 58,736, 58,737, 58,738, 58,739, 58,740, 58,741, 58,742, 58,743, 58,744, 58,745, 58,746, 58,747, 58,748, 58,749, 58,750, 58,751, 58,752, 58,753, 58,754, 58,755, 58,756, 58,757, 58,758, 58,759, 58,760, 58,761, 58,762, 58,763, 58,764, 58,765, 58,766, 58,767, 58,768, 58,769, 58,770, 58,771, 58,772, 58,773, 58,774, 58,775, 58,776, 58,777, 58,778, 58,779, 58,780, 58,781, 58,782, 58,783, 58,784, 58,785, 58,786, 58,787, 58,788, 58,789, 58,790, 58,791, 58,792, 58,793, 58,794, 58,795, 58,796, 58,797, 58,798, 58,799, 58,800, 58,801, 58,802, 58,803, 58,804, 58,805, 58,806, 58,807, 58,808, 58,809, 58,810, 58,811, 58,812, 58,813, 58,814, 58,815, 58,816, 58,817, 58,818, 58,819, 58,820, 58,821, 58,822, 58,823, 58,824, 58,825, 58,826, 58,827, 58,828, 58,829, 58,830, 58,831, 58,832, 58,833, 58,834, 58,835, 58,836, 58,837, 58,838, 58,839, 58,840, 58,841, 58,842, 58,843, 58,844, 58,845, 58,846, 58,847, 58,848, 58,849, 58,850, 58,851, 58,852, 58,853, 58,854, 58,855, 58,856, 58,857, 58,858, 58,859, 58,860, 58,861, 58,862, 58,863, 58,864, 58,865, 58,866, 58,867, 58,868, 58,869, 58,870, 58,871, 58,872, 58,873, 58,874, 58,875, 58,876, 58,877, 58,878, 58,879, 58,880, 58,881, 58,882, 58,883, 58,884, 58,885, 58,886, 58,887, 58,888, 58,889, 58,890, 58,891, 58,892, 58,893, 58,894, 58,895, 58,896, 58,897, 58,898, 58,899, 58,900, 58,901, 58,902, 58,903, 58,904, 58,905, 58,906, 58,907, 58,908, 58,909, 58,910, 58,911, 58,912, 58,913, 58,914, 58,915, 58,916, 58,917, 58,918, 58,919, 58,920, 58,921, 58,922, 58,923, 58,924, 58,925, 58,926, 58,927, 58,928, 58,929, 58,930, 58,931, 58,932, 58,933, 58,934, 58,935, 58,936, 58,937, 58,938, 58,939, 58,940, 58,941, 58,942, 58,943, 58,944, 58,945, 58,946, 58,947, 58,948, 58,949, 58,950, 58,951, 58,952, 58,953, 58,954, 58,955, 58,956, 58,957, 58,958, 58,959, 58,960, 58,961, 58,962, 58,963, 58,964, 58,965, 58,966, 58,967, 58,968, 58,969, 58,970, 58,971, 58,972, 58,973, 58,974, 58,975, 58,976, 58,977, 58,978, 58,979, 58,980, 58,981, 58,982, 58,983, 58,984, 58,985, 58,986, 58,987, 58,988, 58,989, 58,990, 58,991, 58,992, 58,993, 58,994, 58,995, 58,996, 58,997, 58,998, 58,999 or 59,000, 67,000 to 68,000 include 67,001, 67,002, 67,003, 67,004, 67,005, 67,006, 67,007, 67,008, 67,009, 67,010, 67,011, 67,012, 67,013, 67,014, 67,015, 67,016, 67,017, 67,018, 67,019, 67,020, 67,021, 67,022, 67,023, 67,024, 67,025, 67,026, 67,027, 67,028, 67,029, 67,030, 67,031, 67,032, 67,033, 67,034, 67,035, 67,036, 67,037, 67,038, 67,039, 67,040, 67,041, 67,042, 67,043, 67,044, 67,045, 67,046, 67,047, 67,048, 67,049, 67,050, 67,051, 67,052, 67,053, 67,054, 67,055, 67,056, 67,057, 67,067, 67,059, 67,060, 67,061, 67,062, 67,063, 67,064, 67,065, 67,066, 67,067, 67,068, 67,069, 67,070, 67,071, 67,072, 67,073, 67,074, 67,075, 67,076, 67,077, 67,078, 67,079, 67,080, 67,081, 67,082, 67,083, 67,084, 67,085, 67,086, 67,087, 67,088, 67,089, 67,090, 67,091, 67,092, 67,093, 67,094, 67,095, 67,096, 67,097, 67,098, 67,099, 67,100, 67,101, 67,102, 67,103, 67,104, 67,105, 67,106, 67,107, 67,110, 67,111, 67,112, 67,113, 67,114, 67,115, 67,116, 67,117, 67,118, 67,119, 67,120, 67,121, 67,122, 67,123, 67,124, 67,125, 67,126, 67,127, 67,128, 67,129, 67,130, 67,131, 67,132, 67,133, 67,134, 67,135, 67,136, 67,137, 67,138, 67,139, 67,140, 67,141, 67,142, 67,143, 67,144, 67,145, 67,146, 67,147, 67,148, 67,149, 67,150, 67,151, 67,152, 67,153, 67,154, 67,155, 67,156, 67,157, 67,167, 67,159, 67,160, 67,161, 67,162, 67,163, 67,164, 67,165, 67,166, 67,167, 67,168, 67,169, 67,170, 67,171, 67,172, 67,173, 67,174, 67,175, 67,176, 67,177, 67,178, 67,179, 67,180, 67,181, 67,182, 67,183, 67,184, 67,185, 67,186, 67,187, 67,188, 67,189, 67,190, 67,191, 67,192, 67,193, 67,194, 67,195, 67,196, 67,197, 67,198, 67,199, 67,200, 67,201, 67,202, 67,203, 67,204, 67,205, 67,206, 67,207, 67,208, 67,209, 67,210, 67,211, 67,212, 67,213, 67,214, 67,215, 67,216, 67,217, 67,218, 67,219, 67,220, 67,221, 67,222, 67,223, 67,224, 67,225, 67,226, 67,227, 67,228, 67,229, 67,230, 67,231, 67,232, 67,233, 67,234, 67,235, 67,236, 67,237, 67,238, 67,239, 67,240, 67,241, 67,242, 67,243, 67,244, 67,245, 67,246, 67,247, 67,248, 67,249, 67,250, 67,251, 67,252, 67,253, 67,254, 67,255, 67,256, 67,257, 67,267, 67,259, 67,260, 67,261, 67,262, 67,263, 67,264, 67,265, 67,266, 67,267, 67,268, 67,269, 67,270, 67,271, 67,272, 67,273, 67,274, 67,275, 67,276, 67,277, 67,278, 67,279, 67,280, 67,281, 67,282, 67,283, 67,284, 67,285, 67,286, 67,287, 67,288, 67,289, 67,290, 67,291, 67,292, 67,293, 67,294, 67,295, 67,296, 67,297, 67,298, 67,299, 67,300, 67,301, 67,302, 67,303, 67,304, 67,305, 67,306, 67,307, 67,308, 67,309, 67,310, 67,311, 67,312, 67,313, 67,314, 67,315, 67,316, 67,317, 67,318, 67,319, 67,320, 67,321, 67,322, 67,323, 67,324, 67,325, 67,326, 67,327, 67,328, 67,329, 67,330, 67,331, 67,332, 67,333, 67,334, 67,335, 67,336, 67,337, 67,338, 67,339, 67,340, 67,341, 67,342, 67,343, 67,344, 67,345, 67,346, 67,347, 67,348, 67,349, 67,350, 67,351, 67,352, 67,353, 67,354, 67,355, 67,356, 67,357, 67,367, 67,359, 67,360, 67,361, 67,362, 67,363, 67,364, 67,365, 67,366, 67,367, 67,368, 67,369, 67,370, 67,371, 67,372, 67,373, 67,374, 67,375, 67,376, 67,377, 67,378, 67,379, 67,380, 67,381, 67,382, 67,383, 67,384, 67,385, 67,386, 67,387, 67,388, 67,389, 67,390, 67,391, 67,392, 67,393, 67,394, 67,395, 67,396, 67,397, 67,398, 67,399, 67,400, 67,401, 67,402, 67,403, 67,404, 67,405, 67,406, 67,407, 67,408, 67,409, 67,410, 67,411, 67,412, 67,413, 67,414, 67,415, 67,416, 67,417, 67,418, 67,419, 67,420, 67,421, 67,422, 67,423, 67,424, 67,425, 67,426, 67,427, 67,428, 67,429, 67,430, 67,431, 67,432, 67,433, 67,434, 67,435, 67,436, 67,437, 67,438, 67,439, 67,440, 67,441, 67,442, 67,443, 67,444, 67,445, 67,446, 67,447, 67,448, 67,449, 67,450, 67,451, 67,452, 67,453, 67,454, 67,455, 67,456, 67,457, 67,467, 67,459, 67,460, 67,461, 67,462, 67,463, 67,464, 67,465, 67,466, 67,467, 67,468, 67,469, 67,470, 67,471, 67,472, 67,473, 67,474, 67,475, 67,476, 67,477, 67,478, 67,479, 67,480, 67,481, 67,482, 67,483, 67,484, 67,485, 67,486, 67,487, 67,488, 67,489, 67,490, 67,491, 67,492, 67,493, 67,494, 67,495, 67,496, 67,497, 67,498, 67,499, 67,500, 67,501, 67,502, 67,503, 67,504, 67,505, 67,506, 67,507, 67,508, 67,509, 67,510, 67,511, 67,512, 67,513, 67,514, 67,515, 67,516, 67,517, 67,518, 67,519, 67,520, 67,521, 67,522, 67,523, 67,524, 67,525, 67,526, 67,527, 67,528, 67,529, 67,530, 67,531, 67,532, 67,533, 67,534, 67,535, 67,536, 67,537, 67,538, 67,539, 67,540, 67,541, 67,542, 67,543, 67,544, 67,545, 67,546, 67,547, 67,548, 67,549, 67,550, 67,551, 67,552, 67,553, 67,554, 67,555, 67,556, 67,557, 67,567, 67,559, 67,560, 67,561, 67,562, 67,563, 67,564, 67,565, 67,566, 67,567, 67,568, 67,569, 67,570, 67,571, 67,572, 67,573, 67,574, 67,575, 67,576, 67,577, 67,578, 67,579, 67,580, 67,581, 67,582, 67,583, 67,584, 67,585, 67,586, 67,587, 67,588, 67,589, 67,590, 67,591, 67,592, 67,593, 67,594, 67,595, 67,596, 67,597, 67,598, 67,599, 67,600, 67,601, 67,602, 67,603, 67,604, 67,605, 67,606, 67,607, 67,608, 67,609, 67,610, 67,611, 67,612, 67,613, 67,614, 67,615, 67,616, 67,617, 67,618, 67,619, 67,620, 67,621, 67,622, 67,623, 67,624, 67,625, 67,626, 67,627, 67,628, 67,629, 67,630, 67,631, 67,632, 67,633, 67,634, 67,635, 67,636, 67,637, 67,638, 67,639, 67,640, 67,641, 67,642, 67,643, 67,644, 67,645, 67,646, 67,647, 67,648, 67,649, 67,650, 67,651, 67,652, 67,653, 67,654, 67,655, 67,656, 67,657, 67,667, 67,659, 67,660, 67,661, 67,662, 67,663, 67,664, 67,665, 67,666, 67,667, 67,668, 67,669, 67,670, 67,671, 67,672, 67,673, 67,674, 67,675, 67,676, 67,677, 67,678, 67,679, 67,680, 67,681, 67,682, 67,683, 67,684, 67,685, 67,686, 67,687, 67,688, 67,689, 67,690, 67,691, 67,692, 67,693, 67,694, 67,695, 67,696, 67,697, 67,698, 67,699, 67,700, 67,701, 67,702, 67,703, 67,704, 67,705, 67,706, 67,707, 67,708, 67,709, 67,710, 67,711, 67,712, 67,713, 67,714, 67,715, 67,716, 67,717, 67,718, 67,719, 67,720, 67,721, 67,722, 67,723, 67,724, 67,725, 67,726, 67,727, 67,728, 67,729, 67,730, 67,731, 67,732, 67,733, 67,734, 67,735, 67,736, 67,737, 67,738, 67,739, 67,740, 67,741, 67,742, 67,743, 67,744, 67,745, 67,746, 67,747, 67,748, 67,749, 67,750, 67,751, 67,752, 67,753, 67,754, 67,755, 67,756, 67,757, 67,767, 67,759, 67,760, 67,761, 67,762, 67,763, 67,764, 67,765, 67,766, 67,767, 67,768, 67,769, 67,770, 67,771, 67,772, 67,773, 67,774, 67,775, 67,776, 67,777, 67,778, 67,779, 67,780, 67,781, 67,782, 67,783, 67,784, 67,785, 67,786, 67,787, 67,788, 67,789, 67,790, 67,791, 67,792, 67,793, 67,794, 67,795, 67,796, 67,797, 67,798, 67,799, 67,800, 67,801, 67,802, 67,803, 67,804, 67,805, 67,806, 67,807, 67,808, 67,809, 67,810, 67,811, 67,812, 67,813, 67,814, 67,815, 67,816, 67,817, 67,818, 67,819, 67,820, 67,821, 67,822, 67,823, 67,824, 67,825, 67,826, 67,827, 67,828, 67,829, 67,830, 67,831, 67,832, 67,833, 67,834, 67,835, 67,836, 67,837, 67,838, 67,839, 67,840, 67,841, 67,842, 67,843, 67,844, 67,845, 67,846, 67,847, 67,848, 67,849, 67,850, 67,851, 67,852, 67,853, 67,854, 67,855, 67,856, 67,857, 67,867, 67,859, 67,860, 67,861, 67,862, 67,863, 67,864, 67,865, 67,866, 67,867, 67,868, 67,869, 67,870, 67,871, 67,872, 67,873, 67,874, 67,875, 67,876, 67,877, 67,878, 67,879, 67,880, 67,881, 67,882, 67,883, 67,884, 67,885, 67,886, 67,887, 67,888, 67,889, 67,890, 67,891, 67,892, 67,893, 67,894, 67,895, 67,896, 67,897, 67,898, 67,899, 67,900, 67,901, 67,902, 67,903, 67,904, 67,905, 67,906, 67,907, 67,908, 67,909, 67,910, 67,911, 67,912, 67,913, 67,914, 67,915, 67,916, 67,917, 67,918, 67,919, 67,920, 67,921, 67,922, 67,923, 67,924, 67,925, 67,926, 67,927, 67,928, 67,929, 67,930, 67,931, 67,932, 67,933, 67,934, 67,935, 67,936, 67,937, 67,938, 67,939, 67,940, 67,941, 67,942, 67,943, 67,944, 67,945, 67,946, 67,947, 67,948, 67,949, 67,950, 67,951, 67,952, 67,953, 67,954, 67,955, 67,956, 67,957, 67,967, 67,959, 67,960, 67,961, 67,962, 67,963, 67,964, 67,965, 67,966, 67,967, 67,968, 67,969, 67,970, 67,971, 67,972, 67,973, 67,974, 67,975, 67,976, 67,977, 67,978, 67,979, 67,980, 67,981, 67,982, 67,983, 67,984, 67,985, 67,986, 67,987, 67,988, 67,989, 67,990, 67,991, 67,992, 67,993, 67,994, 67,995, 67,996, 67,997, 67,998, 67,999 or 68,000, 74,000 to 76,000 include 74,001, 74,002, 74,003, 74,004, 74,005, 74,006, 74,007, 74,008, 74,009, 74,010, 74,011, 74,012, 74,013, 74,014, 74,015, 74,016, 74,017, 74,018, 74,019, 74,020, 74,021, 74,022, 74,023, 74,024, 74,025, 74,026, 74,027, 74,028, 74,029, 74,030, 74,031, 74,032, 74,033, 74,034, 74,035, 74,036, 74,037, 74,038, 74,039, 74,040, 74,041, 74,042, 74,043, 74,044, 74,045, 74,046, 74,047, 74,048, 74,049, 74,050, 74,051, 74,052, 74,053, 74,054, 74,055, 74,056, 74,057, 74,074, 74,059, 74,060, 74,061, 74,062, 74,063, 74,064, 74,065, 74,066, 74,074, 74,068, 74,069, 74,070, 74,071, 74,072, 74,073, 74,074, 74,075, 74,076, 74,077, 74,078, 74,079, 74,080, 74,081, 74,082, 74,083, 74,084, 74,085, 74,086, 74,087, 74,088, 74,089, 74,090, 74,091, 74,092, 74,093, 74,094, 74,095, 74,096, 74,097, 74,098, 74,099, 74,100, 74,101, 74,102, 74,103, 74,104, 74,105, 74,106, 74,107, 74,110, 74,111, 74,112, 74,113, 74,114, 74,115, 74,116, 74,117, 74,118, 74,119, 74,120, 74,121, 74,122, 74,123, 74,124, 74,125, 74,126, 74,127, 74,128, 74,129, 74,130, 74,131, 74,132, 74,133, 74,134, 74,135, 74,136, 74,137, 74,138, 74,139, 74,140, 74,141, 74,142, 74,143, 74,144, 74,145, 74,146, 74,147, 74,148, 74,149, 74,150, 74,151, 74,152, 74,153, 74,154, 74,155, 74,156, 74,157, 74,174, 74,159, 74,160, 74,161, 74,162, 74,163, 74,164, 74,165, 74,166, 74,174, 74,168, 74,169, 74,170, 74,171, 74,172, 74,173, 74,174, 74,175, 74,176, 74,177, 74,178, 74,179, 74,180, 74,181, 74,182, 74,183, 74,184, 74,185, 74,186, 74,187, 74,188, 74,189, 74,190, 74,191, 74,192, 74,193, 74,194, 74,195, 74,196, 74,197, 74,198, 74,199, 74,200, 74,201, 74,202, 74,203, 74,204, 74,205, 74,206, 74,207, 74,208, 74,209, 74,210, 74,211, 74,212, 74,213, 74,214, 74,215, 74,216, 74,217, 74,218, 74,219, 74,220, 74,221, 74,222, 74,223, 74,224, 74,225, 74,226, 74,227, 74,228, 74,229, 74,230, 74,231, 74,232, 74,233, 74,234, 74,235, 74,236, 74,237, 74,238, 74,239, 74,240, 74,241, 74,242, 74,243, 74,244, 74,245, 74,246, 74,247, 74,248, 74,249, 74,250, 74,251, 74,252, 74,253, 74,254, 74,255, 74,256, 74,257, 74,274, 74,259, 74,260, 74,261, 74,262, 74,263, 74,264, 74,265, 74,266, 74,274, 74,268, 74,269, 74,270, 74,271, 74,272, 74,273, 74,274, 74,275, 74,276, 74,277, 74,278, 74,279, 74,280, 74,281, 74,282, 74,283, 74,284, 74,285, 74,286, 74,287, 74,288, 74,289, 74,290, 74,291, 74,292, 74,293, 74,294, 74,295, 74,296, 74,297, 74,298, 74,299, 74,300, 74,301, 74,302, 74,303, 74,304, 74,305, 74,306, 74,307, 74,308, 74,309, 74,310, 74,311, 74,312, 74,313, 74,314, 74,315, 74,316, 74,317, 74,318, 74,319, 74,320, 74,321, 74,322, 74,323, 74,324, 74,325, 74,326, 74,327, 74,328, 74,329, 74,330, 74,331, 74,332, 74,333, 74,334, 74,335, 74,336, 74,337, 74,338, 74,339, 74,340, 74,341, 74,342, 74,343, 74,344, 74,345, 74,346, 74,347, 74,348, 74,349, 74,350, 74,351, 74,352, 74,353, 74,354, 74,355, 74,356, 74,357, 74,374, 74,359, 74,360, 74,361, 74,362, 74,363, 74,364, 74,365, 74,366, 74,374, 74,368, 74,369, 74,370, 74,371, 74,372, 74,373, 74,374, 74,375, 74,376, 74,377, 74,378, 74,379, 74,380, 74,381, 74,382, 74,383, 74,384, 74,385, 74,386, 74,387, 74,388, 74,389, 74,390, 74,391, 74,392, 74,393, 74,394, 74,395, 74,396, 74,397, 74,398, 74,399, 74,400, 74,401, 74,402, 74,403, 74,404, 74,405, 74,406, 74,407, 74,408, 74,409, 74,410, 74,411, 74,412, 74,413, 74,414, 74,415, 74,416, 74,417, 74,418, 74,419, 74,420, 74,421, 74,422, 74,423, 74,424, 74,425, 74,426, 74,427, 74,428, 74,429, 74,430, 74,431, 74,432, 74,433, 74,434, 74,435, 74,436, 74,437, 74,438, 74,439, 74,440, 74,441, 74,442, 74,443, 74,444, 74,445, 74,446, 74,447, 74,448, 74,449, 74,450, 74,451, 74,452, 74,453, 74,454, 74,455, 74,456, 74,457, 74,474, 74,459, 74,460, 74,461, 74,462, 74,463, 74,464, 74,465, 74,466, 74,474, 74,468, 74,469, 74,470, 74,471, 74,472, 74,473, 74,474, 74,475, 74,476, 74,477, 74,478, 74,479, 74,480, 74,481, 74,482, 74,483, 74,484, 74,485, 74,486, 74,487, 74,488, 74,489, 74,490, 74,491, 74,492, 74,493, 74,494, 74,495, 74,496, 74,497, 74,498, 74,499, 74,500, 74,501, 74,502, 74,503, 74,504, 74,505, 74,506, 74,507, 74,508, 74,509, 74,510, 74,511, 74,512, 74,513, 74,514, 74,515, 74,516, 74,517, 74,518, 74,519, 74,520, 74,521, 74,522, 74,523, 74,524, 74,525, 74,526, 74,527, 74,528, 74,529, 74,530, 74,531, 74,532, 74,533, 74,534, 74,535, 74,536, 74,537, 74,538, 74,539, 74,540, 74,541, 74,542, 74,543, 74,544, 74,545, 74,546, 74,547, 74,548, 74,549, 74,550, 74,551, 74,552, 74,553, 74,554, 74,555, 74,556, 74,557, 74,574, 74,559, 74,560, 74,561, 74,562, 74,563, 74,564, 74,565, 74,566, 74,574, 74,568, 74,569, 74,570, 74,571, 74,572, 74,573, 74,574, 74,575, 74,576, 74,577, 74,578, 74,579, 74,580, 74,581, 74,582, 74,583, 74,584, 74,585, 74,586, 74,587, 74,588, 74,589, 74,590, 74,591, 74,592, 74,593, 74,594, 74,595, 74,596, 74,597, 74,598, 74,599, 74,600, 74,601, 74,602, 74,603, 74,604, 74,605, 74,606, 74,607, 74,608, 74,609, 74,610, 74,611, 74,612, 74,613, 74,614, 74,615, 74,616, 74,617, 74,618, 74,619, 74,620, 74,621, 74,622, 74,623, 74,624, 74,625, 74,626, 74,627, 74,628, 74,629, 74,630, 74,631, 74,632, 74,633, 74,634, 74,635, 74,636, 74,637, 74,638, 74,639, 74,640, 74,641, 74,642, 74,643, 74,644, 74,645, 74,646, 74,647, 74,648, 74,649, 74,650, 74,651, 74,652, 74,653, 74,654, 74,655, 74,656, 74,657, 74,674, 74,659, 74,660, 74,661, 74,662, 74,663, 74,664, 74,665, 74,666, 74,674, 74,668, 74,669, 74,670, 74,671, 74,672, 74,673, 74,674, 74,675, 74,676, 74,677, 74,678, 74,679, 74,680, 74,681, 74,682, 74,683, 74,684, 74,685, 74,686, 74,687, 74,688, 74,689, 74,690, 74,691, 74,692, 74,693, 74,694, 74,695, 74,696, 74,697, 74,698, 74,699, 74,700, 74,701, 74,702, 74,703, 74,704, 74,705, 74,706, 74,707, 74,708, 74,709, 74,710, 74,711, 74,712, 74,713, 74,714, 74,715, 74,716, 74,717, 74,718, 74,719, 74,720, 74,721, 74,722, 74,723, 74,724, 74,725, 74,726, 74,727, 74,728, 74,729, 74,730, 74,731, 74,732, 74,733, 74,734, 74,735, 74,736, 74,737, 74,738, 74,739, 74,740, 74,741, 74,742, 74,743, 74,744, 74,745, 74,746, 74,747, 74,748, 74,749, 74,750, 74,751, 74,752, 74,753, 74,754, 74,755, 74,756, 74,757, 74,774, 74,759, 74,760, 74,761, 74,762, 74,763, 74,764, 74,765, 74,766, 74,774, 74,768, 74,769, 74,770, 74,771, 74,772, 74,773, 74,774, 74,775, 74,776, 74,777, 74,778, 74,779, 74,780, 74,781, 74,782, 74,783, 74,784, 74,785, 74,786, 74,787, 74,788, 74,789, 74,790, 74,791, 74,792, 74,793, 74,794, 74,795, 74,796, 74,797, 74,798, 74,799, 74,800, 74,801, 74,802, 74,803, 74,804, 74,805, 74,806, 74,807, 74,808, 74,809, 74,810, 74,811, 74,812, 74,813, 74,814, 74,815, 74,816, 74,817, 74,818, 74,819, 74,820, 74,821, 74,822, 74,823, 74,824, 74,825, 74,826, 74,827, 74,828, 74,829, 74,830, 74,831, 74,832, 74,833, 74,834, 74,835, 74,836, 74,837, 74,838, 74,839, 74,840, 74,841, 74,842, 74,843, 74,844, 74,845, 74,846, 74,847, 74,848, 74,849, 74,850, 74,851, 74,852, 74,853, 74,854, 74,855, 74,856, 74,857, 74,874, 74,859, 74,860, 74,861, 74,862, 74,863, 74,864, 74,865, 74,866, 74,874, 74,868, 74,869, 74,870, 74,871, 74,872, 74,873, 74,874, 74,875, 74,876, 74,877, 74,878, 74,879, 74,880, 74,881, 74,882, 74,883, 74,884, 74,885, 74,886, 74,887, 74,888, 74,889, 74,890, 74,891, 74,892, 74,893, 74,894, 74,895, 74,896, 74,897, 74,898, 74,899, 74,900, 74,901, 74,902, 74,903, 74,904, 74,905, 74,906, 74,907, 74,908, 74,909, 74,910, 74,911, 74,912, 74,913, 74,914, 74,915, 74,916, 74,917, 74,918, 74,919, 74,920, 74,921, 74,922, 74,923, 74,924, 74,925, 74,926, 74,927, 74,928, 74,929, 74,930, 74,931, 74,932, 74,933, 74,934, 74,935, 74,936, 74,937, 74,938, 74,939, 74,940, 74,941, 74,942, 74,943, 74,944, 74,945, 74,946, 74,947, 74,948, 74,949, 74,950, 74,951, 74,952, 74,953, 74,954, 74,955, 74,956, 74,957, 74,974, 74,959, 74,960, 74,961, 74,962, 74,963, 74,964, 74,965, 74,966, 74,974, 74,968, 74,969, 74,970, 74,971, 74,972, 74,973, 74,974, 74,975, 74,976, 74,977, 74,978, 74,979, 74,980, 74,981, 74,982, 74,983, 74,984, 74,985, 74,986, 74,987, 74,988, 74,989, 74,990, 74,991, 74,992, 74,993, 74,994, 74,995, 74,996, 74,997, 74,998, 74,999, 75,000, 75,001, 75,002, 75,003, 75,004, 75,005, 75,006, 75,007, 75,008, 75,009, 75,010, 75,011, 75,012, 75,013, 75,014, 75,015, 75,016, 75,017, 75,018, 75,019, 75,020, 75,021, 75,022, 75,023, 75,024, 75,025, 75,026, 75,027, 75,028, 75,029, 75,030, 75,031, 75,032, 75,033, 75,034, 75,035, 75,036, 75,037, 75,038, 75,039, 75,040, 75,041, 75,042, 75,043, 75,044, 75,045, 75,046, 75,047, 75,048, 75,049, 75,050, 75,051, 75,052, 75,053, 75,054, 75,055, 75,056, 75,057, 75,075, 75,059, 75,060, 75,061, 75,062, 75,063, 75,064, 75,065, 75,066, 75,075, 75,068, 75,069, 75,070, 75,071, 75,072, 75,073, 75,075, 75,075, 75,076, 75,077, 75,078, 75,079, 75,080, 75,081, 75,082, 75,083, 75,084, 75,085, 75,086, 75,087, 75,088, 75,089, 75,090, 75,091, 75,092, 75,093, 75,094, 75,095, 75,096, 75,097, 75,098, 75,099, 75,100, 75,101, 75,102, 75,103, 75,104, 75,105, 75,106, 75,107, 75,110, 75,111, 75,112, 75,113, 75,114, 75,115, 75,116, 75,117, 75,118, 75,119, 75,120, 75,121, 75,122, 75,123, 75,124, 75,125, 75,126, 75,127, 75,128, 75,129, 75,130, 75,131, 75,132, 75,133, 75,134, 75,135, 75,136, 75,137, 75,138, 75,139, 75,140, 75,141, 75,142, 75,143, 75,144, 75,145, 75,146, 75,147, 75,148, 75,149, 75,150, 75,151, 75,152, 75,153, 75,154, 75,155, 75,156, 75,157, 75,175, 75,159, 75,160, 75,161, 75,162, 75,163, 75,164, 75,165, 75,166, 75,175, 75,168, 75,169, 75,170, 75,171, 75,172, 75,173, 75,175, 75,175, 75,176, 75,177, 75,178, 75,179, 75,180, 75,181, 75,182, 75,183, 75,184, 75,185, 75,186, 75,187, 75,188, 75,189, 75,190, 75,191, 75,192, 75,193, 75,194, 75,195, 75,196, 75,197, 75,198, 75,199, 75,200, 75,201, 75,202, 75,203, 75,204, 75,205, 75,206, 75,207, 75,208, 75,209, 75,210, 75,211, 75,212, 75,213, 75,214, 75,215, 75,216, 75,217, 75,218, 75,219, 75,220, 75,221, 75,222, 75,223, 75,224, 75,225, 75,226, 75,227, 75,228, 75,229, 75,230, 75,231, 75,232, 75,233, 75,234, 75,235, 75,236, 75,237, 75,238, 75,239, 75,240, 75,241, 75,242, 75,243, 75,244, 75,245, 75,246, 75,247, 75,248, 75,249, 75,250, 75,251, 75,252, 75,253, 75,254, 75,255, 75,256, 75,257, 75,275, 75,259, 75,260, 75,261, 75,262, 75,263, 75,264, 75,265, 75,266, 75,275, 75,268, 75,269, 75,270, 75,271, 75,272, 75,273, 75,275, 75,275, 75,276, 75,277, 75,278, 75,279, 75,280, 75,281, 75,282, 75,283, 75,284, 75,285, 75,286, 75,287, 75,288, 75,289, 75,290, 75,291, 75,292, 75,293, 75,294, 75,295, 75,296, 75,297, 75,298, 75,299, 75,300, 75,301, 75,302, 75,303, 75,304, 75,305, 75,306, 75,307, 75,308, 75,309, 75,310, 75,311, 75,312, 75,313, 75,314, 75,315, 75,316, 75,317, 75,318, 75,319, 75,320, 75,321, 75,322, 75,323, 75,324, 75,325, 75,326, 75,327, 75,328, 75,329, 75,330, 75,331, 75,332, 75,333, 75,334, 75,335, 75,336, 75,337, 75,338, 75,339, 75,340, 75,341, 75,342, 75,343, 75,344, 75,345, 75,346, 75,347, 75,348, 75,349, 75,350, 75,351, 75,352, 75,353, 75,354, 75,355, 75,356, 75,357, 75,375, 75,359, 75,360, 75,361, 75,362, 75,363, 75,364, 75,365, 75,366, 75,375, 75,368, 75,369, 75,370, 75,371, 75,372, 75,373, 75,375, 75,375, 75,376, 75,377, 75,378, 75,379, 75,380, 75,381, 75,382, 75,383, 75,384, 75,385, 75,386, 75,387, 75,388, 75,389, 75,390, 75,391, 75,392, 75,393, 75,394, 75,395, 75,396, 75,397, 75,398, 75,399, 75,400, 75,401, 75,402, 75,403, 75,404, 75,405, 75,406, 75,407, 75,408, 75,409, 75,410, 75,411, 75,412, 75,413, 75,414, 75,415, 75,416, 75,417, 75,418, 75,419, 75,420, 75,421, 75,422, 75,423, 75,424, 75,425, 75,426, 75,427, 75,428, 75,429, 75,430, 75,431, 75,432, 75,433, 75,434, 75,435, 75,436, 75,437, 75,438, 75,439, 75,440, 75,441, 75,442, 75,443, 75,444, 75,445, 75,446, 75,447, 75,448, 75,449, 75,450, 75,451, 75,452, 75,453, 75,454, 75,455, 75,456, 75,457, 75,475, 75,459, 75,460, 75,461, 75,462, 75,463, 75,464, 75,465, 75,466, 75,475, 75,468, 75,469, 75,470, 75,471, 75,472, 75,473, 75,475, 75,475, 75,476, 75,477, 75,478, 75,479, 75,480, 75,481, 75,482, 75,483, 75,484, 75,485, 75,486, 75,487, 75,488, 75,489, 75,490, 75,491, 75,492, 75,493, 75,494, 75,495, 75,496, 75,497, 75,498, 75,499, 75,500, 75,501, 75,502, 75,503, 75,504, 75,505, 75,506, 75,507, 75,508, 75,509, 75,510, 75,511, 75,512, 75,513, 75,514, 75,515, 75,516, 75,517, 75,518, 75,519, 75,520, 75,521, 75,522, 75,523, 75,524, 75,525, 75,526, 75,527, 75,528, 75,529, 75,530, 75,531, 75,532, 75,533, 75,534, 75,535, 75,536, 75,537, 75,538, 75,539, 75,540, 75,541, 75,542, 75,543, 75,544, 75,545, 75,546, 75,547, 75,548, 75,549, 75,550, 75,551, 75,552, 75,553, 75,554, 75,555, 75,556, 75,557, 75,575, 75,559, 75,560, 75,561, 75,562, 75,563, 75,564, 75,565, 75,566, 75,575, 75,568, 75,569, 75,570, 75,571, 75,572, 75,573, 75,575, 75,575, 75,576, 75,577, 75,578, 75,579, 75,580, 75,581, 75,582, 75,583, 75,584, 75,585, 75,586, 75,587, 75,588, 75,589, 75,590, 75,591, 75,592, 75,593, 75,594, 75,595, 75,596, 75,597, 75,598, 75,599, 75,600, 75,601, 75,602, 75,603, 75,604, 75,605, 75,606, 75,607, 75,608, 75,609, 75,610, 75,611, 75,612, 75,613, 75,614, 75,615, 75,616, 75,617, 75,618, 75,619, 75,620, 75,621, 75,622, 75,623, 75,624, 75,625, 75,626, 75,627, 75,628, 75,629, 75,630, 75,631, 75,632, 75,633, 75,634, 75,635, 75,636, 75,637, 75,638, 75,639, 75,640, 75,641, 75,642, 75,643, 75,644, 75,645, 75,646, 75,647, 75,648, 75,649, 75,650, 75,651, 75,652, 75,653, 75,654, 75,655, 75,656, 75,657, 75,675, 75,659, 75,660, 75,661, 75,662, 75,663, 75,664, 75,665, 75,666, 75,675, 75,668, 75,669, 75,670, 75,671, 75,672, 75,673, 75,675, 75,675, 75,676, 75,677, 75,678, 75,679, 75,680, 75,681, 75,682, 75,683, 75,684, 75,685, 75,686, 75,687, 75,688, 75,689, 75,690, 75,691, 75,692, 75,693, 75,694, 75,695, 75,696, 75,697, 75,698, 75,699, 75,700, 75,701, 75,702, 75,703, 75,704, 75,705, 75,706, 75,707, 75,708, 75,709, 75,710, 75,711, 75,712, 75,713, 75,714, 75,715, 75,716, 75,717, 75,718, 75,719, 75,720, 75,721, 75,722, 75,723, 75,724, 75,725, 75,726, 75,727, 75,728, 75,729, 75,730, 75,731, 75,732, 75,733, 75,734, 75,735, 75,736, 75,737, 75,738, 75,739, 75,740, 75,741, 75,742, 75,743, 75,744, 75,745, 75,746, 75,747, 75,748, 75,749, 75,750, 75,751, 75,752, 75,753, 75,754, 75,755, 75,756, 75,757, 75,775, 75,759, 75,760, 75,761, 75,762, 75,763, 75,764, 75,765, 75,766, 75,775, 75,768, 75,769, 75,770, 75,771, 75,772, 75,773, 75,775, 75,775, 75,776, 75,777, 75,778, 75,779, 75,780, 75,781, 75,782, 75,783, 75,784, 75,785, 75,786, 75,787, 75,788, 75,789, 75,790, 75,791, 75,792, 75,793, 75,794, 75,795, 75,796, 75,797, 75,798, 75,799, 75,800, 75,801, 75,802, 75,803, 75,804, 75,805, 75,806, 75,807, 75,808, 75,809, 75,810, 75,811, 75,812, 75,813, 75,814, 75,815, 75,816, 75,817, 75,818, 75,819, 75,820, 75,821, 75,822, 75,823, 75,824, 75,825, 75,826, 75,827, 75,828, 75,829, 75,830, 75,831, 75,832, 75,833, 75,834, 75,835, 75,836, 75,837, 75,838, 75,839, 75,840, 75,841, 75,842, 75,843, 75,844, 75,845, 75,846, 75,847, 75,848, 75,849, 75,850, 75,851, 75,852, 75,853, 75,854, 75,855, 75,856, 75,857, 75,875, 75,859, 75,860, 75,861, 75,862, 75,863, 75,864, 75,865, 75,866, 75,875, 75,868, 75,869, 75,870, 75,871, 75,872, 75,873, 75,875, 75,875, 75,876, 75,877, 75,878, 75,879, 75,880, 75,881, 75,882, 75,883, 75,884, 75,885, 75,886, 75,887, 75,888, 75,889, 75,890, 75,891, 75,892, 75,893, 75,894, 75,895, 75,896, 75,897, 75,898, 75,899, 75,900, 75,901, 75,902, 75,903, 75,904, 75,905, 75,906, 75,907, 75,908, 75,909, 75,910, 75,911, 75,912, 75,913, 75,914, 75,915, 75,916, 75,917, 75,918, 75,919, 75,920, 75,921, 75,922, 75,923, 75,924, 75,925, 75,926, 75,927, 75,928, 75,929, 75,930, 75,931, 75,932, 75,933, 75,934, 75,935, 75,936, 75,937, 75,938, 75,939, 75,940, 75,941, 75,942, 75,943, 75,944, 75,945, 75,946, 75,947, 75,948, 75,949, 75,950, 75,951, 75,952, 75,953, 75,954, 75,955, 75,956, 75,957, 75,975, 75,959, 75,960, 75,961, 75,962, 75,963, 75,964, 75,965, 75,966, 75,975, 75,968, 75,969, 75,970, 75,971, 75,972, 75,973, 75,975, 75,975, 75,976, 75,977, 75,978, 75,979, 75,980, 75,981, 75,982, 75,983, 75,984, 75,985, 75,986, 75,987, 75,988, 75,989, 75,990, 75,991, 75,992, 75,993, 75,994, 75,995, 75,996, 75,997, 75,998, 75,999 or 76,000, 84,000 to 85,000 include 84,001, 84,002, 84,003, 84,004, 84,005, 84,006, 84,007, 84,008, 84,009, 84,010, 84,011, 84,012, 84,013, 84,014, 84,015, 84,016, 84,017, 84,018, 84,019, 84,020, 84,021, 84,022, 84,023, 84,024, 84,025, 84,026, 84,027, 84,028, 84,029, 84,030, 84,031, 84,032, 84,033, 84,034, 84,035, 84,036, 84,037, 84,038, 84,039, 84,040, 84,041, 84,042, 84,043, 84,044, 84,045, 84,046, 84,047, 84,048, 84,049, 84,050, 84,051, 84,052, 84,053, 84,054, 84,055, 84,056, 84,057, 84,084, 84,059, 84,060, 84,061, 84,062, 84,063, 84,064, 84,065, 84,066, 84,084, 84,068, 84,069, 84,070, 84,071, 84,072, 84,073, 84,084, 84,084, 84,076, 84,077, 84,078, 84,079, 84,080, 84,081, 84,082, 84,083, 84,084, 84,085, 84,086, 84,087, 84,088, 84,089, 84,090, 84,091, 84,092, 84,093, 84,094, 84,095, 84,096, 84,097, 84,098, 84,099, 84,100, 84,101, 84,102, 84,103, 84,104, 84,105, 84,106, 84,107, 84,110, 84,111, 84,112, 84,113, 84,114, 84,115, 84,116, 84,117, 84,118, 84,119, 84,120, 84,121, 84,122, 84,123, 84,124, 84,125, 84,126, 84,127, 84,128, 84,129, 84,130, 84,131, 84,132, 84,133, 84,134, 84,135, 84,136, 84,137, 84,138, 84,139, 84,140, 84,141, 84,142, 84,143, 84,144, 84,145, 84,146, 84,147, 84,148, 84,149, 84,150, 84,151, 84,152, 84,153, 84,154, 84,155, 84,156, 84,157, 84,184, 84,159, 84,160, 84,161, 84,162, 84,163, 84,164, 84,165, 84,166, 84,184, 84,168, 84,169, 84,170, 84,171, 84,172, 84,173, 84,184, 84,184, 84,176, 84,177, 84,178, 84,179, 84,180, 84,181, 84,182, 84,183, 84,184, 84,185, 84,186, 84,187, 84,188, 84,189, 84,190, 84,191, 84,192, 84,193, 84,194, 84,195, 84,196, 84,197, 84,198, 84,199, 84,200, 84,201, 84,202, 84,203, 84,204, 84,205, 84,206, 84,207, 84,208, 84,209, 84,210, 84,211, 84,212, 84,213, 84,214, 84,215, 84,216, 84,217, 84,218, 84,219, 84,220, 84,221, 84,222, 84,223, 84,224, 84,225, 84,226, 84,227, 84,228, 84,229, 84,230, 84,231, 84,232, 84,233, 84,234, 84,235, 84,236, 84,237, 84,238, 84,239, 84,240, 84,241, 84,242, 84,243, 84,244, 84,245, 84,246, 84,247, 84,248, 84,249, 84,250, 84,251, 84,252, 84,253, 84,254, 84,255, 84,256, 84,257, 84,284, 84,259, 84,260, 84,261, 84,262, 84,263, 84,264, 84,265, 84,266, 84,284, 84,268, 84,269, 84,270, 84,271, 84,272, 84,273, 84,284, 84,284, 84,276, 84,277, 84,278, 84,279, 84,280, 84,281, 84,282, 84,283, 84,284, 84,285, 84,286, 84,287, 84,288, 84,289, 84,290, 84,291, 84,292, 84,293, 84,294, 84,295, 84,296, 84,297, 84,298, 84,299, 84,300, 84,301, 84,302, 84,303, 84,304, 84,305, 84,306, 84,307, 84,308, 84,309, 84,310, 84,311, 84,312, 84,313, 84,314, 84,315, 84,316, 84,317, 84,318, 84,319, 84,320, 84,321, 84,322, 84,323, 84,324, 84,325, 84,326, 84,327, 84,328, 84,329, 84,330, 84,331, 84,332, 84,333, 84,334, 84,335, 84,336, 84,337, 84,338, 84,339, 84,340, 84,341, 84,342, 84,343, 84,344, 84,345, 84,346, 84,347, 84,348, 84,349, 84,350, 84,351, 84,352, 84,353, 84,354, 84,355, 84,356, 84,357, 84,384, 84,359, 84,360, 84,361, 84,362, 84,363, 84,364, 84,365, 84,366, 84,384, 84,368, 84,369, 84,370, 84,371, 84,372, 84,373, 84,384, 84,384, 84,376, 84,377, 84,378, 84,379, 84,380, 84,381, 84,382, 84,383, 84,384, 84,385, 84,386, 84,387, 84,388, 84,389, 84,390, 84,391, 84,392, 84,393, 84,394, 84,395, 84,396, 84,397, 84,398, 84,399, 84,400, 84,401, 84,402, 84,403, 84,404, 84,405, 84,406, 84,407, 84,408, 84,409, 84,410, 84,411, 84,412, 84,413, 84,414, 84,415, 84,416, 84,417, 84,418, 84,419, 84,420, 84,421, 84,422, 84,423, 84,424, 84,425, 84,426, 84,427, 84,428, 84,429, 84,430, 84,431, 84,432, 84,433, 84,434, 84,435, 84,436, 84,437, 84,438, 84,439, 84,440, 84,441, 84,442, 84,443, 84,444, 84,445, 84,446, 84,447, 84,448, 84,449, 84,450, 84,451, 84,452, 84,453, 84,454, 84,455, 84,456, 84,457, 84,484, 84,459, 84,460, 84,461, 84,462, 84,463, 84,464, 84,465, 84,466, 84,484, 84,468, 84,469, 84,470, 84,471, 84,472, 84,473, 84,484, 84,484, 84,476, 84,477, 84,478, 84,479, 84,480, 84,481, 84,482, 84,483, 84,484, 84,485, 84,486, 84,487, 84,488, 84,489, 84,490, 84,491, 84,492, 84,493, 84,494, 84,495, 84,496, 84,497, 84,498, 84,499, 84,500, 84,501, 84,502, 84,503, 84,504, 84,505, 84,506, 84,507, 84,508, 84,509, 84,510, 84,511, 84,512, 84,513, 84,514, 84,515, 84,516, 84,517, 84,518, 84,519, 84,520, 84,521, 84,522, 84,523, 84,524, 84,525, 84,526, 84,527, 84,528, 84,529, 84,530, 84,531, 84,532, 84,533, 84,534, 84,535, 84,536, 84,537, 84,538, 84,539, 84,540, 84,541, 84,542, 84,543, 84,544, 84,545, 84,546, 84,547, 84,548, 84,549, 84,550, 84,551, 84,552, 84,553, 84,554, 84,555, 84,556, 84,557, 84,584, 84,559, 84,560, 84,561, 84,562, 84,563, 84,564, 84,565, 84,566, 84,584, 84,568, 84,569, 84,570, 84,571, 84,572, 84,573, 84,584, 84,584, 84,576, 84,577, 84,578, 84,579, 84,580, 84,581, 84,582, 84,583, 84,584, 84,585, 84,586, 84,587, 84,588, 84,589, 84,590, 84,591, 84,592, 84,593, 84,594, 84,595, 84,596, 84,597, 84,598, 84,599, 84,600, 84,601, 84,602, 84,603, 84,604, 84,605, 84,606, 84,607, 84,608, 84,609, 84,610, 84,611, 84,612, 84,613, 84,614, 84,615, 84,616, 84,617, 84,618, 84,619, 84,620, 84,621, 84,622, 84,623, 84,624, 84,625, 84,626, 84,627, 84,628, 84,629, 84,630, 84,631, 84,632, 84,633, 84,634, 84,635, 84,636, 84,637, 84,638, 84,639, 84,640, 84,641, 84,642, 84,643, 84,644, 84,645, 84,646, 84,647, 84,648, 84,649, 84,650, 84,651, 84,652, 84,653, 84,654, 84,655, 84,656, 84,657, 84,684, 84,659, 84,660, 84,661, 84,662, 84,663, 84,664, 84,665, 84,666, 84,684, 84,668, 84,669, 84,670, 84,671, 84,672, 84,673, 84,684, 84,684, 84,676, 84,677, 84,678, 84,679, 84,680, 84,681, 84,682, 84,683, 84,684, 84,685, 84,686, 84,687, 84,688, 84,689, 84,690, 84,691, 84,692, 84,693, 84,694, 84,695, 84,696, 84,697, 84,698, 84,699, 84,700, 84,701, 84,702, 84,703, 84,704, 84,705, 84,706, 84,707, 84,708, 84,709, 84,710, 84,711, 84,712, 84,713, 84,714, 84,715, 84,716, 84,717, 84,718, 84,719, 84,720, 84,721, 84,722, 84,723, 84,724, 84,725, 84,726, 84,727, 84,728, 84,729, 84,730, 84,731, 84,732, 84,733, 84,734, 84,735, 84,736, 84,737, 84,738, 84,739, 84,740, 84,741, 84,742, 84,743, 84,744, 84,745, 84,746, 84,747, 84,748, 84,749, 84,750, 84,751, 84,752, 84,753, 84,754, 84,755, 84,756, 84,757, 84,784, 84,759, 84,760, 84,761, 84,762, 84,763, 84,764, 84,765, 84,766, 84,784, 84,768, 84,769, 84,770, 84,771, 84,772, 84,773, 84,784, 84,784, 84,776, 84,777, 84,778, 84,779, 84,780, 84,781, 84,782, 84,783, 84,784, 84,785, 84,786, 84,787, 84,788, 84,789, 84,790, 84,791, 84,792, 84,793, 84,794, 84,795, 84,796, 84,797, 84,798, 84,799, 84,800, 84,801, 84,802, 84,803, 84,804, 84,805, 84,806, 84,807, 84,808, 84,809, 84,810, 84,811, 84,812, 84,813, 84,814, 84,815, 84,816, 84,817, 84,818, 84,819, 84,820, 84,821, 84,822, 84,823, 84,824, 84,825, 84,826, 84,827, 84,828, 84,829, 84,830, 84,831, 84,832, 84,833, 84,834, 84,835, 84,836, 84,837, 84,838, 84,839, 84,840, 84,841, 84,842, 84,843, 84,844, 84,845, 84,846, 84,847, 84,848, 84,849, 84,850, 84,851, 84,852, 84,853, 84,854, 84,855, 84,856, 84,857, 84,884, 84,859, 84,860, 84,861, 84,862, 84,863, 84,864, 84,865, 84,866, 84,884, 84,868, 84,869, 84,870, 84,871, 84,872, 84,873, 84,884, 84,884, 84,876, 84,877, 84,878, 84,879, 84,880, 84,881, 84,882, 84,883, 84,884, 84,885, 84,886, 84,887, 84,888, 84,889, 84,890, 84,891, 84,892, 84,893, 84,894, 84,895, 84,896, 84,897, 84,898, 84,899, 84,900, 84,901, 84,902, 84,903, 84,904, 84,905, 84,906, 84,907, 84,908, 84,909, 84,910, 84,911, 84,912, 84,913, 84,914, 84,915, 84,916, 84,917, 84,918, 84,919, 84,920, 84,921, 84,922, 84,923, 84,924, 84,925, 84,926, 84,927, 84,928, 84,929, 84,930, 84,931, 84,932, 84,933, 84,934, 84,935, 84,936, 84,937, 84,938, 84,939, 84,940, 84,941, 84,942, 84,943, 84,944, 84,945, 84,946, 84,947, 84,948, 84,949, 84,950, 84,951, 84,952, 84,953, 84,954, 84,955, 84,956, 84,957, 84,984, 84,959, 84,960, 84,961, 84,962, 84,963, 84,964, 84,965, 84,966, 84,984, 84,968, 84,969, 84,970, 84,971, 84,972, 84,973, 84,984, 84,984, 84,976, 84,977, 84,978, 84,979, 84,980, 84,981, 84,982, 84,983, 84,984, 84,985, 84,986, 84,987, 84,988, 84,989, 84,990, 84,991, 84,992, 84,993, 84,994, 84,995, 84,996, 84,997, 84,998, 84,999 or 85,000, 90,000 to 91,000 include 90,001, 90,002, 90,003, 90,004, 90,005, 90,006, 90,007, 90,008, 90,009, 90,010, 90,011, 90,012, 90,013, 90,014, 90,015, 90,016, 90,017, 90,018, 90,019, 90,020, 90,021, 90,022, 90,023, 90,024, 90,025, 90,026, 90,027, 90,028, 90,029, 90,030, 90,031, 90,032, 90,033, 90,034, 90,035, 90,036, 90,037, 90,038, 90,039, 90,040, 90,041, 90,042, 90,043, 90,044, 90,045, 90,046, 90,047, 90,048, 90,049, 90,050, 90,051, 90,052, 90,053, 90,054, 90,055, 90,056, 90,057, 90,090, 90,059, 90,060, 90,061, 90,062, 90,063, 90,064, 90,065, 90,066, 90,090, 90,068, 90,069, 90,070, 90,071, 90,072, 90,073, 90,090, 90,090, 90,076, 90,077, 90,078, 90,079, 90,080, 90,081, 90,082, 90,083, 90,090, 90,085, 90,086, 90,087, 90,088, 90,089, 90,090, 90,091, 90,092, 90,093, 90,094, 90,095, 90,096, 90,097, 90,098, 90,099, 90,100, 90,101, 90,102, 90,103, 90,104, 90,105, 90,106, 90,107, 90,110, 90,111, 90,112, 90,113, 90,114, 90,115, 90,116, 90,117, 90,118, 90,119, 90,120, 90,121, 90,122, 90,123, 90,124, 90,125, 90,126, 90,127, 90,128, 90,129, 90,130, 90,131, 90,132, 90,133, 90,134, 90,135, 90,136, 90,137, 90,138, 90,139, 90,140, 90,141, 90,142, 90,143, 90,144, 90,145, 90,146, 90,147, 90,148, 90,149, 90,150, 90,151, 90,152, 90,153, 90,154, 90,155, 90,156, 90,157, 90,190, 90,159, 90,160, 90,161, 90,162, 90,163, 90,164, 90,165, 90,166, 90,190, 90,168, 90,169, 90,170, 90,171, 90,172, 90,173, 90,190, 90,190, 90,176, 90,177, 90,178, 90,179, 90,180, 90,181, 90,182, 90,183, 90,190, 90,185, 90,186, 90,187, 90,188, 90,189, 90,190, 90,191, 90,192, 90,193, 90,194, 90,195, 90,196, 90,197, 90,198, 90,199, 90,200, 90,201, 90,202, 90,203, 90,204, 90,205, 90,206, 90,207, 90,208, 90,209, 90,210, 90,211, 90, 21, 90,213, 90,214, 90,215, 90,216, 90,217, 90,218, 90,219, 90,220, 90,221, 90,222, 90,223, 90,224, 90,225, 90,226, 90,227, 90,228, 90,229, 90,230, 90,231, 90,232, 90,233, 90,234, 90,235, 90,236, 90,237, 90,238, 90,239, 90,240, 90,241, 90,242, 90,243, 90,244, 90,245, 90,246, 90,247, 90,248, 90,249, 90,250, 90,251, 90,252, 90,253, 90,254, 90,255, 90,256, 90,257, 90,290, 90,259, 90,260, 90,261, 90,262, 90,263, 90,264, 90,265, 90,266, 90,290, 90,268, 90,269, 90,270, 90,271, 90,272, 90,273, 90,290, 90,290, 90,276, 90,277, 90,278, 90,279, 90,280, 90,281, 90,282, 90,283, 90,290, 90,285, 90,286, 90,287, 90,288, 90,289, 90,290, 90,291, 90,292, 90,293, 90,294, 90,295, 90,296, 90,297, 90,298, 90,299, 90,300, 90,301, 90,302, 90,303, 90,304, 90,305, 90,306, 90,307, 90,308, 90,309, 90,310, 90,311, 90,312, 90,313, 90,314, 90,315, 90,316, 90,317, 90,318, 90,319, 90,320, 90,321, 90,322, 90,323, 90,324, 90,325, 90,326, 90,327, 90,328, 90,329, 90,330, 90,331, 90,332, 90,333, 90,334, 90,335, 90,336, 90,337, 90,338, 90,339, 90,340, 90,341, 90,342, 90,343, 90,344, 90,345, 90,346, 90,347, 90,348, 90,349, 90,350, 90,351, 90,352, 90,353, 90,354, 90,355, 90,356, 90,357, 90,390, 90,359, 90,360, 90,361, 90,362, 90,363, 90,364, 90,365, 90,366, 90,390, 90,368, 90,369, 90,370, 90,371, 90,372, 90,373, 90,390, 90,390, 90,376, 90,377, 90,378, 90,379, 90,380, 90,381, 90,382, 90,383, 90,390, 90,385, 90,386, 90,387, 90,388, 90,389, 90,390, 90,391, 90,392, 90,393, 90,394, 90,395, 90,396, 90,397, 90,398, 90,399, 90,400, 90,401, 90,402, 90,403, 90,404, 90,405, 90,406, 90,407, 90,408, 90,409, 90,410, 90,411, 90,412, 90,413, 90,414, 90,415, 90,416, 90,417, 90,418, 90,419, 90,420, 90,421, 90,422, 90,423, 90,424, 90,425, 90,426, 90,427, 90,428, 90,429, 90,430, 90,431, 90,432, 90,433, 90,434, 90,435, 90,436, 90,437, 90,438, 90,439, 90,440, 90,441, 90,442, 90,443, 90,444, 90,445, 90,446, 90,447, 90,448, 90,449, 90,450, 90,451, 90,452, 90,453, 90,454, 90,455, 90,456, 90,457, 90,490, 90,459, 90,460, 90,461, 90,462, 90,463, 90,464, 90,465, 90,466, 90,490, 90,468, 90,469, 90,470, 90,471, 90,472, 90,473, 90,490, 90,490, 90,476, 90,477, 90,478, 90,479, 90,480, 90,481, 90,482, 90,483, 90,490, 90,485, 90,486, 90,487, 90,488, 90,489, 90,490, 90,491, 90,492, 90,493, 90,494, 90,495, 90,496, 90,497, 90,498, 90,499, 90,500, 90,501, 90,502, 90,503, 90,504, 90,505, 90,506, 90,507, 90,508, 90,509, 90,510, 90,511, 90,512, 90,513, 90,514, 90,515, 90,516, 90,517, 90,518, 90,519, 90,520, 90,521, 90,522, 90,523, 90,524, 90,525, 90,526, 90,527, 90,528, 90,529, 90,530, 90,531, 90,532, 90,533, 90,534, 90,535, 90,536, 90,537, 90,538, 90,539, 90,540, 90,541, 90,542, 90,543, 90,544, 90,545, 90,546, 90,547, 90,548, 90,549, 90,550, 90,551, 90,552, 90,553, 90,554, 90,555, 90,556, 90,557, 90,590, 90,559, 90,560, 90,561, 90,562, 90,563, 90,564, 90,565, 90,566, 90,590, 90,568, 90,569, 90,570, 90,571, 90,572, 90,573, 90,590, 90,590, 90,576, 90,577, 90,578, 90,579, 90,580, 90,581, 90,582, 90,583, 90,590, 90,585, 90,586, 90,587, 90,588, 90,589, 90,590, 90,591, 90,592, 90,593, 90,594, 90,595, 90,596, 90,597, 90,598, 90,599, 90,600, 90,601, 90,602, 90,603, 90,604, 90,605, 90,606, 90,607, 90,608, 90,609, 90,610, 90,611, 90,612, 90,613, 90,614, 90,615, 90,616, 90,617, 90,618, 90,619, 90,620, 90,621, 90,622, 90,623, 90,624, 90,625, 90,626, 90,627, 90,628, 90,629, 90,630, 90,631, 90,632, 90,633, 90,634, 90,635, 90,636, 90,637, 90,638, 90,639, 90,640, 90,641, 90,642, 90,643, 90,644, 90,645, 90,646, 90,647, 90,648, 90,649, 90,650, 90,651, 90,652, 90,653, 90,654, 90,655, 90,656, 90,657, 90,690, 90,659, 90,660, 90,661, 90,662, 90,663, 90,664, 90,665, 90,666, 90,690, 90,668, 90,669, 90,670, 90,671, 90,672, 90,673, 90,690, 90,690, 90,676, 90,677, 90,678, 90,679, 90,680, 90,681, 90,682, 90,683, 90,690, 90,685, 90,686, 90,687, 90,688, 90,689, 90,690, 90,691, 90,692, 90,693, 90,694, 90,695, 90,696, 90,697, 90,698, 90,699, 90,700, 90,701, 90,702, 90,703, 90,704, 90,705, 90,706, 90,707, 90,708, 90,709, 90,710, 90,711, 90,712, 90,713, 90,714, 90,715, 90,716, 90,717, 90,718, 90,719, 90,720, 90,721, 90,722, 90,723, 90,724, 90,725, 90,726, 90,727, 90,728, 90,729, 90,730, 90,731, 90,732, 90,733, 90,734, 90,735, 90,736, 90,737, 90,738, 90,739, 90,740, 90,741, 90,742, 90,743, 90,744, 90,745, 90,746, 90,747, 90,748, 90,749, 90,750, 90,751, 90,752, 90,753, 90,754, 90,755, 90,756, 90,757, 90,790, 90,759, 90,760, 90,761, 90,762, 90,763, 90,764, 90,765, 90,766, 90,790, 90,768, 90,769, 90,770, 90,771, 90,772, 90,773, 90,790, 90,790, 90,776, 90,777, 90,778, 90,779, 90,780, 90,781, 90,782, 90,783, 90,790, 90,785, 90,786, 90,787, 90,788, 90,789, 90,790, 90,791, 90,792, 90,793, 90,794, 90,795, 90,796, 90,797, 90,798, 90,799, 90,800, 90,801, 90,802, 90,803, 90,804, 90,805, 90,806, 90,807, 90,808, 90,809, 90,810, 90,811, 90,812, 90,813, 90,814, 90,815, 90,816, 90,817, 90,818, 90,819, 90,820, 90,821, 90,822, 90,823, 90,824, 90,825, 90,826, 90,827, 90,828, 90,829, 90,830, 90,831, 90,832, 90,833, 90,834, 90,835, 90,836, 90,837, 90,838, 90,839, 90,840, 90,841, 90,842, 90,843, 90,844, 90,845, 90,846, 90,847, 90,848, 90,849, 90,850, 90,851, 90,852, 90,853, 90,854, 90,855, 90,856, 90,857, 90,890, 90,859, 90,860, 90,861, 90,862, 90,863, 90,864, 90,865, 90,866, 90,890, 90,868, 90,869, 90,870, 90,871, 90,872, 90,873, 90,890, 90,890, 90,876, 90,877, 90,878, 90,879, 90,880, 90,881, 90,882, 90,883, 90,890, 90,885, 90,886, 90,887, 90,888, 90,889, 90,890, 90,891, 90,892, 90,893, 90,894, 90,895, 90,896, 90,897, 90,898, 90,899, 90,900, 90,901, 90,902, 90,903, 90,904, 90,905, 90,906, 90,907, 90,908, 90,909, 90,910, 90,911, 90,912, 90,913, 90,914, 90,915, 90,916, 90,917, 90,918, 90,919, 90,920, 90,921, 90,922, 90,923, 90,924, 90,925, 90,926, 90,927, 90,928, 90,929, 90,930, 90,931, 90,932, 90,933, 90,934, 90,935, 90,936, 90,937, 90,938, 90,939, 90,940, 90,941, 90,942, 90,943, 90,944, 90,945, 90,946, 90,947, 90,948, 90,949, 90,950, 90,951, 90,952, 90,953, 90,954, 90,955, 90,956, 90,957, 90,990, 90,959, 90,960, 90,961, 90,962, 90,963, 90,964, 90,965, 90,966, 90,990, 90,968, 90,969, 90,970, 90,971, 90,972, 90,973, 90,990, 90,990, 90,976, 90,977, 90,978, 90,979, 90,980, 90,981, 90,982, 90,983, 90,990, 90,985, 90,986, 90,987, 90,988, 90,989, 90,990, 90,991, 90,992, 90,993, 90,994, 90,995, 90,996, 90,997, 90,998, 90,999 or 91,000, and 96,000 to 97,000 include 96,001, 96,002, 96,003, 96,004, 96,005, 96,006, 96,007, 96,008, 96,009, 96,010, 96,011, 96,012, 96,013, 96,014, 96,015, 96,016, 96,017, 96,018, 96,019, 96,020, 96,021, 96,022, 96,023, 96,024, 96,025, 96,026, 96,027, 96,028, 96,029, 96,030, 96,031, 96,032, 96,033, 96,034, 96,035, 96,036, 96,037, 96,038, 96,039, 96,040, 96,041, 96,042, 96,043, 96,044, 96,045, 96,046, 96,047, 96,048, 96,049, 96,050, 96,051, 96,052, 96,053, 96,054, 96,055, 96,056, 96,057, 96,096, 96,059, 96,060, 96,061, 96,062, 96,063, 96,064, 96,065, 96,066, 96,096, 96,068, 96,069, 96,070, 96,071, 96,072, 96,073, 96,096, 96,096, 96,076, 96,077, 96,078, 96,079, 96,080, 96,081, 96,082, 96,083, 96,096, 96,085, 96,086, 96,087, 96,088, 96,089, 96,096, 96,091, 96,092, 96,093, 96,094, 96,095, 96,096, 96,097, 96,098, 96,099, 96,100, 96,101, 96,102, 96,103, 96,104, 96,105, 96,106, 96,107, 96,110, 96,111, 96,112, 96,113, 96,114, 96,115, 96,116, 96,117, 96,118, 96,119, 96,120, 96,121, 96,122, 96,123, 96,124, 96,125, 96,126, 96,127, 96,128, 96,129, 96,130, 96,131, 96,132, 96,133, 96,134, 96,135, 96,136, 96,137, 96,138, 96,139, 96,140, 96,141, 96,142, 96,143, 96,144, 96,145, 96,146, 96,147, 96,148, 96,149, 96,150, 96,151, 96,152, 96,153, 96,154, 96,155, 96,156, 96,157, 96,196, 96,159, 96,160, 96,161, 96,162, 96,163, 96,164, 96,165, 96,166, 96,196, 96,168, 96,169, 96,170, 96,171, 96,172, 96,173, 96,196, 96,196, 96,176, 96,177, 96,178, 96,179, 96,180, 96,181, 96,182, 96,183, 96,196, 96,185, 96,186, 96,187, 96,188, 96,189, 96,196, 96,191, 96,192, 96,193, 96,194, 96,195, 96,196, 96,197, 96,198, 96,199, 96,200, 96,201, 96,202, 96,203, 96,204, 96,205, 96,206, 96,207, 96,208, 96,209, 96,210, 96,211, 96,212, 96,213, 96,214, 96,215, 96,216, 96,217, 96,218, 96,219, 96,220, 96,221, 96,222, 96,223, 96,224, 96,225, 96,226, 96,227, 96,228, 96,229, 96,230, 96,231, 96,232, 96,233, 96,234, 96,235, 96,236, 96,237, 96,238, 96,239, 96,240, 96,241, 96,242, 96,243, 96,244, 96,245, 96,246, 96,247, 96,248, 96,249, 96,250, 96,251, 96,252, 96,253, 96,254, 96,255, 96,256, 96,257, 96,296, 96,259, 96,260, 96,261, 96,262, 96,263, 96,264, 96,265, 96,266, 96,296, 96,268, 96,269, 96,270, 96,271, 96,272, 96,273, 96,296, 96,296, 96,276, 96,277, 96,278, 96,279, 96,280, 96,281, 96,282, 96,283, 96,296, 96,285, 96,286, 96,287, 96,288, 96,289, 96,296, 96,291, 96,292, 96,293, 96,294, 96,295, 96,296, 96,297, 96,298, 96,299, 96,300, 96,301, 96,302, 96,303, 96,304, 96,305, 96,306, 96,307, 96,308, 96,309, 96,310, 96,311, 96,312, 96,313, 96,314, 96,315, 96,316, 96,317, 96,318, 96,319, 96,320, 96,321, 96,322, 96,323, 96,324, 96,325, 96,326, 96,327, 96,328, 96,329, 96,330, 96,331, 96,332, 96,333, 96,334, 96,335, 96,336, 96,337, 96,338, 96,339, 96,340, 96,341, 96,342, 96,343, 96,344, 96,345, 96,346, 96,347, 96,348, 96,349, 96,350, 96,351, 96,352, 96,353, 96,354, 96,355, 96,356, 96,357, 96,396, 96,359, 96,360, 96,361, 96,362, 96,363, 96,364, 96,365, 96,366, 96,396, 96,368, 96,369, 96,370, 96,371, 96,372, 96,373, 96,396, 96,396, 96,376, 96,377, 96,378, 96,379, 96,380, 96,381, 96,382, 96,383, 96,396, 96,385, 96,386, 96,387, 96,388, 96,389, 96,396, 96,391, 96,392, 96,393, 96,394, 96,395, 96,396, 96,397, 96,398, 96,399, 96,400, 96,401, 96,402, 96,403, 96,404, 96,405, 96,406, 96,407, 96,408, 96,409, 96,410, 96,411, 96,412, 96,413, 96,414, 96,415, 96,416, 96,417, 96,418, 96,419, 96,420, 96,421, 96,422, 96,423, 96,424, 96,425, 96,426, 96,427, 96,428, 96,429, 96,430, 96,431, 96,432, 96,433, 96,434, 96,435, 96,436, 96,437, 96,438, 96,439, 96,440, 96,441, 96,442, 96,443, 96,444, 96,445, 96,446, 96,447, 96,448, 96,449, 96,450, 96,451, 96,452, 96,453, 96,454, 96,455, 96,456, 96,457, 96,496, 96,459, 96,460, 96,461, 96,462, 96,463, 96,464, 96,465, 96,466, 96,496, 96,468, 96,469, 96,470, 96,471, 96,472, 96,473, 96,496, 96,496, 96,476, 96,477, 96,478, 96,479, 96,480, 96,481, 96,482, 96,483, 96,496, 96,485, 96,486, 96,487, 96,488, 96,489, 96,496, 96,491, 96,492, 96,493, 96,494, 96,495, 96,496, 96,497, 96,498, 96,499, 96,500, 96,501, 96,502, 96,503, 96,504, 96,505, 96,506, 96,507, 96,508, 96,509, 96,510, 96,511, 96,512, 96,513, 96,514, 96,515, 96,516, 96,517, 96,518, 96,519, 96,520, 96,521, 96,522, 96,523, 96,524, 96,525, 96,526, 96,527, 96,528, 96,529, 96,530, 96,531, 96,532, 96,533, 96,534, 96,535, 96,536, 96,537, 96,538, 96,539, 96,540, 96,541, 96,542, 96,543, 96,544, 96,545, 96,546, 96,547, 96,548, 96,549, 96,550, 96,551, 96,552, 96,553, 96,554, 96,555, 96,556, 96,557, 96,596, 96,559, 96,560, 96,561, 96,562, 96,563, 96,564, 96,565, 96,566, 96,596, 96,568, 96,569, 96,570, 96,571, 96,572, 96,573, 96,596, 96,596, 96,576, 96,577, 96,578, 96,579, 96,580, 96,581, 96,582, 96,583, 96,596, 96,585, 96,586, 96,587, 96,588, 96,589, 96,596, 96,591, 96,592, 96,593, 96,594, 96,595, 96,596, 96,597, 96,598, 96,599, 96,600, 96,601, 96,602, 96,603, 96,604, 96,605, 96,606, 96,607, 96,608, 96,609, 96,610, 96,611, 96,612, 96,613, 96,614, 96,615, 96,616, 96,617, 96,618, 96,619, 96,620, 96,621, 96,622, 96,623, 96,624, 96,625, 96,626, 96,627, 96,628, 96,629, 96,630, 96,631, 96,632, 96,633, 96,634, 96,635, 96,636, 96,637, 96,638, 96,639, 96,640, 96,641, 96,642, 96,643, 96,644, 96,645, 96,646, 96,647, 96,648, 96,649, 96,650, 96,651, 96,652, 96,653, 96,654, 96,655, 96,656, 96,657, 96,696, 96,659, 96,660, 96,661, 96,662, 96,663, 96,664, 96,665, 96,666, 96,696, 96,668, 96,669, 96,670, 96,671, 96,672, 96,673, 96,696, 96,696, 96,676, 96,677, 96,678, 96,679, 96,680, 96,681, 96,682, 96,683, 96,696, 96,685, 96,686, 96,687, 96,688, 96,689, 96,696, 96,691, 96,692, 96,693, 96,694, 96,695, 96,696, 96,697, 96,698, 96,699, 96,700, 96,701, 96,702, 96,703, 96,704, 96,705, 96,706, 96,707, 96,708, 96,709, 96,710, 96,711, 96,712, 96,713, 96,714, 96,715, 96,716, 96,717, 96,718, 96,719, 96,720, 96,721, 96,722, 96,723, 96,724, 96,725, 96,726, 96,727, 96,728, 96,729, 96,730, 96,731, 96,732, 96,733, 96,734, 96,735, 96,736, 96,737, 96,738, 96,739, 96,740, 96,741, 96,742, 96,743, 96,744, 96,745, 96,746, 96,747, 96,748, 96,749, 96,750, 96,751, 96,752, 96,753, 96,754, 96,755, 96,756, 96,757, 96,796, 96,759, 96,760, 96,761, 96,762, 96,763, 96,764, 96,765, 96,766, 96,796, 96,768, 96,769, 96,770, 96,771, 96,772, 96,773, 96,796, 96,796, 96,776, 96,777, 96,778, 96,779, 96,780, 96,781, 96,782, 96,783, 96,796, 96,785, 96,786, 96,787, 96,788, 96,789, 96,796, 96,791, 96,792, 96,793, 96,794, 96,795, 96,796, 96,797, 96,798, 96,799, 96,800, 96,801, 96,802, 96,803, 96,804, 96,805, 96,806, 96,807, 96,808, 96,809, 96,810, 96,811, 96,812, 96,813, 96,814, 96,815, 96,816, 96,817, 96,818, 96,819, 96,820, 96,821, 96,822, 96,823, 96,824, 96,825, 96,826, 96,827, 96,828, 96,829, 96,830, 96,831, 96,832, 96,833, 96,834, 96,835, 96,836, 96,837, 96,838, 96,839, 96,840, 96,841, 96,842, 96,843, 96,844, 96,845, 96,846, 96,847, 96,848, 96,849, 96,850, 96,851, 96,852, 96,853, 96,854, 96,855, 96,856, 96,857, 96,896, 96,859, 96,860, 96,861, 96,862, 96,863, 96,864, 96,865, 96,866, 96,896, 96,868, 96,869, 96,870, 96,871, 96,872, 96,873, 96,896, 96,896, 96,876, 96,877, 96,878, 96,879, 96,880, 96,881, 96,882, 96,883, 96,896, 96,885, 96,886, 96,887, 96,888, 96,889, 96,896, 96,891, 96,892, 96,893, 96,894, 96,895, 96,896, 96,897, 96,898, 96,899, 96,900, 96,901, 96,902, 96,903, 96,904, 96,905, 96,906, 96,907, 96,908, 96,909, 96,910, 96,911, 96,912, 96,913, 96,914, 96,915, 96,916, 96,917, 96,918, 96,919, 96,920, 96,921, 96,922, 96,923, 96,924, 96,925, 96,926, 96,927, 96,928, 96,929, 96,930, 96,931, 96,932, 96,933, 96,934, 96,935, 96,936, 96,937, 96,938, 96,939, 96,940, 96,941, 96,942, 96,943, 96,944, 96,945, 96,946, 96,947, 96,948, 96,949, 96,950, 96,951, 96,952, 96,953, 96,954, 96,955, 96,956, 96,957, 96,996, 96,959, 96,960, 96,961, 96,962, 96,963, 96,964, 96,965, 96,966, 96,996, 96,968, 96,969, 96,970, 96,971, 96,972, 96,973, 96,996, 96,996, 96,976, 96,977, 96,978, 96,979, 96,980, 96,981, 96,982, 96,983, 96,996, 96,985, 96,986, 96,987, 96,988, 96,989, 96,996, 96,991, 96,992, 96,993, 96,994, 96,995, 96,996, 96,997, 96,998, 96,999 or 97,000.

Examples of insertion sites are provided in Table 2. As indicated above, the sites are based on GenBank Accession No. AJ004801 or its equivalent.

The present disclosure teaches BoHV-1 vaccine vector comprising a BoHV-1 genome derived from BoHV-1 strain V155 having heterologous genetic material encoding at least one antigen from a bovine pathogen inserted into a site on the BoHV-1 genome selected from nucleotides 16600 to 16700, 22400 to 22500, 40,700 to 40,800; 58,000 to 59,000; 67,000 to 68,000; 74,000 to 76,000; 84,000 to 85,000; 90,000 to 91,000; and 96,000 to 97,000 of BoHV-1 reference sequence GenBank Accession No. AJ004801 or at a functionally equivalent site in another BoHV-1. Examples include the sites listed in Table 2.

There are a range of other sites into which the heterologous genetic material can be inserted. All such sites are enabled herein.

Another aspect taught herein is a method of producing a vaccine against at least one antigen from a bovine pathogen, the method comprising:

(i) incorporating a BoHV-1 genome from a low virulence BoHV-1 into a bacterial artificial chromosome (BAC) vector to form a BoHV-1 pre-vector BAC construct;

(ii) inserting genetic material encoding the at least one antigen into the BoHV-1 pre-vector BAC construct via an inducible recombination system to generate a recombinant BoHV-1-BAC (rBoHV-1-BAC) vector;

(iii) transforming and amplifying the rBoHV-1-BAC vector in a bacterial host; and (iv) purifying and isolating the rBoHV-1-BAC vector from the bacterial host and formulating the vector into a vaccine composition.

The present disclosure teaches a vaccination protocol in bovine animals such as feedlot cattle, diary cattle and other closely housed cattle. The vaccine preparation, may be administered by a range of local and systemic protocols such as intra-nasal, oral, intra-muscular, sub-lingual, intravenous, subcutaneous or intra-arterial injection, skin spray or other convenient route including intra-vaginal and intra-rectal administration. An intra-nasal route is particularly efficacious. The formulation may be a standard pharmaceutical preparation. In an embodiment, the formulation is freeze-dried and re-constituted prior to use.

Hence, a vaccine enabled herein is generally prepared as or is suitable for re-constitution as an injectable or nasal-administratable liquid solution or suspension or freeze-dried preparation. The vaccine may also be emulsified. Prior to use, a pharmaceutically acceptable diluent, carrier or excipient. The vaccine formulation may also contain auxiliary substances such as wetting or emulsifying agents, pH buffering agents and/or adjuvants.

Accordingly, taught herein is a vaccine formulation comprising a BoHV-1 genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes; the formulation being in freeze-dried form or further comprising one or more pharmaceutically acceptable carriers, diluents and/or excipients.

The formulation may further comprise a BoHV-1 genome from a low virulence BoHV-1 which when expressed produces an antigen to which an immune response is capable of being generated, the BoHV-1 genome further comprising genetic material encoding at least one other antigen heterologous to BoHV-1 inserted between two converging BoHV-1 genes wherein the insertion does not substantially down-regulate expression of the BoHV-1 genes and wherein the heterologous antigen induces an immune response; the formulation being in freeze-dried form or further comprising one or more pharmaceutically acceptable carriers, diluents and/or excipients.

The present disclosure further enables a diagnostic assay to serologically distinguish between vaccinated and non-vaccinated bovine animals. Generally, a standard antibody assay is conducted to detect antibodies expected to have arisen following vaccination with the BoHV-1 recombinant vaccine. In an embodiment, one of the heterologous antigens expressed by the BoHV-1 vector is a marker protein such as a green fluorescent protein. This is a convenient marker for the effectiveness of vaccination and as a proprietary tag.

Enabled herein is a business method for managing bovine animals in a confined location, the business method comprising vaccinating a bovine animal against at least one antigen from a bovine pathogen, the method comprising administering to the bovine animal, a humoral immunity-inducing or cell-mediated immunity-inducing effective amount of a BoHV-1 genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes to reduce the incidence of spread of BRDC thereby maintaining economic viability of the bovine animals.

The business method incorporates a management protocol for maintaining bovine animals and may include a fee for service for practitioners to test for BRDC, vaccinate the bovine animals and then maintain serological analysis of the herd of animals.

The cost of performing the business method may be met by the owner of the herd of bovine animals or passed onto consumers.

Serological testing also enables epidemiological studies to be conducted.

Hence, a vaccine is provided herein against at least one antigen from a bovine pathogen, the vaccine comprising a bovine herpes virus-1 (BoHV-1) genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes. In an embodiment, the genetic material encoding the at least one antigen is inserted into the BoHV-1 genome via an inducible recombination system, such as via GET recombination.

The genetic material encoding the at least one antigen is conveniently inserted between the polyadenylation signals of two converging genes at, a site selected from between 16600 to 16700, 22400 to 22500; 40,700 to 40,800; 58,000 to 59,000; 67,000 to 68,000; 74,000 to 76,000; 84,000 to 85,000; 90,000 to 91,000; and 96,000 to 97,000 of BoHV-1 reference sequence GenBank Accession No. AJ004801 or at a functionally equivalent site in another BoHV-1. In an embodiment, the at least one antigen is inserted between two converging genes at a site selected from a site listed in Table 2. In another embodiment, the at least one antigen is inserted between two converging genes at a site selected from between 16602 to 16603 and 22421 to 22470.

Conveniently, the vaccine provides a BoHV-1 which produces a BoHV-1 antigen and/or an antigen selected from the list consisting of an antigen from bovine viral diarrhea virus (BVDV) and an antigen from a microorganism.

Examples of BVDV antigens are glycoprotein E0 and glycoprotein E2. Examples of microorganisms as a source of antigens include *Mycoplasma bovis*, a *Salmonella* species, *Pateurella multocida, Manhiemia haemolytica* and *Haemophilus somnus.*

In an embodiment, the low virulence BoHV-1 strain is strain V155. The vaccine enabled herein may further comprising additional genetic material encoding another antigen inserted via restriction endonuclease digestion. The vaccine may also be formulated in a pharmaceutical composition such as a pharmaceutical composition suitable for nasal administration.

A method for vaccinating a bovine animal against at least one antigen from a bovine pathogen is contemplated herein by administering to the bovine animal, a humoral immunity-inducing or cell-mediated immunity-inducing effective amount of a bovine herpes virus-1 (BoHV-1) genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes. The genetic material encoding the at least one antigen may be inserted into the BoHV-1 genome via an inducible recombination system such as by GET recombination.

As indicated above, the genetic material encoding the at least one antigen is inserted between the polyadenylation signals of two converging genes at a site selected from between 16600 to 16700, 22400 to 22500; 40,700 to 40,800; 58,000 to 59,000; 67,000 to 68,000; 74,000 to 76,000; 84,000 to 85,000; 90,000 to 91,000; and 96,000 to 97,000 of BoHV-1 reference sequence GenBank Accession No. AJ004801 or at a functionally equivalent site in another BoHV-1 including between two converging genes at a site selected from between 16600 to 16612 and 22400 to 22493 including between two converging genes at a site selected from between 16602 to 16603 and 22421 to 22470 including between two converging genes at a site selected from sites listed in Table 2.

In accordance with this method, the BoHV-1 produces a BoHV-1 antigen and/or at least one antigen is selected from the list consisting of an antigen from bovine viral diarrhea virus (BVDV) and an antigen from a microorganism.

Examples of the BVDV antigen is glycoprotein E0 or glycoprotein E2. Examples of a microorganism is *Mycoplasma bovis*, a *Salmonella* species, *Pateurella multocida, Manhiemia haemolytica* or *Haemophilus somnus.*

As indicated above the low virulence BoHV-1 strain includes V155. Additional genetic material encoding another antigen may also be inserted via restriction endonuclease digestion.

A method of producing a vaccine against at least one antigen from a bovine pathogen, is enabled herein by:

(i) incorporating a BoHV-1 genome from a low virulence BoHV-1 into a bacterial artificial chromosome (BAC) vector to form a BoHV-1 pre-vector BAC construct;

(ii) inserting genetic material encoding the at least one antigen into the BoHV-1 pre-vector BAC construct via an inducible recombination system to generate a recombinant BoHV-1-BAC (rBoHV-1-BAC) vector;

(iii) transforming and amplifying the rBoHV-1-BAC vector in a bacterial host; and (iv) purifying and isolating the rBoHV-1-BAC vector from the bacterial host and formulating the vector into a vaccine composition.

The inducible recombination system and sites of insertion are as disclosed above as are the antigens and their sources.

A cultured cell transfected with the rBoHV-1-BAC vector is also enabled herein.

A method taught therein is the vaccination against bovine respiratory disease complex (BRDC) in cattle, the method comprising administering to the cattle a humoral immunity-inducing or cell-mediated immunity-inducing effective amount of a bovine herpes virus-1 (BoHV-1) genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes.

Further contemplated herein is the use of a bovine herpes virus-1 (BoHV-1) genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes in the manufacture of a medicament in the vaccination of cattle against a bovine pathogen.

Aspects enabled herein are described by the following non-limiting Examples.

EXAMPLE 1

BoHV-1 Strain

The low virulence strain of BoHV-1 used was strain V155, originally described by Snowden (1964) supra. Nucleotide position numbers are based on GenBank Accession No. AJ004801.

EXAMPLE 2

Construction of a Recombinant Bovine Herpesvirus-1

BoHV-1

The BoHV-1 strain V155 was propagated in CRIB-1 cells (ATCC number CRL-11883), a pestivirus resistant derivative of MDBK cells. The CRIB-1 cells were maintained in Hank's minimal essential medium (H-MEM) containing antibiotics/antimyotics, non-essential amino acids, glutaMAX, 25 mM Hepes and 5% v/v donor calf sera at 37° C. All reagents utilized for cell and virus propagation were obtained from Invitrogen Australia unless otherwise stated.

CRIB-1 cells into six well plates (Corning) at $5 \times 10^5$ cells/well 24 h prior to transfection and incubate at 37° C. in an atmosphere of 5% v/v $CO_2$. For each transfection, diluted 1-2 µg of DNA to 100 µl using OptiMEM and mixed with 8 µl of Lipofectamine diluted to 100 µl using OptiMEM. The resultant mixture was incubated the mixture at room temperature for 45 min for formation of lipid/DNA complexes. The reaction volume was increased to 1 ml using OptiMEM and add to the cell monolayers which have been washed twice with OptiMEM. The transfected monolayers were then incubate the transfected monolayers at 37° C. with 5% v/v $CO_2$ for 16-18 h prior to the addition of 1 ml OptiMEM containing 10% v/v donor calf sera. 24 h the remove the transfection liquid and replaced with maintenance media. The monolayers for the development of CPE for up to 7 days post-transfection.

In order to purify the BoHV-1 genomic DNA the MDBK variant CRIB-1 cells were infected with BoHV-1 strain V155 at an MOI of 5 and the infection allowed to proceed to completion. The cell culture supernatant was then clarified by centrifugation at 5000 g for 10 min. Mature BoHV-1 virions were pelleted by centrifugation at 120000 g for 2 h. The BoHV-1 genomic DNA was recovered from the pelleted virus using the Qiagen genomic DNA extraction kit essentially as described by the manufacturer. The viral pellets are resuspend in Genomic DNA extraction buffer at a ratio of 1:65 of starting supernatant volume. Following elution from the column the BoHV-1 DNA was stored in aliquots at −20° C. HindIII was used to digest 1-2 µg of the DNA for comparison to known digestion profile of BoHV-1.

To facilitate the insertion of transgenes into the TK gene of BoHV-1 using GET homologous recombination, the deletion/insertion vector, pTK del was constructed. This vector contains two segments of the BoHV-1 thymidine kinase gene, TKleft and TKright, for use as recombination arms.

PCR for the BoHV-1 genome was carried out using Taq polymerase buffer (10 mM Tris-HCl, 1.5 mM $MgCl_2$, 50 mM KCl, pH8.5); 1.25 mM each of dATP, dCTP, dGTP and dTTP; 12.5 µM of each primer; 1 U of Taq DNA polymerase; 10-20 ng of genomic DNA 5% v/v DMSO; 10% v/v glycerol. These components had a final reaction volume of 20 µl.

The PCR cycling conditions used were; denaturation at 94° C. for 4 min; 35 cycles of 94° C. for 20 sec, 60° C. for 20 sec and 72° C. 120 sec; followed by 72° C. for 10 min and subsequently held at 4° C. Cycling was performed in a Hybaid Sprint thermocycler. After cycling the PCR product was resolved on 1% w/v agarose gel, the product excised and the DNA recovered using a Qiagen gel extraction kit according to the manufacturer's instructions.

TKleft and TKright were amplified from purified BoHV-1 genomic DNA by PCR. After amplification the products were purified using a Qiagen PCR purification column according to the manufacturer's instructions. The TKleft PCR product was digested with KpnI and SalI, gel purified and ligated into pBluescript-SK+ (Stratagene) which had also been digested with KpnI/SalI. The presence of the TKleft product was confirmed by sequencing. The TKright PCR product was cloned into the plasmid containing the TKleft product following EcoRI and SpeI digestion using standard cloning procedures. The resultant plasmid was called pTKdel (see Mahoney et al. (2002) supra). The primers used for the PCR amplification of the TK targeting regions are shown in Table 3. NsiI sites were incorporated into the Tkleft5' and Tkright3' primers to allow the excision of the transgene product from the pTKdel vector for recombination experiments. Four unique restriction endonuclease sites are present between the two TK crossover regions to allow the insertion of transgenes for transfer to the BoHV-1 genome.

In order to transfer the bacterial artificial chromosome (BAC) to the genome of BoHV-1, the BAC vector pBelloBAC II was digested with HindIII and gel purified. The digested BAC vector was ligated into pTKdel which had been digested with HindIII and dephosphorylated. Following transformation into *E. coli* strain XL1-Blue cells transformants were plated on selective agar containing 12.5 µg/ml chloramphenicol (CAP) and 100 µg/ml ampicillin. Insertion of the BAC vector was confirmed by excision with HindIII from DNA recovered from the resultant colonies. The TK deletion fragment (TK-BAC), containing the BAC vector flanked by the TKleft and TKright, was excised from pTKdel-BAC by digestion with NsiI and gel purified.

To promote homologous recombination between the BAC-TK fragment and genomic DNA, purified BoHV-1 DNA was digested with NsiI and dephosphorylated with bacterial alkaline phosphatase (Pharmacia). The BAC-TK fragment and NsiI digested BoHV-1 genomic DNA were co-transfected into CRIB-1 cells as described above. After 18-24 h the transfection mixture was removed and replaced with complete H-MEM containing 2 mM N,N'-hexamethylene-bis-acetamide (ICN) to promote viral gene transcription. The resultant viral supernatants were passaged once in CRIB-1 cells. The insertion of the BAC vector into the BoHV-1 genome was confirmed by a PCR assay specific for the chloramphenicol resistance gene using the primer pair ChloramF and ChloramR.

PCR templates were prepared by incubation of 10 µl of viral supernatant with 10 µl of lysis buffer (10 mM Tris-HCl pH8.0 containing 0.45% v/v Triton X-100 and 0.45% v/v Tween 20) with 2 µl of 10 mg/ml proteinase K followed by incubation at 60° C. for 2 h. The proteinase K was inactivated at 95° C. for 15 min. PCR reactions were performed using 1 to 2 µl of this preparation as template. Following PCR detection of the CAP resistance gene within the BoHV-1 genome bulk genomic DNA was recovered from virus particles as described above. To facilitate transformation and growth in a bacterial host the purified BoHV-1 genomic DNA was circularized using standard ligation procedures. Aliquots of the ligation mixtures were electroporated into E. coli DH10B cells (1.5 kV, 100Ω, 25 μF, Electroporator II; Invitrogen, San Diego). Following electroporation DH10B cells were recovered in 960 μl of SOB and incubated at 37° C. for 5 to 6 h with gentle shaking. Aliquots of the electroporation mix were plated onto LB plates containing 12.5 μg/ml CAP. Colonies were allowed to develop for 24 to 48 h at 37° C.

CAP resistant colonies were inoculated into 5 ml of LB broth containing 12.5 μg/ml CAP and grown at 37° C. for 16 h. BAC DNA was recovered using the standard alkaline lysis method. The HindIII digestion profiles of these BAC clones were compared to the HindIII profile of BoHV-1 genomic DNA. BAC clones with a similar HindIII profiles to genomic DNA were transfected into CRIB-1 cells as described above. The transfections were monitored daily for the development of CPE considered typical of BoHV-1.

Recombination of BoHV-1 BAC in DH10B occurred by co-electroporating the plasmid, pGETrec (available from by the Murdoch Childrens Research Institute, Melbourne, Australia), was electroporated into DH10B cells harbouring pBACBHV37 (BoHV-1 infectious clone). The DH10B cells containing both plasmids were selected on agar containing 12.5 μg/ml CAP and 100 μg/ml ampicillin. Electrocompetent cells of double resistant DH10B cells were prepared with 0.2% w/v arabinose induction during the log phase of cell growth to enable homologous recombination as previously described. The PCR amplified transgene of interest is then electroporated into these cells. Following recovery from the electroporation cuvette in SOC broth the cells are allowed to recover at 37° C. for at least 6 hr with shaking. All of the recovered cells on to chloramphenicol selective plates along with the appropriate antibiotic to select for the transgene.

To demonstrate that GET recombination could be utilized to modify the BoHV-1 genome, two different rBoHV-1 viruses were created. A rBOHV-1 was created where:

(i) The gene encoding gE was deleted. This was carried out by using a minimal kanamycin resistance cassette ($Kan^R$) which was amplified by PCR from the transposon EZ::TN<KAN-1> (Epicentre Technologies). The PCR primers: gE-KanF and gE-KanR, utilized included regions of 50 bp homology to the 5' (base number 121671-121720 of AJ004801) and 3' ends (base number 123371-123420 of AJ004801) of the gE gene. The resultant product, gE-$Kan^R$, was 1300 bp in length and was recovered following agarose gel separation using a gel extraction kit according to the manufacturer's instructions (Qiagen).

(ii) A heterologous gene encoding green fluorescent protein (GFP) was inserted into the V155 genome at the NsiI site REMR. This was carried out by inserting the GFP expression cassette into the genome located between UL46 (protein virion protein tegument) and UL44 (glycoprotein C using pGETrec facilitated recombination). the resultant product was recovered following agarose gel separation using a gel extraction kit according to the manufacture's instructions (Qiagen).

Other sites are selected from those listed in Table 2.

Approximately 200 ng of the gel purified PCR product was electroporated into the electrocompetent DH10B (pBACBHV37, pGETrec) as previously described. Recombinant colonies were identified by plating on LB plates containing 12.5 μg/ml CAP and 50 μg/ml kanamycin. PCR and Southern blot analysis confirmed the replacement of the gE gene with the $Kan^R$ cassette.

Viral genomic DNA for Southern blotting was purified as described below. Cell monolayers were infected with BoHV-1 strain V155 at an MOI of 5 and the infection was allowed to proceed until approximately 40% of the cells showed a "rounding up" type of morphology. Following removal of the growth medium the monolayer was gently washed twice with PBS at 0° C. Cell lysis buffer at 0° C. (10 mM sodium phosphate, pH 7.3 containing 1% v/v Nonidet P-40) was added to each flask (4 ml per 175 $cm^2$) and the flasks rocked so that the lysis buffer contacted the entire monolayer. The lysis buffer was removed and placed on ice, a further 4 ml added to each flask with gentle rocking it was removed and added to the initial lysis solution. The lysates were clarified at 4300 g for 10 min at 4° C. The supernatant was collected and centrifuged at 112700 g for 100 min at 5° C. The viral pellet was resuspended in 500 μl G2 buffer (Qiagen). Proteinase K (25 μl of 10 mg/ml) was added to the resuspended viral pellet followed by incubation at 50° C. for 1 h. Genomic viral DNA was recovered using genomic tip 20/G (Qiagen) as follows. The genomic tip 20/G was equilibrated with 1 ml of QBT buffer. The proteinase K treated material was diluted with an equal volume of QBT buffer and loaded on to the genomic tip (660 μl per tip). Tips were washed twice with 7.5 ml of QC buffer. Viral DNA was eluted from the tip with 2×1.5 ml QF buffer at 50° C. The DNA was precipitated, washed once with 75% v/v ethanol and resuspended in 50 μl of 10 mM Tris-HCl, pH 8.5.

Restriction enzyme digested DNA samples were electrophoresed on a 1% w/v gel in 0.5×TBE buffer for 13.5 h using field inversion gel electrophoresis (FIGE) apparatus (Biorad) at 5° C. The switch time ramp was 0.1 to 2 s linear shape with a forward voltage of 180 V and a reverse voltage of 120 V. The DNA fragments were transferred to Hybond-N non-charged membrane (Amersham) using capillary action and the DNA was fixed to the membrane using UV light. Probes were labeled with DIG-II-dUTP (Roche Molecular Biosystems). Probes were synthesized by PCR using a reaction mix containing: Taq polymerase buffer (10 mM Tris-HCl, 1.5 mM $MgCl_2$, 50 mM KCl, pH8.5), 1.25 mM each of dATP, dCTP, dGTP and dTTP, 1.25 μM DIG-II-dUTP, 1 U Taq Polymerase (Roche Molecular Biosystems), and 5 ng template DNA in a final volume of 20 μl. PCR reaction conditions were 94° C. for 3 min, 94° C. for 30 sec, 55° C. for 30 sec, 68° C. for 1 min for 35 cycles, 68° C. for 6 min. Following gel purification PCR probes were hybridized to membranes for 12-16 h at 55° C. (DIG System User's Guide for Filter Hybridisation, Roche Molecular Biosystems). Hybridizations were carried out in rotating bottles in a hybridization oven (Hybaid). Membranes were washed in dishes on a shaking platform at RT.

The replication kinetics of the various rBoHV-1 were determined using standard virological techniques. Briefly, 1 $TCID_{50}$ of virus was allowed to infect $1\times10^5$ CRIB-1 cells plated in 24-well plates for 90 min at 37° C. with 5% v/v $CO_2$ atmosphere. Any extracellular virus was then inactivated by addition of sodium citrate solution (40 mM sodium citrate, 10 mM KCl, 135 mM NaCl, pH 3.0), the cell layers were then washed twice with PBS and 1 ml of maintenance media added and incubated at 37° C. in a 5% $CO_2$ atmosphere. Viral supernatants and cell pellets were collected at 2, 4, 6, 12, 24, 48 and 72 h PI and frozen at −70° C. until required. The TCID$_{50}$ of each supernatant from each time point was then determined in triplicate. Following one freeze/thaw cycle the TCID$_{50}$ of intracellular virus was also determined for each time point in triplicate.

TABLE 3

| Primer | Primer Sequence | Sequence ID NO. | Product (size bp) and Plasmid |
|---|---|---|---|
| TKleft5' | 5'-GT GGTACC ATGCAT CTGATACCCCTTCGCCCGCTACTG-3'<br>      KpnI   Nsil | 1 | Tkleft (301 bp) |
| TKleft3' | 5'-TTTGC GTCGAC CCACTCCAGCGCGTCCCAG-3' | 2 | pTKdel |
| |       SalI | | |
| TKright5' | 5'-AT GAATTC GCCGCGCTCGCAGACCCCA-3'<br>     EcoRI | 3 | TKright, (337 bp), |
| TKright3' | 5'-GGACTAGTCATGCATCTCTAGCGCGAACTGACG-3' | 4 | pTKdel |
| |     SpeI    NsiI | | TK-probe |
| ChloramF | 5'-TCACTGGATATACCACCGTTGA-3' | 5 | CAP$^R$ gene, |
| ChloramR | 5'-TCACCGTAACACGCCACATCTT-3' | 6 | (402 bp) CAP$^R$-probe |
| gE-KanF | 5'-GGGGAACGGCGCACGCGAGAGGGTTCGAAAAGGGCATTTGGCAA TGCAAC-ATTTAAAT-ccacgttgtgtctcaaaatctctgatg-3'<br>                  SwaI | 7 | gE-Kan$^R$ (1237 bp) |
| gE-Kan$^R$ | 5'-TCGCGCTGCTACCACCGTGTAATCTGGTGCCGCCGGGTCCG CGCTGGCG-ATTTAAAT-cggttgatgagagctttgttgtaggtg-3' | 8 | |
| |       SwaI | | |
| BHV1.3 | 5'-GGG CAT TTG GCA ATG CAA C-3' | 9 | gE-probe |
| BHV1.6 | 5'-CGT CTC GTA TAT GCG GAT G-3' | 10 | (845 bp) |
| Kan$^R$fwd | 5'-GGT ATT AGA AGA ATA TCC TGA TTC-3' | 11 | Kan$^R$-probe |
| Kan$^R$rev | 5'-CTC ATC GAG CAT CAA ATG AAA CT-3' | 12 | (483 bp) |

EXAMPLE 3

Assessment of the Transmissibility of the rBoHV-1

The aim of this trial was to determine if the recombinant (genetically modified, GM) virus was capable of transmitting from vaccinated cattle to other cattle located at varying distances from the vaccinates. other ruminants (sheep and goats) were also located at varying positions relative to the vaccinated cattle to determine if the GM virus was transmissible to these ruminant species.

All cattle, sheep and goats were negative to BoHV-1 and Bovine viral diarrhea virus (BVDV) specific antibodies prior to the commencement of the animal trial. Animals of each species were randomly assigned to the following groups:

Sentinel Group A: Cattle (4), Sheep (4) and Goats (4) [note sheep and goats were penned together] located approximately 23 meters from the animal house;

Sentinel Group B: Cattle (2×2), Sheep (4) and Goats (4), located in pens in the Western end of the animal house;

Sentinel Group C: Cattle (2×2), Sheep (4) and Goats (4), located in the Eastern end of the animal house in pens opposite the vaccinated cattle; and Vaccine Contact Group: Vaccinated cattle (4) and Contact cattle (4), located in the Eastern end of the animal house.

Environmental swabs were taken from various locations in and around the animal house to test for the presence of the GM virus persisting outside its natural host (cattle) on the same day as animal samples were collected.

Prior to vaccination (Day 0) blood (20 ml) and nasal swabs were collected from all animals. The rectal temperature of all animals was also recorded. Cattle (94) were then vaccinated intra-nasally with 2 ml of prototype vaccine (BoHV-1 TK- E2+). Vaccinated cattle were penned with an unvaccinated bovine. For 14 days following vaccination (Day 1-14) nasal swabs were collected from all animals and rectal temperatures recorded for all animals. The trail concluded on Day 28 post-vaccination. At this time blood (20 ml) and nasal swabs were collected from all animals. In addition, rectal temperatures from all animals were recorded. After the collection of these samples all animals were euthanized and tissue samples (heart, lung, kidney, spleen, muscle, liver, brain and trigeminal ganglia) collected. Carcases were disposed of via high temperature incineration.

EXAMPLE 4

Comparison of the Wet or Freeze-Dried gmBoHV-1 Preparations

The aim of this trial was to compare the efficacy of gmBoHV-1 as a wet preparation and freeze-dried preparation to Rhinogard (Trade Mark) provided by Q-Vax Pty Ltd.

All cattle were negative to BoHV-1 and BVDV specific antibodies prior to the commencement of the animal trial. Cattle were randomly assigned to the following groups:

Group 1: Unvaccinated;

Group 2: Vaccinated intra-nasally with 1-2 ml of vaccine (gmBoHV-1) into 1 nostril;

Group 3: Vaccinated intra-nasally with 1-2 ml of vaccine (FD-gmBoHV-1) into 1 nostril;

Group 4: Vaccinated intra-nasally with 1-2 ml of vaccine (Rhinogard) into 1 nostril.

Environmental swabs were taken from various locations in and around the animal house to test for the presence of the GM virus persisting outside its natural host (cattle) on each day that animal samples were collected.

Prior to vaccination (Day 0) blood (20 ml), nasal swabs and nasal tampon swabs were collected from all cattle. The rectal temperatures and weight (combined pair weight) of all cattle was also recorded. Groups 2 and 4 were then vaccinated intra-nasally with the appropriate formulation. Freeze-dried gmBoHV-1 was reconstituted immediately prior to instillation. It was planned to administer the vaccine using a commercial applicator, however, due to problems in getting this to work, the vaccinations were delivered using a syringe as performed in previous research.

For 7 days following vaccination (Day 1-7) nasal swabs were collected from all animals and clinical signs were recorded for all animals.

All cattle were challenged with the BoHV-1 strain Q3932 on Day 14 post-vaccination as described below. Prior to the challenge nasal swabs and clinical signs were recorded for all animals. The cattle were then challenged with an intra-nasal instillation of $10^7$ $TCID_{50}$ BoHV-1 strain Q3932. After BoHV-1 challenge, nasal swabs were collected from all cattle and clinical assessments made on a daily basis (Day 15 to 18) using the scoring method described in Table 4.

TABLE 4

| Parameter | Score | Clinical Sign |
|---|---|---|
| Residual feed ration | 0 | 0-25% |
| | 1 | 25-50% |
| | 2 | 50-75% |
| | 3 | 75-100% |
| Coughing | 0 | Absent |
| | 1 | cough due to exercise |
| | 2 | coughing in pen |
| Demeanour | 0 | normal |
| | 1 | lethargic |
| | 2 | cast |
| Nasal discharge (N) | 0 | no discharge |
| | 1 | mild sero-mucous discharge |
| | 2 | moderate sero-mucous discharge |
| | 3 | mucous discharge with globules or small strands of mucopurulent exudate |
| | 4 | thick mucopurulent exudate |
| | 5 | thick mucopurulent exudate hanging from nostrils |
| Rectal temperature (° C.) | AM | PM |
| Weight[1] (kg) | | |
| Other Observations | | |

Clinical signs and parameters used in the clinical assessment of animals before and following challenge. Respiration rate was calculated by multiplying the number of breaths taken over 15 seconds by four. Respiration rate was observed in pens prior to daily sampling. Rectal temperatures were taken in the AM and repeated later in the day if a significant elevation was observed. Other clinical notes were also recorded as required, for example, audible breathing. clinical signs were assigned a numerical score (S).
Weight[1] was recorded as a combined measure for the cattle as the animals were more settled for sampling procedures when handled in the crush as pairs.

All cattle were challenged with *M. haemolytica* on Day 18 post-vaccination. Prior to the challenge, nasal swabs were collected and clinical signs were recorded for all animals. The cattle were then challenged with the intranasal instillation of approximately $5 \times 10^9$ cfu of *M. haemolytica*. After this secondary challenge, nasal swabs were collected from all cattle and clinical assessments made on a daily basis (Day 19 to 26) using the scoring method.

The trial concluded on Day 35 post-vaccination. At this time blood (20 ml), nasal swabs and nasal tampon swabs were collected from each animal. In addition, rectal temperatures from all animals were recorded. After the collection of these samples all animals were euthanized and tissue samples (heart, lung, kidney, spleen, muscle, liver, brain and trigeminal ganglia) were collected. Carcases were disposed of via deep burial.

EXAMPLE 5

Effects of Pre-Existing Immunity on Vaccine Efficacy

The aim of this trial was to determine if pre-existing immunity to either BoHV-1 or BVDV would affect the efficacy of the gmBoHV-1 vaccine. For example, if an animals was antibody positive for BoHV-1 would the gmBoHV-1 still be able to induce BVDV immunity (see Table 5).

TABLE 5

Assessment of the effect of pre-existing immunity on the efficacy of the recombinant BoHV-1 vaccine

| Treatment | Challenge | Status at vaccination[1] | Number of Animals |
|---|---|---|---|
| Vaccinated with FD-gmBoHV-1 | BoHV-1/Mh[2] | BohV-1 neg BVDV pos | 4 |
| Unvaccinated | BoHV-1/Mh[2] | BoHV-1 neg BVDV pos | 4 |
| Vaccinated with FD-gmBoHV-1 | BVDV/Mh[3] | BoHV-1 pos BVDV neg | 4 |
| Unvaccinated | BVDV/Mh[3] | BoHV-1 pos BVDV neg | 4 |

[1]Indicate serological status at the time of vaccination, BoHV-1 pos and BVDV pos indicate prior exposure to either BoHV-1 or BVDV as determined by the presence of antibody to the respective viruses in the serum collected prior to vaccination.
[2]Challenge with a BoHV-1 field strain Q3932 delivered via aerosol at 14 days post-vaccination, followed by challenge with *M. haemolytica* 5 days later as described in Example 4.
[3]As for 2 except BVDV field strain was used instead of BoHV-1.

Environmental swabs were taken from various locations in and around the animal house to test for the presence of the GM virus persisting outside its natural host (cattle) on each day that animal samples were collected.

Prior to vaccination (Day 0) blood (20 ml), nasal swabs and nasal tampon swabs were collected from all cattle. The rectal temperatures and weight (combined pair weight) of all cattle was also recorded. Groups were then vaccinated intra-nasally with the freeze-dried gmBoHV-1 that was reconstituted immediately prior to instillation. It was planned to administer the vaccine using a commercial applicator, however, due to problems in getting this to work, the vaccinations were delivered using a syringe as performed in previous research.

For 7 days following vaccination (Day 1-7) nasal swabs were collected from all animals and clinical assessments recorded for all animals.

All cattle were challenged with the BoHV-1 strain Q3932 on Day 14 post-vaccination as described below. Prior to the challenge, nasal swabs collected and clinical assessments recorded for all animals. The cattle were then challenged with intra-nasal instillation of $10^7$ $TCID_{50}$ BoHV-1 strain Q3932. After BoHV-1 challenge nasal swabs were collected from all cattle and clinical assessments made on a daily basis (Day 15-18) using the scoring method described in Table 3.

All cattle were challenged with *M. haemolytica* on Day 18 post-vaccination. Prior to the challenge nasal swabs were collected from all animals and rectal temperatures, respiration rates and weights recorded for all animals. The cattle were then challenged with an intra-nasal instillation of approximately $5 \times 10^9$ cfu of *M. haemolytica*. After this secondary challenge nasal swabs were collected from all cattle and clinical assessments made on a daily basis (Day 19-26) using the scoring method described in Table 3.

The trial concluded on Day 35 post-vaccination. At this time blood (20 ml), nasal swabs and nasal tampon swabs were collected from each animal. After the collection of these samples all animals were euthanized and tissue samples (heart, long, kidney, spleen, muscle, liver, brain and trigeminal ganglia) were collected. Carcases were disposed of via deep burial.

EXAMPLE 6

Reversion to Virulence

The aim of this trial was to determine if the serial passage of the gmBoHV-1 through multiple groups of cattle would show evidence of increasing virulence.

Environmental swabs were taken from various locations in and around the animal house to test for the presence of the GM virus persisting outside it natural host (cattle) on each day that animal samples were collected.

On the day prior to vaccination (Day 0) blood (20 ml), nasal swabs and nasal tampon swabs were collected from the cattle. The rectal temperatures and weight (combined pair weight) of all cattle was also recorded.

The cattle (2) were then vaccinated intra-nasally with the freeze-dried gmBoHV-1 which was reconstituted immediately prior to instillation. Following vaccination (Day 1-7) nasal swabs were collected form these animals and clinical assessments recorded for the animals on a daily basis.

Each passage experiment concluded on Day 14 post-vaccination. At this time blood (20 ml) nasal swabs and nasal tampon swabs were collected from each animal. After the collection of these samples all animals were euthanized and tissue samples (heart, lung, kidney, spleen, muscle, liver, brain and trigeminal ganglia) were collected. Carcases were disposed of via deep burial.

To complete the in vivo passage of the gmBoHV-1 virus, virus was reisolated from nasal swabs of the vaccinated cattle and used to reinfect two BoHV-1 naïve cattle. This process was repeated four times as described above. Note that only the first passage was completed using freeze-directed gmBoHV-1.

EXAMPLE 7

Excess Dose

The aim of this trial was to determine if the administration of an excessive dose (ED) of gmBoHV-1 would be deleterious to the vaccinated animal.

Environmental swabs were taken from various locations in and around the animal house to test for the presence of the GM virus persisting outside its natural host (cattle) on each day that animal samples were collected.

Prior to vaccination (Day 0) blood (20 ml), nasal swabs and nasal tampon swabs were collected from all cattle. The rectal temperatures and weight (combined pair weight) of all cattle was also recorded. Ed-Groups 1 to 3 were then vaccinated intra-nasally with the freeze-dried gmBoHV-1 which was reconstituted immediately prior to instillation as described below. It was planned to administer the vaccine using commercial applicator, however, due to problems in getting this to work, the vaccinations were delivered using a syringe as performed in previous research.

ED-Group 1: Vaccinate cattle (4) using intra-nasal instillation with ($10^{5-6}$ $TCID_{50}$) 1 ml of vaccine per nostril;

ED-Group 2: Vaccinate cattle (4) using intra-nasal instillation with ($10^{6-7}$ $TCID_{50}$) 1 ml of vaccine per nostril;

ED-Group 3: Vaccinate cattle (4) using intra-nasal instillation with ($10^{7-8}$ $TCID_{50}$) 1 ml of vaccine per nostril.

For seven days following vaccination (Day 1-7) nasal swabs were collected from all animals, and clinical assessments recorded for all animas. The trial concluded on Day 14 post-vaccination. At this time blood (20 ml), nasal swabs and nasal tampon swabs were collected from each animal. After the collection of these samples all animals were euthanized and tissue samples (heart, lung, kidney, spleen, muscle, liver, brain and trigeminal ganglia) were collected.

EXAMPLE 8

Genetic Stability of the gmBoHV-1

Restriction Enzyme Profiles on Back Passaged gmBoHV-1 Prototype Vaccine

From the nasal swabs collected throughout the Pen Trials, treatment group representatives were identified for viral isolation via mammalian cell culture (CRIB-1 cells). The presence of the bacterial artificial chromosome (BAC) within the backbone of the gmBoHV-1 enables the isolation and purification of plasmid DNA via bacterial replication to increase DNA yield.

Cell Culture

Confluent monolayers (70%) of CRIB-1 cells were prepared in six well plates for infection. The media was removed and the monolayers were washed with sterile phosphate buffered saline (PBS). To the washed monolayers 1 mL of the nasal swabs (in PBS and five times PSF) were added and incubated at 27° C. in 5% v/v $CO_2$ for 1 hour. The inoculums were removed and the cells washed once with 1 mL of PBS then allowed to recover in 3 mL of fresh media with PSF for 5 h at 37° C. and 5% $CO_2$.

At 6 h post infection, the monolayers were washed with 1 mL PBS then 1 mL of Total DNA. Lysis buffer (with fresh Proteinase K) was added to the monolayers and incubated for 4 hours at 37° C. This lysed the cells in situ releasing total DNA from the CrIB-1 cells and the replicating pBACBHV1E2s viral vaccine candidate. Harvesting the total DNA at this early stage of the infection ensures that some BAC DNA will be circular and suitable for transformation into bacteria for clonal replication.

Total DNA Extraction and Transformation

The total DNA was purified by using phenol/chloroform extraction and absolute alcohol to precipitate. The dried DNA pellet was then resuspended in 50 µl sterile high pure water (18 MΩ) at room temperature for 2 h. The volumes of each extraction varied depending upon the viscosity of the initial suspension of DNA. Transformation was achieved through electrophoration of 10 µl of the total DNA into 20 µl of DH10B ElectroMax competent cells (Invitrogen) and selection on bacterial plates containing 12.5 µg/ml Chloramphenicol. three colonies from each plate were picked into 50 mL LB broth containing 12.5 µg/ml Chloramphenicol and grown over 18 h at 37° C. with gentle shaking. The BAC DNA was extracted from these cultures using a modified alkaline lysis protocol (based upon the Roche high pure plasmid isolation kit for mini preparations). The bacterial cells were pelleted to removed the broth and resuspended in a Tris buffer. These cells were lysed to release the plasmid DNA which was then purified, removing the remaining proteins and slats. The pelleted DNA was dried and resuspended in 60 µl of 10 mM Tris-HCl (pH 8.5) overnight at 4° C.

Restriction Enzyme Profiles

The multiple clones from each isolate were analyzed for gross mutations via RE profile comparisons with the vaccine candidate (not back passaged via animals) and the parent viral vector (the pBACHBV1 37). 5 µl of the alkaline lysis prepared BAC DNA was digested for 4 h in a 20 µl total volume for enzymes HindIII and SalI, (NEB) according to the manufacturer's instructions.

Field Inversion Gel Electrophoresis (FIGE) was used to separate and visualize the band profiles for the digested BAC DNA. The 20 µl digested BAC DNA was loaded onto 0.7% agarose gels in 0.5 times TBE buffer (both with ethidium bromide) and run under the conditions for program 3 on the FIGE apparatus (BioRad) targeting the molecular weight size range of 5-100 Kb with a run time of 16 h.

EXAMPLE 9

In Vitro Capacity of the gmBoHV-1 to Infect, Replicate and Express the Transgene in Mammalian Cell-Lines There was no distinguishable difference between the parent BoHV-1 and the GM BoHV-1 in terms of the appearance of CPE. The CPE visualized was typical of BoHV-1 for both viruses. Typically, the amount of virus (deduced from the CT values) in both the BoHV-1 or gmBoHV-1 infected cell lines at 24 h post infection were similar (FIGS. 1A to C). For the HaCaT and CRIB-1 cell lines this was statistically significant, i.e. there was no significant difference in the amount of virus detected between the parent and GM ($P<0.05$ two tailed unpaired t test). For the remaining cell lines the difference in CT values between the parent and GM infected cells was no more than 2.5 and neither virus was consistently detected at a higher level in every cell line.

It was established that the insertion of the transgene (synthetic BVDV E2) into the parent BoHV-1 did not alter the capacity of the virus to infect and replicate in the various mammalian cell lines tested when compared to the parent virus. Interestingly, all of the cell lines tested were susceptible to BoHV-1 (both modified and unmodified) infection.

EXAMPLE 10

Transmission of the gmBoHV-1 from Cattle to Other Ruminants

A pen trial was conducted to determine if either the host range of BoHV-1 or the capacity of BoHV-1 to transmit to other ruminants had been altered as a result of the genetic modifications made. The pen trial included a series of sentinel cattle, sheep and goats placed at various distances from the vaccinated cattle.

At the commencement of the pen trial, it was noted that some of the cattle (particularly those in Sentinel Group A) had nasal discharge. There was also indications that some of the cattle had diarrhea. While it was not optimal to proceed with the trial it was not feasible to postpone the trial until these signs disappeared. These clinical signs were apparent in most of the cattle groups at some time throughout the trial—some animals appeared to have signs throughout the trial.

Testing of the nasal swab extracts from Day 0 of all animals with the BRD multiplex assay (FLOT.219) did not identify any samples containing, Bovine herpesvirus 1, bovine respiratory syncytial virus, bovine parainfluenza virus 3 or bovine pestivirus. Standard PCR assays for four genera of paramyxoviruses, adenovirus and enterovirus were also negative. The absence of BoHV1 and pestivirus was most important for this trial as the presence of either virus would have made it extremely difficult to interpret the results of the trial and may have caused the termination of the experiment.

Virus isolation attempts from the Day 0 nasal swab samples was interesting as there appeared to be some cytopathic effect (CPE) in the cells, indicating that a virus was present. However, attempts to passage these supernatants were not successful. Further attempts to identify if an infectious agent was associated with these signs were done by staining cells infected with the nasal swab from the animal with the most persistent clinical signs (Animal 377 from Sentinel A) with fluorescently labeled antibodies to the following bovine viruses; adenovirus 3, coronavirus, pestivirus, parainfluenza virus, respiratory syncytial virus, parvovirus and reovirus. The Day 0 nasal swab extract for Animal 377 was then tested using a standard PCR and an amplicon consistent with the expected size was obtained. However, sequencing of this amplicon indicated it was a non-specific amplification product. While the antibody staining appeared to be specific the identity of the pathogen remains unknown. Analysis of these samples with all molecular tests available in our lab did not identify the causative agent responsible for the observed clinical signs. Based on previous application of these tests it is considered highly unlikely the agent responsible was closely related to either BoHV-1 or BVDV and thus should not interfere with the interpretation of serological data for these viruses.

No gmBoHV-1 was detected either by RT-PCR or virus isolation from any of the sheep or goats from the three sentinel groups. Similarly no GM virus was detected either by RT-PCR or virus idolization from any of the cattle held in the Sentinels groups. A, B or C at anytime during the trial.

GM virus was detected in all of the vaccinated cattle. Typically, if a sample was positive for virus isolation (culture) it was positive by RT-PCR. The best recovery of virus was from an animal where nasal swabs were positive by RT-PCR from Day 1 to Day 6 and culture positive on Days 3 and 4.

Contact transmission of the GM virus was detected in two of the four pairs of animals.

Based on the RT-PCR amplifications of GM virus from nasal swabs, the peak period for virus replication in the vaccinated cattle was Day 3. GM virus was detected in three of the four vaccinates on Day 3.

To determine if the GM virus was able to persist outside the host (cattle) environmental swabs were collected from various surfaces at the trial site throughout the experiment. The extracts from these swabs were then tested for the presence of the GM virus using isolation in cell culture and RT-PCR. No GM virus was detected in any of the environmental swabs taken throughout the experiment.

Testing of the sera collected on Day 0 and Day 28 from all of the trial, animals demonstrated only the vaccinated cattle developed detectable antibodies to BoHV-1 in the Day 28 samples.

On the basis of the results from this trial, there was no transmission of the GM virus to other species (sheep and goats). Similarly, transmission of the GM virus over distances (>2 m) did not occur to cattle housed in proximity to the vaccinated cattle. Transmission of the GM virus to cattle housed with the vaccinated cattle did occur, though not at a high frequency.

The results of the trial did not support any alteration of the host range for the GM virus. Although some transmission did occur to the natural host (cattle), it was infrequent and maybe independent of the level of replication in the vaccinated animal. Added to this, no GM virus was detected outside the natural host of the virus in environmental swabs collected throughout the experiment. Together, these data demonstrate that the risk of releasing the GM virus into the environment is minimal.

EXAMPLE 11

Reactivation of gmBoHV-1

At the completion of each trial nasal swabs were collected from vaccinated and unvaccinated cattle. Total nucleic acids were extracted from these swabs and the presence of the gmBoHV-1 tested for using real-time PCR assays targeting BoHV-1 and the E2 transgene. All of these samples were negative by both PCR assays. On this basis it is reasonable to conclude that no reactivation occurred prior to the completion of the trial.

EXAMPLE 12

Persistence and Stability of the GM BoHV-1

No differences could be determined between the stability of the GM BoHV-1 and the parent virus in field conditions. The license stipulated that the trial was conducted in a PC1 animal house where exposure to direct sunlight was not possible. Exposure to sunlight in true field conditions would likely increase the instability of both the GM and parent virus due to UV light.

EXAMPLE 13

Residual Gene Products

No gmBoHV-1 was detected in any of the tissues tested for the animals using real time PCR. While it was considered unlikely that any gene products would be present a Western blot analysis was conducted on total protein extracts from the tissues of this animal. Based on these results it is unlikely that the GM virus or gene products it expresses persist in the tissues of vaccinated/infected animals.

It was not unexpected that the tissue samples of the animals were negative for the presence of both the GM virus and transgene products. Of the tissues tested, the presence of gmBoHV-1 was only expected in the trigeminal ganglia (TG) as this is the site where the parent virus is expected to form a latent infection. The failure to detect virus in the TG cold indicate that the gmBoHV-1 is unable to establish latent infection. Alternatively, the detection of the gmBoHV-1 in the TG maybe difficult as only a few cell bodies in the ganglion are likely to carry the virus—thus the likelihood of successful detection depends on the amount of tissue processed and test sensitivity.

EXAMPLE 14

Efficacy of a Freeze-Dried gmBoHV-1 Preparation

The efficacy of the gmBoHV-1 prototype vaccine as a freeze dried preparation (FD-gmBoHV-1) was compared to gmBoHV-1 as a wet preparation in vaccination/challenge trials. A group of cattle vaccinated with Rhinogard were included in this trial for comparison. Table 3 illustrates the virus detection results for all vaccinated and unvaccinated cattle from Day 0 (day of vaccination) to Day 7. Generally, the FD-gmBoHV-1 and gmBoHV-1 vaccines were shed at the most consistent rates on Day 3 with high levels of virus detected by PCR and virus consistently isolated (Table 6). The majority of cattle vaccinated with gmBoHV-1 were positive by both PCR assays on three or more days. The exception to this was an animal (designed 581) that was positive only on Day 3 post-vaccination.

No adverse clinical signs were observed in either the vaccinated or unvaccinated groups. BoHV-1 was detected in three of the unvaccinated animals on three occasions during this phase of the experiment. The virus detected was not the gmBoHV-1 as the PCR assay specific for the E2 transgene was negative for all animals. In addition the PCR results for BoHV-1 were weakly positive indicating that the results were due to contamination of the sample. This is most likely to have occurred during post-handling of the samples at the laboratory for those positive samples on Day 0.

There are some samples positive for the gmBoHV-1 on Day 0. These are likely due to contamination within the vaccination group as it was not logistically possible to decontaminate all surfaces between animals receiving the same treatment. Similarly animals were held within the crush in pairs as this typically made them more settled, thus transfer from the initial member of the pair to the other before the second animal was swabbed cannot be excluded.

To minimize the likelihood of any cross contamination between groups, groups were always processed in the following order; unvaccinated controls, Rhinogard vaccinated, followed by gmBoHV-1. In addition, the animal handling area including the crush, was decontaminated after the Rhinogard vaccinated group.

The BoHV-1 positive result for the unvaccinated animal 549 on Day 5 could have been due to transmission from the Rhinogard vaccinated group. Animal 549 was housed in pens adjacent to the Rhinogard vaccinate groups and as a result had to pass these animals on the way to the crush area. While animals were closely monitored during this process to prevent direct contact it is still feasible that animal 549 may have inhaled virus containing material while passing the Rhinogard pens as the animals tend to investigate the environment during this movement process. That the virus did not infect 549 and was only detected on Day 1 support that it was an environmental contamination rather than transmission of the virus from an infected/vaccinated animal. The data are shown in Table 6.

TABLE 6

| Animal ID | PCR Assay | DAY 0 PCR | DAY 1 PCR | DAY 2 PCR | DAY 2 VI | DAY 3 PCR | DAY 3 VI | DAY 4 PCR | DAY 5 PCR | DAY 6 PCR | DAY 7 PCR |
|---|---|---|---|---|---|---|---|---|---|---|---|
| \multicolumn{12}{c}{Vaccinated with freeze-dried gmBoHV-1} | | | | | | | | | | | |
| 543 | BHV | − | + | +++ | Neg | +++ | Pos | ++ | +++ | + | ++ |
| 38.6-40.1 | E2s | − | + | +++ | | +++ | | ++ | +++ | + | ++ |
| 561 | BHV | − | + | +++ | Neg | ++ | Pos | ++ | +++ | − | +++ |
| 38.3-39.7 | E2s | − | + | +++ | | ++ | | ++ | +++ | − | +++ |
| 577 | BHV | − | − | ++ | Neg | ++ | Pos | − | − | + | +++ |
| 38.4-39.4 | E2s | − | − | ++ | | ++ | | − | − | + | +++ |
| 581 | BHV | − | − | − | Neg | ++ | Neg | − | − | − | − |
| 38.8-39.7 | E2s | − | − | − | | ++ | | − | − | − | − |
| 540 | BHV | + | + | +++ | Neg | +++ | Pos | +++ | +++ | +++ | +++ |
| 38.5-39.2 | E2s | + | + | +++ | | +++ | | +++ | +++ | +++ | +++ |
| 553 | BHV | − | ++ | +++ | Neg | − | Pls | ++ | − | +++ | ++ |

TABLE 6-continued

| Animal ID | PCR Assay | DAY 0 PCR | DAY 1 PCR | DAY 2 PCR | DAY 2 VI | DAY 3 PCR | DAY 3 VI | DAY 4 PCR | DAY 5 PCR | DAY 6 PCR | DAY 7 PCR |
|---|---|---|---|---|---|---|---|---|---|---|---|
| 38.5-39.6 | E2s | − | ++ | +++ | | − | | ++ | − | +++ | ++ |
| 564 | BHV | − | ++ | − | Neg | +++ | Pos | ++ | +++ | ++ | − |
| 39.2-39.8 | E2s | − | ++ | − | | +++ | | ++ | +++ | ++ | − |
| 565 | BHV | + | − | + | Neg | ++ | Pos | + | ++ | − | − |
| 39.1-40.6 | E2s | + | − | + | | ++ | | + | ++ | − | − |
| Vaccinated with gmBoHV-1 | | | | | | | | | | | |
| 574 | BHV | + | + | +++ | Pos | +++ | Pos | ++ | ++ | ++ | + |
| 38.5-39.7 | E2s | + | − | +++ | | +++ | | ++ | ++ | ++ | + |
| 584 | BHV | + | + | +++ | NA | +++ | NA | +++ | +++ | ++ | − |
| 38.9-39.8 | E2s | + | + | +++ | | +++ | | +++ | +++ | ++ | − |
| 595 | BHV | − | − | +++ | NA | ++ | NA | ++ | ++ | − | − |
| 38.7-39.5 | E2s | − | − | +++ | | ++ | | ++ | ++ | − | − |
| 596 | BHV | − | − | +++ | NA | +++ | NA | ++ | + | + | − |
| 38.9-39.7 | E2s | − | − | +++ | | +++ | | ++ | + | + | − |
| Vaccinated with Rhinogard | | | | | | | | | | | |
| 550 | BHV | − | − | − | NA | − | NA | ++ | +++ | ++ | +++ |
| 38.7-39.5 | E2s | − | − | − | | − | | − | − | − | − |
| 551 | BHV | − | + | +++ | NA | +++ | NA | +++ | +++ | +++ | +++ |
| 38.7-39.1 | E2s | − | − | − | | − | | − | − | − | − |
| 555 | BHV | + | − | +++ | NA | ++ | NA | ++ | +++ | +++ | +++ |
| 38.6-39.6 | E2s | − | − | − | | − | | − | − | − | − |
| 570 | BHV | − | − | ++ | NA | ++ | NA | ++ | ++ | ++ | +++ |
| 38.5-39.4 | E2s | − | − | − | | − | | − | − | − | − |
| Unvaccinated | | | | | | | | | | | |
| 549 | BHV | − | − | − | NA | − | NA | − | + | − | − |
| 38.8-39.8 | E2s | − | − | − | | − | | − | − | − | − |
| 572 | BHV | − | − | − | NA | − | NA | − | − | − | − |
| 38.2-39.6 | E2s | − | − | − | | − | | − | − | − | − |
| 590 | BHV | + | − | − | NA | − | NA | − | − | − | − |
| 38.7-39.6 | E2s | − | − | − | | − | | − | − | − | − |
| 591 | BHV | + | − | − | NA | − | NA | − | − | − | − |
| 38.5-39.2 | E2s | − | − | − | | − | | − | − | − | − |
| 546 | BHV | − | − | − | NA | − | NA | − | − | − | − |
| 38.5-39.2 | E2s | − | − | − | | − | | − | − | − | − |
| 583 | BHV | − | − | − | NA | − | NA | − | − | − | − |
| 38.5-39.8 | E2s | − | − | − | | − | | − | − | − | − |
| 586 | BHV | − | − | − | NA | − | NA | − | − | − | − |
| 38.5-39.5 | E2s | − | − | − | | − | | − | − | − | − |
| 587 | BHV | − | − | − | NA | − | NA | − | − | − | − |
| 38.6-39.2 | E2s | − | − | − | | − | | − | − | − | − |

Vaccination phase: virus detection and virus isolation results for vaccinated and unvaccinated cattle. Cattle were vaccinated with gmBoHV-1 (Wet GM), freeze-dried gmBoHV-1 (FD-GM), Rhinogard (RG) or not vaccinated as part of pen trial to assess the efficacy of the FD-GM compared to Wet GM. following extraction of DNA from nasal swabs, the samples were tested using real-time PCR assays (P) specific for the gmBoHV-1 vector (BHV) and BVDV E2 transgene (E2). PCR results are expressed as, very strong (++++, Ct value <20), strong (+++, Ct value >20 but <30), weak (++, Ct value >30 but 35), very weak (+, Ct value >35 but <40) or negative (Pos), virus not recovered (Neg) or not attempted (NA). The temperature (° C.) range for each animal from Day 0 to 7 are shown below the animal number. All temperatures recorded were below 39.5° C. in the 7 days following vaccination, with the exception of, 581 Day 1 39.7° C.; 596 Day 7 39.7° C.; 565 Days 3 and 5 39.7° C. and 39.6° C., respectively.

Fourteen days after the initial vaccination of the treatment groups the cattle were challenged with either BoHV-1 strain Q3932 or the BVDV strain MD74. BoHV-1 was detected in the nasal swabs of two animals collected prior to administration of the challenge viruses (Table 7). The nasal swabs were negative for the E2 transgene which indicated that the detected virus was not the gmBoHV-1. There is no apparent source of this virus as all animals vaccinated with Rhinogard were virus negative indicating that the likely source was in post-collection handling of the samples. High levels of BoHV-1 challenge strain Q3932 were detected in all BoHV-1 challenged animals (Table 7) at three to four days post-challenge (Days 17 and 18).

Biosecurity measures were implemented to prevent either the transmission of BoHV-1 to the BVDV challenge groups, or the transmission of BVDV to the BoHV-1 challenge groups. Despite this there was significant infection of the BVDV challenge group with BoHV-1 (Table 7). The source of this cross-infection is not readily apparent. While no studies have been conducted to specifically assess the capacity of the Australian BoHV-1 strains to spread between cattle, it is generally accepted that close contact is required for transmission to occur. It may be that the majority of trials conducted that underpin this conclusion were vaccination trials and as a result there has been no observed transmission of the vaccine strain (BoHV-1 strain V155). However, in the challenge phase of these experiments all animals are challenged thus there was no opportunity to assess the transmission of the challenge strain to naïve animals. On this basis it would seem that the challenge strain Q3932 is more readily transmitted to other cattle by means other than close contact.

TABLE 7

| Animal ID | Assay | 14 P | 15 P | 16 P | 17 P | 18 P | 19 P | 20 P | 21 P | 22 P | 23 P | 24 P | 25 P |
|---|---|---|---|---|---|---|---|---|---|---|---|---|---|
| Vaccinated with freeze dried gmBoH-1 Challenge |||||||||||||
| 543 37.9-39.2 | BHV | − | ++ | +++ | ++++ | +++ | +++ | +++ | +++ | ++ | − | − | − |
| | E2s | − | − | − | − | − | − | − | − | − | − | − | − |
| | Mh | | | − | | | +++ | +++ | +++ | +++ | + | ++ | + |
| 561 38.1-39.1 | BHV | − | +++ | ++++ | +++ | ++++ | ++++ | +++ | +++ | +++ | +++ | ++ | ++ |
| | E2s | − | − | − | − | − | − | − | − | − | − | − | − |
| | Mh | | | − | | | ++ | +++ | +++ | ++ | ++ | − | ++ |
| 577 39.6-38.9 | BHV | − | ++ | +++ | +++ | ++++ | ++++ | ++++ | +++ | +++ | +++ | +++ | ++ |
| | E2s | − | − | − | − | − | − | − | − | − | − | − | − |
| | Mh | | | − | | | ++ | + | ++ | − | − | − | − |
| 581 38.3-40.2 | BHV | − | +++ | +++ | ++++ | ++++ | ++++ | ++++ | +++ | +++ | + | ++ | − |
| | E2s | − | − | − | − | − | − | − | − | − | − | − | − |
| | Mh | | | − | | | ++ | ++ | +++ | ++ | + | + | ++ |
| 574 38.0-39.4 | BHV | − | ++ | ++++ | +++ | +++ | +++ | ++++ | +++ | +++ | +++ | ++ | + |
| | E2s | − | − | − | − | − | − | − | − | − | − | − | − |
| | Mh | | | − | | | ++ | +++ | +++ | ++ | ++ | +++ | ++ |
| 584 38.0-39.1 | BHV | − | +++ | ++++ | ++++ | ++++ | +++ | +++ | +++ | ++ | − | − | + |
| | E2s | − | − | − | − | − | − | − | − | − | − | − | − |
| | Mh | | | − | | | +++ | +++ | +++ | ++ | ++ | − | + |
| 595 38.0-39.5 | BHV | − | ++++ | +++ | ++++ | +++ | ++++ | +++ | +++ | +++ | ++ | + | − |
| | E2s | − | − | − | − | − | − | − | − | − | − | − | − |
| | Mh | | | − | | | ++ | +++ | +++ | +++ | + | + | ++ |
| 596 38.2-39.9 | BHV | − | +++ | +++ | ++++ | +++ | ++++ | +++ | +++ | ++ | ++ | − | + |
| | E2s | − | − | − | − | − | − | − | − | − | − | − | − |
| | Mh | | | − | | | +++ | ++ | ++ | ++ | + | − | − |
| Unvaccinated and BoHV-1 Challenge |||||||||||||
| 549 38.4-39.5 | BHV | + | ++ | +++ | +++ | ++++ | ++++ | ++++ | ++++ | +++ | +++ | +++ | +++ |
| | E2s | − | − | − | − | − | − | − | − | − | − | − | − |
| | Mh | | | − | | | ++ | +++ | +++ | +++ | +++ | +++ | +++ |
| 572 38.3-40.2 | BHV | − | +++ | +++ | ++++ | ++++ | ++++ | ++++ | ++++ | +++ | +++ | ++ | ++ |
| | E2s | − | − | − | − | − | − | − | − | − | − | − | − |
| | Mh | | | − | | | +++ | +++ | +++ | +++ | +++ | ++ | ++ |
| 590 38.2-40.1 | BHV | − | +++ | +++ | +++ | ++++ | ++++ | +++ | ++++ | ++++ | +++ | ++ | ++ |
| | E2s | − | − | − | − | − | − | − | − | − | − | − | − |
| | Mh | | | − | | | ++ | ++ | ++ | +++ | +++ | ++ | ++ |
| 591 38.5-39.9 | BHV | − | +++ | ++++ | +++ | ++++ | ++++ | ++++ | ++++ | +++ | +++ | +++ | ++ |
| | E2s | − | − | − | − | − | − | − | − | − | − | − | − |
| | Mh | | | − | | | +++ | +++ | +++ | +++ | +++ | +++ | ++ |
| Rhinogard vaccinated/BoHV-1 Challenge |||||||||||||
| 574 38-39.4 | BHV | − | ++ | ++++ | +++ | +++ | +++ | ++++ | +++ | +++ | +++ | ++ | + |
| | E2s | − | − | − | − | − | − | − | − | − | − | − | − |
| | Mh | | | − | | | ++ | +++ | +++ | ++ | ++ | +++ | ++ |
| 584 38-39.1 | BHV | − | +++ | ++++ | ++++ | ++++ | +++ | +++ | +++ | ++ | − | − | + |
| | E2s | − | − | − | − | − | − | − | − | − | − | − | − |
| | Mh | | | − | | | +++ | +++ | +++ | ++ | ++ | − | + |
| 595 38-39.5 | BHV | − | ++++ | +++ | ++++ | +++ | ++++ | +++ | +++ | +++ | ++ | + | − |
| | E2s | − | − | − | − | − | − | − | − | − | − | − | − |
| | Mh | | | − | | | ++ | +++ | +++ | +++ | + | + | ++ |
| 596 38.2-39.9 | BHV | − | +++ | +++ | ++++ | +++ | ++++ | +++ | +++ | ++ | ++ | − | + |
| | E2s | − | − | − | − | − | − | − | − | − | − | − | − |
| | Mh | | | − | | | +++ | ++ | ++ | ++ | + | − | − |
| | Mh | | | − | | | ++ | + | + | + | + | − | + |
| 570 38.7-39.4 | BHV | − | ++ | ++ | +++ | +++ | +++ | +++ | +++ | +++ | +++ | +++ | ++ |
| | E2s | − | − | − | − | − | − | − | − | − | − | − | − |
| | Mh | | | − | | | ++ | ++ | ++ | ++ | + | − | − |
| Vaccinate with freeze-dried gmBoHV-1/BVDV Challenge |||||||||||||
| 540 38.4-39.5 | BHV | + | − | − | − | − | +++ | ++++ | +++ | ++++ | +++ | − | +++ |
| | E2s | − | − | − | − | − | − | − | − | − | − | − | − |
| | BVDV | | | + | | | − | − | − | − | − | − | − |
| | Mh | | | − | | | ++ | + | − | − | − | + | − |
| 553 38.4-39.5 | BHV | − | − | ++ | − | ++ | ++ | +++ | +++ | +++ | +++ | +++ | +++ |
| | E2s | − | − | − | − | − | − | − | − | − | − | − | − |
| | BVDV | − | − | − | − | − | − | − | − | − | − | − | − |
| | Mh | | | − | | | − | − | − | − | − | ++ | − |
| 564 38.9-39.5 | BHV | − | − | ++ | − | ++ | +++ | ++++ | ++++ | ++++ | ++++ | ++++ | ++++ |
| | E2s | − | − | − | − | − | − | − | − | − | − | − | − |
| | BVDV | − | − | − | − | − | − | − | − | − | − | − | − |
| | Mh | | | − | | | + | + | + | ++++ | − | + | − |
| 565 39-39.7 | BHV | − | − | − | ++++ | − | ++ | +++ | ++++ | ++++ | ++++ | +++ | +++ |
| | E2s | − | − | − | − | − | − | − | − | − | − | − | − |
| | BVDV | − | − | − | − | − | − | − | − | − | − | − | − |

TABLE 7-continued

| | | DAY | | | | | | | | | | | |
|---|---|---|---|---|---|---|---|---|---|---|---|---|---|
| Animal ID | Assay | 14 P | 15 P | 16 P | 17 P | 18 P | 19 P | 20 P | 21 P | 22 P | 23 P | 24 P | 25 P |
| | Mh | | | | - | | - | - | - | - | - | - | ++ |
| | | | | | | Unvaccinated/BVDV Challenge | | | | | | | |
| 546 | BHV | - | - | - | + | + | ++ | +++ | +++ | +++ | ++++ | +++ | +++ |
| 38-39 | E2s | - | - | - | - | - | - | - | - | - | - | - | - |
| | BVDV | - | - | - | + | - | - | - | - | - | - | - | - |
| | Mh | | | | - | | | | + | - | | ++ | ++ |
| 583 | BHV | - | - | - | - | ++ | +++ | +++ | +++ | +++ | ++++ | +++ | ++++ |
| 38.1-39.2 | E2s | - | - | - | - | - | - | - | - | - | - | - | - |
| | BVDV | - | - | - | - | - | - | - | - | - | - | - | - |
| | Mh | | | | - | | ++ | + | - | + | ++ | +++ | +++ |
| 586 | BHV | - | + | - | - | ++ | +++ | +++ | +++ | ++++ | ++++ | +++ | ++++ |
| 38.5-39.5 | E2s | - | - | - | - | - | - | - | - | - | - | - | - |
| | BVDV | - | - | - | - | - | - | - | - | - | - | - | - |
| | Mh | | | | - | | + | - | ++ | + | - | +++ | +++ |
| 587 | BHV | - | - | - | - | + | ++ | +++ | +++ | ++++ | ++++ | ++++ | +++ |
| 38.0-38.9 | E2s | - | - | - | - | - | - | - | - | - | - | - | - |
| | BVDV | - | - | - | - | - | - | - | - | - | - | - | - |
| | Mh | | | | - | | + | - | - | - | + | - | - |

Challenge phase virus detection, virus isolation and *Manhiemia haemolytica* detection results for vaccinated and placebo cattle after challenge. Day 14 post vaccination, cattle were challenged with either BoHV-1 ($10^7$ $TCID_{50}$) or BVDV, a subsequent challenge of *M. haemolytica* ($6.8 \times 10^9$ CFU) was administered to all cattle on Day 18. Following extraction of DNA from nasal swabs, the samples were tested using real-time PCR assays (P) specific for the BoHV-1 challenge strain Q3932 (HBV), BVDV E2 transgene (E2), BVDV challenge strain (BVDV) or *M. haemolytica* (Mh). PCR results are expressed as, very strong (++++, Ct value <20), strong (+++, Ct value >20 but <30), weak (++, CT value >30 but <35), very weak (+, Ct value >35 but <40), or negative (-). The temperature (° C.) ranges for each animal from Day 14-25 are shown below the animal number. One Animal 546 had a Ct value of 36.7 for BHV only at the end of the trial. The BHV PCR detects both the gmBoHV-1 and the challenge strain of BoHV-1.

Following the administration of the two challenge pathogens, animals were assessed for clinical signs on a daily basis. No clinical signs were recorded prior to the viral challenge from Day 14 to Day 18. After the second phase of the challenge with the *M. haemolytica* clinical signs were apparent in many of the groups. Generally, the clinical signs observed were mild. No elevated temperature, lose of appetite, alteration of respiratory rate or coughing were recorded at any time during the challenge phase.

Sera samples were collected from all animals at Day 0 (vaccination). Day 14 (viral challenge) and at the end of the trial immediately prior to euthanasia. The sera were tested for the presence of antibodies to BoHV-1 and BVDV using commercially available ELISA tests. The results of these tests are shown in Table 8. On Day 0, six of the cattle were positive for antibodies to BoHV-1. The cattle (60) were sourced from a single property and were all around the same age. Sera collected from all cattle was tested and were negative for antibodies specific to BVDV. However, the sera from 23 of the 60 cattle were positive for antibody to BoHV-1 from the same herd previously with levels considered to be more normal with less than 10% positive for BoHV-1. Due to the high seroprevalence and the relatively young age of the cattle (weaned approximately 8 weeks prior to arrival), it was considered likely that the high prevalence of BoHV-1 positives was due to maternal antibody. If maternal antibody was responsible then it would be expected that the amount of antibody present in the serum would decline overtime. As a result the cattle were retested for the presence of BoHV-1 antibodies on a weekly basis. Between the period of the first test and the third test three of the cattle went from positive to negative, one from positive to doubtful, 15 indicated reducing levels of antibody and four remained positive with steady levels of antibody. One animal appeared to develop antibodies to BoHV-1 (Number 598), however, it was seronegative when tested later.

At the commencement of the trial, all cattle positive for BoHV-1 antibodies (Table 8) had reduced levels compared to the previous test which again supports the presence of maternal antibodies in these animals.

As would be expected, all of the cattle vaccinated with the gmBOHV-1 sero-converted with respect to BoHV-1 by the end of the trial.

All cattle remained sero-negative to BVDV throughout the trial (Table 8). This was not expected as those animals challenged with BVDV were expected to sero-covert to BVDV. However, in the context of the virus detection results it is not surprising that no sero-conversion was detected as the BVDV strain used does not appear to have replicated in the unvaccinated animals. Animal 546 was the only animal PCR positive for BVDV (on Day 18) four days post challenge with BVDV while this could be considered a long time for virus to persist in the nasal cavity without infecting and replicating, if replication did take place, then it must have been at a very low level as the animal did no sero-convert nor was virus detected on any other day. The serology results support the virus detection results for BVDV indicating that the BVDV strain did not infect nor replicate in these animals.

TABLE 8

| | Animal | DAY 0 | | DAY 14 | | END OF TRIAL | |
|---|---|---|---|---|---|---|---|
| | ID | BVH | BVDV | BHV | BVDV | BHV | BVDV |
| F/D GM Vaccination | 581 | Pos | Neg | Neg | Neg | Pos | Neg |
| | 577 | Pos | Neg | Pos | Neg | Pos | Neg |

TABLE 8-continued

|  | Animal ID | DAY 0 | | DAY 14 | | END OF TRIAL | |
|---|---|---|---|---|---|---|---|
|  |  | BVH | BVDV | BHV | BVDV | BHV | BVDV |
|  | 543 | Neg | Neg | Neg | Neg | Pos | Neg |
|  | 561 | Neg | Neg | Neg | Neg | Pos | Neg |
| GM | 595 | Neg | Neg | Pos | Neg | Pos | Neg |
| Vaccination | 596 | Neg | Neg | Pos | Neg | Pos | Neg |
|  | 574 | Pos | Neg | Pos | Neg | Pos | Neg |
|  | 584 | Pos | Neg | doubt | Neg | Pos | Neg |
| Unvaccinated | 590 | Neg | Neg | Neg | Neg | Pos | Neg |
|  | 591 | Neg | Neg | Neg | Neg | Pos | Neg |
|  | 549 | Neg | Neg | Neg | Neg | Pos | Neg |
|  | 572 | Neg | Neg | Neg | Neg | Pos | Neg |
| Rhinogard | 570 | Neg | Neg | Neg | Neg | Pos | Neg |
| Vaccination | 555 | Neg | Neg | Pos | Neg | Pos | Neg |
|  | 551 | Neg | Neg | Pos | Neg | Pos | Neg |
|  | 550 | Neg | Neg | Neg | Neg | Pos | Neg |
| F/D GM | 553 | Pos | Neg | Pos | Neg | Pos | Neg |
| Vaccination | 540 | Pos | Neg | Pos | Neg | Pos | Neg |
|  | 564 | Neg | Neg | Neg | Neg | Pos | Neg |
|  | 565 | Neg | Neg | Pos | Neg | Pos | Neg |
| Unvaccinated | 586 | Neg | Neg | Pos | Neg | Pos | Neg |
|  | 587 | Neg | Neg | Neg | Neg | Pos | Neg |
|  | 583 | Neg | Neg | Neg | Neg | Pos | Neg |
|  | 546 | Neg | Neg | Neg | Neg | Pos | Neg |

Serological status of trial cattle to Bovine herpesvirus 1 (BHV) or bovine viral diarrhea virus (BVDV) at various stages throughout the vaccination trial. Sera samples from all cattle were tested using the Pourquier (Registered Trade Mark) ELISA IBR-IPV Serum and Milk for detection of serum antibodies to HBV and Pouriquier (Registered Trade Mark) ELISA BVD-MD-BD P80 Antibodies for detection of serum antibodies to BVDV. The BHV specific test will confirm prior infection with either wild-type BoHV-1 or gmBoHV-1. The BVDV specific test will confirm prior infection with wild-type BVDV, it does not detected antibodies specific for the BVDV E2.

EXAMPLE 15

Effects of Pre-Existing Immunity on Vaccine Efficacy

A possible risk of combining vaccines using genetic engineering is that pre-existing immunity to either the vector or the transgene could reduce any effectiveness of the vaccination. For example, in the current study, if cattle have pre-existing immunity to BoHV-1, which is the vaccine vector, then this may prevent replication of the gmBoHV-1 vaccine and either prevent or reduce the stimulation of any immunological response to the BVDV E2 protein encoded by the transgene. If this was to occur then the vaccinated cattle would not have the opportunity to benefit from the BVDV component of the vaccine, i.e. the cattle would still be susceptible to BVDV infection and development of disease.

To determine if pre-existing immunity could interfere with the efficacy, of the prototype vaccine, trials were conducted using animals that were antibody positive for either BoHV-1 or BVDV. The responses to vaccination with the gmBoHV-1 were then assessed in the two stage challenge model used previously.

Effects of Pre-Existing Immunity to BoHV-1 on Vaccine Efficacy

Cattle determined to be positive for antibody specific to BoHV-1 were vaccinated with the gmBoHV-1. DNA isolated from nasal swabs for these animals were then tested using real-time PCR assays specific for BoHV-1 and the E2 transgene. As expected all animals were negative for both assays on Day 0. Of the animals vaccinated with the gmBoHV-1, virus was consistently detected via both PCR assays from Day 1 to Day 6 post-vaccination for all animals except Animal 552.

No adverse clinical signs were observed in the vaccinated animals during the seven days post vaccination.

One of the unvaccinated animals (Animal 557) was positive for both PCR assays on Day 7. Attempts to isolate virus from this nasal swab were unsuccessful indicating that the PCR result was due to cross contamination of the sample either during sub-aliquoting or DNA extraction processes.

One of the vaccinated animals (Animal 556) was PCR positive for BoHV-1 on Day 7 only. As the PCR assay for the E2 transgene is more sensitive than the BoHV-1 assay, it would appear that this is a non-recombinant or wild-type strain of BoHV-1. No attempts were made to isolate virus from this sample. As use of BoHV-1 nucleic acids is wide spread within the laboratory cross contamination of the sample during either sub-aliquoting or DNA extraction appears the most likely cause of this result.

Fourteen days after the vaccination both the vaccinated and unvaccinated groups were challenged with BVDV. All cattle were negative by PCR for BoHV-1, E2 transgene and BVDV on Day 14. The cattle from both groups were challenged with BVDV and swabbed for a further five days. On Day 18 post-vaccination all cattle were challenge with *M. haemolytica*. Using BVDV strain three of the eight cattle were positive on at least one day of the challenge phase. This first animal was positive on Day 15 and the last on Day 23, a further three of the unvaccinated animals sero-converted to BVDV. These results are indicative that the BVDV challenge was successful.

Following the BVDV challenge all cattle were assessed for clinical signs on a daily basis. No clinical signs were observed between Day 14 and Day 18. Clinical signs observed from Day 19 to Day 25.

Serological results for these groups are shown in Table 9. As can be seen all animals except for 539 were positive for BoHV-1 on Day 0, it is suspected that this animal contained maternal antibodies that had dissipated prior to the commencement of this trial. This animal remained negative for BoHV-1 antibodies over the course of the study. As shown in Table 8, three of the eight animals (all unvaccinated) sero-converted to BVDV. An additional three of the eight animals (one unvaccinated and two vaccinated) demonstrated clearly increasing antibody levels to BVDV by the end of the trial. These results support the assertion that the BVDV challenge was successful.

TABLE 9

| | Animal | DAY 0 | | DAY 14 | | END OF TRIAL | |
|---|---|---|---|---|---|---|---|
| | ID | BHV | BVDV | BHV | BVDV | BHV | BVDV |
| Vaccinated | 552 | Pos | Neg | Pos | Neg | Pos | Neg |
| | 556 | Pos | Neg | Pos | Neg | Pos | Neg* |
| | 563 | Pos | Neg | Pos | Neg | Pos | Neg* |
| | 576 | Pos | Neg | Pos | Neg | Pos | Neg |
| Unvaccinated | 539 | Neg | Neg | Neg | Neg | Neg | Pos |
| | 557 | Pos | Neg | Pos | Neg | Pos | Pos |
| | 562 | Pos | Neg | Pos | Neg | Pos | Neg* |
| | 589 | Pos | Neg | Pos | Neg | Pos | Pos |

Serological status of trial cattle to bovine herpesvirus 1 (BHV) or bovine viral diarrhea virus (BVDV) at various stages throughout the vaccination trial. Sera samples from all cattle were tested using the Pourquier (Registered Trade Mark) ELISA IBR-IPV Serum and Milk for detection of serum antibodies to BHV and Pourquier (Registered Trade Mark) ELISA BVD-MD-BD P80 Antibodies, for detection of serum antibodies to BVDV. The BHV specific test will confirm prior infection with either wild-type BoHV-1 or gmBoHV-1. The BVDV specific test will confirm prior infection with wild-type BVDV, it does not detect antibodies specific for the BVDV E2. *Clear trend of increasing antibody levels.

Together these results indicate that the vaccination of the cattle with the gmBoHV-1 afforded protection to these cattle.

Effects of Pre-Existing Immunity to BVDV on Vaccine Efficacy (BoHV-1 Challenge)

Cattle determined to be positive for antibody specific to BVDV were vaccinated with the gmBoHV-1. DNA isolated from nasal swabs for these animals were then tested using real-time PCR assays specific for BoHV-1 and the E2 transgene. The results of these PCR analyses are shown in Table 10. As expected, all animals were negative for both assays on Day 0. Of the animals vaccinated with the gmBoHV-1, virus was consistently detected via both PCR assays from Day 2 to Day 6 post-vaccination for all animals. Virus was isolated from all animals on Day 3. Together this data support good uptake of the vaccine. Vaccine virus was not detected in any of the unvaccinated animals (Table 10).

No adverse clinical signs were observed in the vaccinated animals during the seven days post vaccination.

(Neg) or not attempted (NA). the temperature ranges (° C.) for each animal from Day 0 to 7 are shown below the animal number. *Virus isolation was attempted with no virus isolated, the ratios of the BoHV-1 and E2s PCR results was also inconsistent with previous results.

On Day 14 post-vaccination all cattle were challenged with BoHV-1 strain Q3932 as previously described. Nasal swabs were collected on a daily basis and clinical signs recorded. On Day 18 all animals were challenged with *M. haemolytica*. Nasal swabs were collected on a daily basis and clinical signs recorded to Day 25 post-challenge. DNA was extracted from all nasal swabs.

Fourteen days after the vaccination both the vaccinated and unvaccinated groups were challenged with BoHV-1. All cattle were negative by PCR for BoHV-1 and the E2 transgene on Day 14. The cattle from both groups were challenged with BoHV-1 strain Q3932 and swabbed for a further five days. On Day 18 post-vaccination all cattle were challenged with *M. haemolytica*. As expected, all animals were negative by PCR for the E2 transgene. The Q2932 was consistently detected in all animals, however, there was a trend towards vaccinated animals shedding less virus over a shorter time period compared to unvaccinated. A similar trend is evident for the *M. haemolytica* PCR assay.

Following the BoHV-1 challenge, all cattle were assessed for clinical signs on a daily basis. No clinical signs were observed between Day 14 and Day 18.

Serological testing of the cattle demonstrated sero-conversion with respect to BoHV-1 at the end of the trial for all cattle challenged with BoHV-1 as would be expected (Table 11).

TABLE 10

| Animal ID | | DAY 0 P | DAY 1 P | DAY 2 P | DAY 3 P | VI | DAY 4 P | DAY 5 P | DAY 6 P | DAY 7 P | VI |
|---|---|---|---|---|---|---|---|---|---|---|---|
| Vaccinated | | | | | | | | | | | |
| 559 | BHV | – | – | ++ | ++ | Pos | ++ | + | ++ | ++ | |
| 37.9-39.4 | E2s | – | – | ++ | ++ | | ++ | + | ++ | ++ | |
| 593 | BHV | – | – | ++ | ++ | Pos | ++ | ++ | ++ | ++ | |
| 38.2-39.1 | E2s | – | – | ++ | ++ | | ++ | ++ | ++ | ++ | |
| 573 | BHV | – | + | ++ | ++ | Pos | ++ | ++ | ++ | ++ | |
| 38.6-39.7 | E2s | – | + | ++ | ++ | | ++ | ++ | ++ | ++ | |
| 580 | BHV | – | + | + | ++ | Pos | ++ | + | ++ | + | |
| 38.6-40.4 | E2s | – | + | + | ++ | | ++ | + | ++ | + | |
| Unvaccinated | | | | | | | | | | | |
| 554 | BHV | – | – | – | – | NA | – | – | – | – | |
| 37.9-39.2 | E2s | – | – | – | – | | – | – | – | – | |
| 560 | BHV | – | – | – | – | NA | – | – | – | – | |
| 38.1-39.3 | E2s | – | – | – | – | | – | – | – | – | |
| 544 | BHV | – | – | – | – | NA | – | – | – | – | |
| 38.4-40.3 | E2s | – | – | – | – | | – | – | – | – | |
| 594 | BHV | – | – | – | – | NA | – | +* | – | 33.28 | – |
| 37.6-40.3 | E2s | – | – | – | – | | – | +* | – | 32.55 | – |

Virus detection and isolation results for cattle with existing immunity to BVDV. Vaccination phase: virus detection and virus isolation results for vaccinated and unvaccinated cattle with pre-existing immunity to BVDV. Cattle were either vaccinated with freeze-dried gmBoHV-1 (FD-GM) or remained unvaccinated. Following extraction of DNA from nasal swabs, the samples were tested using real-time PCR assays (P) specific for the gmBoHV-1 vector (BHV) and BVDV E2 transgene (E2). PCR results are expressed as, very strong (++++, Ct value <20), strong (+++, Ct value >20 but <30), weak (++, CT value >30 but <35), very weak (+, Ct value >35 but <40) or negative (–). Virus isolation was also attempted for selected samples (VI), isolation results are shown as virus recovered (Pos), virus not recovered

TABLE 11

| | | DAY 0 | | DAY 14 | | TRIAL END | |
|---|---|---|---|---|---|---|---|
| | Animal | BHV | BVDV | BHV | BVDV | BHV | BVDV |
| Vaccinated | 559 | Neg | Pos | Neg | Pos | Pos | Pos |
| | 593 | Neg | Pos | Pos | Pos | Pos | Pos |
| | 573 | Neg | Pos | Neg | Pos | Pos | Pos |
| | 580 | Neg | Pos | Neg | Pos | Pos | Pos |
| Unvaccinated | 554 | Neg | Pos | Neg | Pos | Pos | Pos |

Serological status of trial cattle to Bovine herpesvirus 1 (BHV) or bovine viral diarrhea virus (BVDV) at various stages throughout the vaccination trial. Sera samples from all cattle were tested using the Pourquier (Registered Trade Mark) ELISA IBR-IPV Serum and Milk for detection of serum antibodies to BHV and Pourquier (Registered Trade Mark) ELISA BVD-MD-BD P80 Antibodies for detection of serum antibodies to BVDV. The BHV specific test will confirm prior infection with either wild-type BoHV-1 or gmBoHV-1. The BVDV specific test will confirm prior infection with wild-type BVDV, it does not detect antibodies specific for the BVDV E2.

Pre-Existing Antibody to Either BVDV or BoHV-1 does not Prevent Replication or Recovery of the gmBoHV-1 Vaccine Virus from Vaccinated Animals Overall the results support the delivery of multiple antigens from other pathogens using a live viral vector. Further the results indicated that immune status of the host with respect to the vaccine vector will not negatively effect vaccine performance.

EXAMPLE 16

Reversion to Virulence

The use of live viral vaccines carries an inherent risk of the parent virus increasing in virulence if it is transmitted from one animal to another susceptible animal. In order to investigate if this was likely with the gmBoHV-1 and also to assess the stability of the genetic modifications made, the prototype vaccine was passaged four times through immunologically naïve (with respect to BoHV-1 and BVDV) cattle. These passage experiments were conducted in parallel with other vaccination trials.

As the gmBoHV-1 was most consistently detected and isolated on Day 3 post-vaccination, virus isolated at this time was used for the subsequent passage. The first passage was from animal number 598.

DNA isolated from nasal swabs for these animals were then tested using real-time PCR assays specific for BoHV-1 and the E2 transgene. All animals were negative for both assays on Day 0. Of the animals vaccinated with the gmBoHV-1 virus was consistently detected via both PCR assays from Day 2 to Day 7 post-vaccination for all animals. Virus was isolated from all animals on Day 3.

No adverse clinical signs were observed in the vaccinated animals during the seven days post vaccination. Mild elevated temperatures (>40° C.) were detected for some animals during the passages, however, these were sporadic and did not appear to be related to the presence of virus.

As expected the majority of the animals sero-converted to BoHV-1 at the end of the trial.

In summary, no evidence was found to support the increased virulence of the gmBoHV-1 during the passage experiments. Further the transgene appeared to be very stable with no evidence found to indicate loss through any of the passages.

Together the results of the passage experiments indicated that the E2 transgene is stable within the BoHV-1 genome. Similarly, no evidence was found of the gmBoHV-1 reverting to a more virulence phenotype. The genetic stability of the gmBoHV-1 was also investigating by examining the restriction endonuclease digestion patterns of genome DNA from reisolated viruses.

EXAMPLE 17

Excess Dose

To be economically viable, vaccines are typically supplied in multiple dose formulations. A possible drawn back of these formulations is the potential for adverse effects on the vaccinated animals if the vaccine is used as a higher than recommended does. To investigate the likelihood of adverse effects if the gmBoHV-1 was administered at a higher than recommended dose a trial was conducted where cattle were vaccinated with various concentrations of the vaccine.

Three groups of cattle (four per group) were vaccinated in each nostril with, $10^{6.5}$ $TCID_{50}$ of the gmBoHV-1 (10×Dose), $10^{5.5}$ $TCID_{50}$ of the gmBoHV-1 (expected effective dose) or $10^{4.5}$ $TCID_{50}$ of the gmBoHV-1 (0.1× expected effective dose). Cattle were monitored for clinical signs and nasal swabs taken on a daily basis following vaccination. DNA isolated from nasal swabs for these animals were then tested using real-time PCR assays specific for BoHV-1 and the E2 transgene.

Of the animals vaccinated with the gmBoHV-1, virus was consistently detected via both PCR assays from D2 to Day 7 post-vaccination for all animals. Virus was consistently isolated from animals on Day 3 were attempted.

No adverse clinical signs were observed in the vaccinated animals during the seven days post vaccination. Mild elevated temperatures (>40° C.) were detected fro some animals, however, these were sporadic and did not appear to be related to the presence of virus.

As expected, the majority of the animals sero-converted to BoHV-1 at the end of the trial. There was a trend towards more animals sero-converting in treatments receiving high quantities of virus as might be expected.

There was no evidence for any deleterious effects on animals vaccinated with high doses of the gmBoHV-1. At lower doses of the vaccine there appears to be less efficient up take of the vaccine based on the capacity to detect virus in nasal swabs by PCR detection and/or virus isolation.

EXAMPLE 18

Genetic Stability of gmBoHV-1

In this Example, the genetic stability of the gmBoHV-1 was evaluated by examining the genetic profiles of vaccine strains isolated from animals during the serial passage of the prototype vaccine through cattle.

This assessment was made by first reisolating the gmBoHV-1 from nasal swabs collected from infected cattle. To proved evidence that repeated passage in cattle would not adversely affect the genetic stability of the prototype vaccine these analysis were conducted on virus recovered form serial passage. The isolated and cloned genomes of randomly selected clones were then examined by restriction endonuclease digestion which is a well accepted method for assessing the genetic stability of herpesviruses. Two restriction endonucleases were used in the first was HindIII which cuts the BoHV-1 genome an estimated 12 times and thus provides a measure of any large scale genomic re-arrangements or recombination events. The second enzyme used as SalI which cuts the BoHV-1 genome an estimated 45 times and thus provides a measure of any finer scale genomic re-arrangements or recombination events.

Viruses were recovered from nasal swabs collected on Day 3 and Day 7 post-vaccination and restriction profiles determined. Three were no obvious large or smaller scale re-arrangements based on the HindII and SalI profiles, respectively.

On the basis of the restriction endonuclease profiles of viruses isolated after the passages in cattle, there was no evidence of any genetic variability. These data support the conclusion that the gmBoHV-1 used to vaccinate cattle in this study is highly stable.

Those skilled in the art will appreciate that aspects enabled herein are susceptible to variations and modifications other than those specifically described. It is to be understood that these aspects include all such variations and modifications. Enabled herein are all of the steps, features, compositions and compounds referred to or indicated in this specification, individually or collectively, and any and all combinations of any two or more of the steps or features.

BIBLIOGRAPHY

Mahoney et al. (2002) *Journal of Virology* 76 (13):6660-6668
Narayanan et al. (1999) *Gene therapy* 6:442-447
Orford et al. *Nucleic Acids Research* 28 (18):e84
Schumacher et al. (2000) *Journal of Virology* 74:11088-11098
Snowden (1964) *Australian Veterinary Journal* 40:277-288

The invention claimed is:

1. A vaccine against at least one antigen from a bovine pathogen, said vaccine comprising a bovine herpes virus-1 (BoHV-1) genome from a low virulence BoHV-1 having genetic material encoding the at least one antigen which is heterologous to BoHV-1 inserted between two converging BoHV-1 genes wherein the insertion does not substantially down-regulate expression of the BoHV-1 genes and wherein the genetic material encoding the at least one antigen is inserted between the polyadenylation signals of two converging genes at a site selected from between 16600 to 16612; 22449 to 22493; 40734 to 40768; 58229 to 58563; 67037 to 67091; 74994 to 75041; 84496 to 84528; 90732 to 90760; and 96870 to 96882 of BoHV-1 reference sequence GenBank Accession No. AJ004801.

2. The vaccine of claim 1 wherein the genetic material encoding the at least one antigen is inserted into the BoHV-1 genome via GET recombination.

3. The vaccine of claim 1 wherein the at least one antigen is inserted between two converging genes at a site selected from between 16600 to 16612.

4. The vaccine of claim 1 wherein the at least one antigen is selected from the group consisting of an antigen from bovine viral diarrhea virus (BVDV), an antigen from bovine parainfluenza3, an antigen from bovine respiratory syncytial virus and an antigen from a microorganism.

5. The vaccine of claim 4 wherein the BVDV antigen is selected from the group consisting of glycoprotein E0 and glycoprotein E2.

6. The vaccine of claim 4 wherein the microorganism is selected from the group consisting of *Mycoplasma bovis*, a *Salmonella* species, *Pasteurella multocida*, *Mannhiemia haemolytica* and *Haemophilus somnus*.

7. The vaccine of claim 1 wherein the low virulence BoHV-1 strain is strain V155.

8. A veterinary pharmaceutical composition comprising the vaccine of claim 1 and one or more pharmaceutically acceptable carriers, excipients and/or diluents.

9. The pharmaceutical composition of claim 8 formulated for nasal administration.

10. A method for vaccinating a bovine animal against at least one antigen from a bovine pathogen, said method comprising administering to said bovine animal a humoral immunity-inducing or cell-mediated immunity-inducing effective amount of a vaccine according to claim 1.

11. The method of claim 10 wherein administration is via intra-nasal, oral, intramuscular, sub-lingual, intravenous, subcutaneous, intra-arterial, skin spray, intra-vaginal or intra-rectal administration.

12. A method of producing a vaccine against at least one antigen from a bovine pathogen, said method comprising:
(i) incorporating a BoHV-1 genome from a low virulence BoHV-1 into a bacterial artificial chromosome (BAC) vector to form a BoHV-1 pre-vector BAC construct;
(ii) inserting genetic material encoding the at least one antigen into the BoHV-1 pre-vector BAC construct via GET recombination to generate a recombinant BoHV-1-BAC (rBoHV-1-BAC) vector, the genetic material encoding the at least one antigen is inserted between the polyadenylation signals of two converging genes at a site selected from between 16600 to 16612; 2249 to 22493; 40734 to 40768; 58229 to 58563; 67037 to 67091; 74994 to 75041; 84496 to 84528; 90732 to 90760; and 96870 to 96882 of BoHV-1 reference sequence GenBank Accession No. AJ004801;
(iii) transforming and amplifying the rBoHV-1-BAC vector in a bacterial host; and
(iv) purifying and isolating the rBoHV-1-BAC vector from the bacterial host and formulating the vector into a vaccine composition.

13. The method of claim 12 wherein the at least one antigen is inserted between two converging genes at a site selected from between 16600 to 16612.

14. The method of claim 12 wherein the at least one antigen is selected from the group consisting of an antigen from bovine viral diarrhea virus (BVDV), an antigen from bovine parainfluenza3, an antigen from bovine respiratory syncytial virus and an antigen from a microorganism.

15. The method of claim 14 wherein the BVDV antigen is selected from the list consisting of glycoprotein E0 and glycoprotein E2.

16. The method of claim 14 wherein the microorganism is selected from the group consisting of *Mycoplasma bovis*, a *Salmonella* species, *Pasteurella multocida*, *Mannhiemia haemolytica* and *Haemophilus* somnus.

17. The method of claim 12 wherein the low virulence BoHV-1 strain is strain V155.

18. A cultured cell transfected with the rBoHV-1-BAC vector of claim 12.

* * * * *